US008450290B2

(12) United States Patent
Worm et al.

(10) Patent No.: US 8,450,290 B2
(45) Date of Patent: *May 28, 2013

(54) METHODS FOR TREATING ANDROGEN RECEPTOR DEPENDENT DISORDERS INCLUDING CANCERS

(75) Inventors: Jesper Worm, Copenhagen (DK); Yixian Zhang, Piscataway, NJ (US)

(73) Assignees: Enzon Pharmaceuticals, Inc., Piscataway, NJ (US); Santaris Pharma A/S, Hoersholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/945,551

(22) Filed: Nov. 12, 2010

(65) Prior Publication Data

US 2011/0152348 A1   Jun. 23, 2011

Related U.S. Application Data

(63) Continuation-in-part of application No. 12/726,554, filed on Mar. 18, 2010, now Pat. No. 7,989,429, which is a continuation of application No. 12/324,033, filed on Nov. 26, 2008, now Pat. No. 7,737,125.

(60) Provisional application No. 60/990,125, filed on Nov. 26, 2007.

(51) Int. Cl.
A61K 48/00 (2006.01)
C07H 21/04 (2006.01)

(52) U.S. Cl.
USPC ...... 514/44; 536/23.1; 536/24.31; 536/24.33; 536/24.5

(58) Field of Classification Search
None
See application file for complete search history.

(56) References Cited

U.S. PATENT DOCUMENTS

| | | | |
|---|---|---|---|
| 4,914,210 | A | 4/1990 | Levenson et al. |
| 4,962,029 | A | 10/1990 | Levenson et al. |
| 6,733,776 | B1 | 5/2004 | Li et al. |
| 7,067,256 | B2 | 6/2006 | Roy et al. |
| 7,087,229 | B2 | 8/2006 | Zhao et al. |
| 7,595,304 | B2 | 9/2009 | Zhao et al. |
| 7,709,517 | B2 | 5/2010 | Sawyers et al. |
| 7,737,125 | B2 | 6/2010 | Worm |
| 7,772,433 | B2 | 8/2010 | Dalton et al. |
| 2004/0235773 | A1 | 11/2004 | Zhao et al. |
| 2005/0153935 | A1* | 7/2005 | Iversen et al. ............ 514/80 |
| 2005/0159376 | A1 | 7/2005 | McSwiggen et al. |
| 2005/0164970 | A1 | 7/2005 | Li |
| 2008/0090888 | A2 | 4/2008 | Jung et al. |
| 2010/0048676 | A1 | 2/2010 | Chang |
| 2010/0234451 | A1 | 9/2010 | Worm |

FOREIGN PATENT DOCUMENTS

| | | |
|---|---|---|
| EP | 0962972 | 10/1994 |
| WO | 9711170 | 3/1997 |
| WO | 0183740 | 11/2001 |
| WO | 2004046160 | 6/2004 |
| WO | 2004063331 | 7/2004 |
| WO | 2005027833 | 3/2005 |
| WO | 2005027833 A | 3/2005 |
| WO | 2007031081 | 3/2007 |
| WO | 2007031091 | 3/2007 |
| WO | 2007146511 | 12/2007 |
| WO | 2008034122 | 3/2008 |
| WO | 2008034123 | 3/2008 |
| WO | 2008053314 | 5/2008 |
| WO | WO 2010/057150 A1 * | 5/2010 |

OTHER PUBLICATIONS

Beane, R. L. et al., "Inhibiting gene expression with locked nucleic acids (LNAs) that target chromosomal DNA". Biochemistry 20070626 American Chemical Society US 46: 7572-7580, Jun. 26, 2007.
Eder, I. et al., "Inhibition of LNCaP prostate cancer cells by means of androgen receptor antisense oligonucleotides". Cancer Gene Therapy 7: 997-1007, Jan. 1, 2000.
Kurreck, J. et al, "Design of antisense oligonucleotides stabilized by locked nucleic acids", Nucleic Acids Research 30: 1911-1918, May 1, 2002.
International Search Report issued in PCT/DK2008/000417 and dated Jun. 16, 2009.
International Preliminary Report on Patentability issued in PCT/DK2008/000417 and dated Jun. 1, 2010.
Akinc et al., "A combinatorial library of lipid-like materials for delivery of RNAi therapeutics", Nature Biotechnology 26: 561-569, 2008.
Freier & Altmann, "The ups and downs of nucleic acid duplex stability: structure-stability studies on chemically-modified DNA:RNA duplexes", Nucl. Acid Research 25: 4429-4443, 1997.
Manoharan et al., "Novel Functionalization of the Sugar Moiety of Nucleic Acids for Multiple Labeling in the Minor Groove," Tetrahedron Letters 32: 7171-7174, 1991.
Monks et al., "Overexpression of wild-type androgen receptor in muscle recapitulates polyglutamine disease," PNAS 104: 18259-18264, Nov. 13, 2007.
Uhlmann, Eugen, "Recent advances in the medicinal chemistry of antisense oligonucleotides," Curr. Opinion in Drug Development 3: 203-213, 2000.
Zhao et al., "A New Platform for Oligonucleotide Delivery Utilizing the PEG prodrug approach," Bioconjugate Chemistry 16: 758-766, 2005.
Zhao, et al., "Delivery of G3139 using releasable PEG-linkers: Impact on pharmacokinetic profile and anti-tumor efficacy," J. of Controlled Release 119: 143-152. 2007.
Freir & Almann; "The ups and downs of nucleic acid duplex stability: structure-stability studies on chemically-modified DAN:RNA duplexes," Nucl. Acid Research, vol. 25, No. 22, pp. 4429-4443, 1997.
Gavrielides et al., "Androgens Regulate Protein Kinase Cs Transcription and Modulate Its Apoptotic Function in Prostate Cancer Cells" (Cancer Red, 2006, 66(24), pp. 11792-11801).

(Continued)

Primary Examiner — Amy Bowman
(74) Attorney, Agent, or Firm — Stoel Rives LLP

(57) ABSTRACT

The invention provides the combination use of antisense oligomers targeting androgen receptor mRNA and androgen receptor binding inhibitors that reduce androgen receptor activity for the treatment of androgen receptor related medical disorders, such as cancers, particularly prostate cancers and breast cancers.

8 Claims, 25 Drawing Sheets

OTHER PUBLICATIONS

Hoimes, et al. Redefining hormone resistance in prostate cancer. Therapeutic Advances in Medical Oncology Mar. 1, 2010, 2(2): 107-123: p. 114, Table 1: p. 117, col. 2.
International Search Report issued in PCT/US2011/060352 and dated May 18, 2012.
Knudsen, et al. Starving the addiction: new opportunities for durable suppression of AR signaling in prostate cancer. Clin Cancer Res. 2009, 15(15):4792-4798.
Notice of Allowance issued in U.S. Appl. No. 12/324,033 dated Feb. 22, 2010.
Notice of Allowance issued in U.S. Appl. No. 12/726,554 dated Feb. 28, 2011.
Office Action Issued in U.S. Appl. No. 13/149,155 dated Aug. 23, 2012.
Office Action Issued in U.S. Appl. No. 12/726,554 dated Oct. 29, 2010.
Office Action Issued in U.S. Appl. No. 12/324,033 dated Aug. 27, 2009.
Preliminary Amendment filed in U.S. Appl. No. 12/324,033 dated Feb. 27, 2009.
Response to Final Rejection Office Action Issued in U.S. Appl. No. 12/324,033 dated Feb. 4, 2010.
Response to Office Action filed in U.S. Appl. No. 12/726,554 dated Jan. 28, 2011.
Response to Office Action filed in U.S. Appl. No. 12/324,033 dated Oct. 14, 2009.
Response to Restriction Requirement in U.S. Appl. No. 12/726,554 dated Sep. 27, 2010.
Response to Restriction Requirement in U.S. Appl. No. 12/324,033 dated May 5, 2009.
Restriction Requirement issued in U.S. Appl. No. 12/726,554 dated Aug. 27, 2010.
Restriction Requirement issued in U.S. Appl. No. 12/324,033 dated Apr. 10, 2009.
Restriction Requirement issued in U.S. Appl. No. 13/149,155 dated Feb. 6, 2012.
Scher, et al. Antitumour activity of MDV3100 in castration-resistance prostate cancer; a Phase 1-2 study. Lancet. Apr. 24, 2010, 375(9724):1437-46.
Taplin, Drug Insight: role of the androgen receptor in the development and progression of prostate cancer. Nat Clin Pract Oncol. 2007, 4(4):236-44.
Tran, et al. Development of a Second-Generation Antiandrogen for Treatment of Advanced Prostate Cancer. Science 2009, 324(5928):787-790;p. 788, Fig1A.
Written Opinion of International Search Authority issued in PCT/DK2008/000417 and dated May 25, 2010.

* cited by examiner

FIG. 3A

Alignment human and mouse AR mRNA

```
                                                   1                                                50
SEQ ID NO: 81  NM_013476    (1)  --------------------------------------------------
SEQ ID NO: 1   NM_000044    (1)  CGAGATCCCGGGGAGCCAGCTTGCTGGGAGAGCGGGACGGTCCGGAGCAA
               Consensus    (1)  51                                                 100
SEQ ID NO: 81  NM_013476    (1)  --------------------------------------------------
SEQ ID NO: 1   NM_000044   (51)  GCCCAGAGGCAGAGGAGGCGACAGAGGGAAAAGGGGCCGAGCTAGCCGCT
               Consensus   (51)  101                                                150
SEQ ID NO: 81  NM_013476    (1)  --------------------------------------------------
SEQ ID NO: 1   NM_000044  (101)  CCAGTGCTGTACAGGAGCCGAAGGGACGCACCACGCCAGCCCCAGCCCGG
               Consensus  (101)  151                                                200
SEQ ID NO: 81  NM_013476    (1)  --------------------------------------------------
SEQ ID NO: 1   NM_000044  (151)  CTCCAGCGACAGCCAACGCCTCTTGCAGCGCGGCGGCTTCGAAGCCGCCG
               Consensus  (151)  201                                                250
SEQ ID NO: 81  NM_013476    (1)  --------------------------------------------------
SEQ ID NO: 1   NM_000044  (201)  CCCGGAGCTGCCCTTTCCTCTTCGGTGAAGTTTTTAAAAGCTGCTAAAGA
               Consensus  (201)  251                                                300
SEQ ID NO: 81  NM_013476    (1)  --------------------------------------------------
SEQ ID NO: 1   NM_000044  (251)  CTCGGAGGAAGCAAGGAAAGTGCCTGGTAGGACTGACGGCTGCCTTTGTC
               Consensus  (251)  301                                                350
SEQ ID NO: 81  NM_013476    (1)  --------------------------------------------------
SEQ ID NO: 1   NM_000044  (301)  CTCCTCCTCTCCACCCCGCCTCCCCCCACCCTGCCTTCCCCCCCTCCCCC
               Consensus  (301)  351                                                400
SEQ ID NO: 81  NM_013476    (1)  --------------------------------------------------
SEQ ID NO: 1   NM_000044  (351)  GTCTTCTCTCCCGCAGCTGCCTCAGTCGGCTACTCTCAGCCAACCCCCCT
               Consensus  (351)  401                                                450
SEQ ID NO: 81  NM_013476    (1)  --------------------------------------------------
SEQ ID NO: 1   NM_000044  (401)  CACCACCCTTCTCCCCACCCGCCCCCCCGCCCCCGTCGGCCCAGCGCTGC
               Consensus  (401)  451                                                500
SEQ ID NO: 81  NM_013476    (1)  --------------------------------------------------
SEQ ID NO: 1   NM_000044  (451)  CAGCCCGAGTTTGCAGAGAGGTAACTCCCTTTGGCTGCCAGCGGGCGAGC
               Consensus  (451)  501                                                550
SEQ ID NO: 81  NM_013476    (1)  --------------------------------------------------
SEQ ID NO: 1   NM_000044  (501)  TAGCTGCACATTGCAAAGAAGGCTCTTAGGAGCCAGGCGACTGGGGAGCG
               Consensus  (501)  551                                                600
SEQ ID NO: 81  NM_013476    (1)  --------------------------------------------------
SEQ ID NO: 1   NM_000044  (551)  GCTTCAGCACTGCAGCCACGACCCGCCTGGTTAGGCTGCACGCGGAGAGA
               Consensus  (551)  601                                                650
SEQ ID NO: 81  NM_013476    (1)  --------------------------------------------------
SEQ ID NO: 1   NM_000044  (601)  ACCCTCTGTTTTCCCCCACTCTCTCTCCACCTCCTCCTGCCTTCCCCACC
               Consensus  (601)  651                                                700
SEQ ID NO: 81  NM_013476    (1)  --------------------------------------------------
SEQ ID NO: 1   NM_000044  (651)  CCGAGTGCGGAGCCAGAGATCAAAAGATGAAAAGGCAGTCAGGTCTTCAG
               Consensus  (651)  701                                                750
SEQ ID NO: 81  NM_013476    (1)  --------------------------------------------------
SEQ ID NO: 1   NM_000044  (701)  TAGCCAAAAACAAAACAAACAAAAACAAAAAAGCCCGAAATAAAGAAAA
               Consensus  (701)  751                                                800
SEQ ID NO: 81  NM_013476    (1)  --------------------------------------------------
```

FIG. 3B

```
SEQ ID NO: 1   NM_000044    (751) AGATAATAACTCAGTTCTTATTTGCACCTACTTCAGTGGACACTGAATTT
               Consensus    (751) 801                                                850
SEQ ID NO: 81  NM_013476      (1) --------------------------------------------------
SEQ ID NO: 1   NM_000044    (801) GGAAGGTGGAGGATTTTGTTTTTTTCTTTTAAGATCTGGGCATCTTTTGA
               Consensus    (801) 851                                                900
SEQ ID NO: 81  NM_013476      (1) --------------------------------------------------
SEQ ID NO: 1   NM_000044    (851) ATCTACCCTTCAAGTATTAAGAGACAGACTGTGAGCCTAGCAGGGCAGAT
               Consensus    (851) 901                                                950
SEQ ID NO: 81  NM_013476      (1) --------------------------------------------------
SEQ ID NO: 1   NM_000044    (901) CTTGTCCACCGTGTGTCTTCTTCTGCACGAGACTTTGAGGCTGTCAGAGC
               Consensus    (901) 951                                               1000
SEQ ID NO: 81  NM_013476      (1) --------------------------------------------------
SEQ ID NO: 1   NM_000044    (951) GCTTTTTGCGTGGTTGCTCCCGCAAGTTTCCTTCTCTGGAGCTTCCCGCA
               Consensus    (951) 1001                                              1050
SEQ ID NO: 81  NM_013476      (1) --------------------------------------------------
SEQ ID NO: 1   NM_000044   (1001) GGTGGGCAGCTAGCTGCAGCGACTACCGCATCATCACAGCCTGTTGAACT
               Consensus   (1001) 1051                                              1100
SEQ ID NO: 81  NM_013476      (1) ----------------------------------GAATTCGGTGGAAGTTA
SEQ ID NO: 1   NM_000044   (1051) CTTCTGAGCAAGAGAAGGGGAGGCGGGGTAAGCGAATTAGGTGGAAGATT
               Consensus   (1051)                                   GAA TAGGTGGAAG T
                                  1101                                              1150
SEQ ID NO: 81  NM_013476     (18) CAGACAAGCTCAAGGATGGAAGTGCAGTTAGGCCTGGGAAGGGTCTACCC
SEQ ID NO: 1   NM_000044   (1101) CAGCCAAGCTCAAGGATGGAAGTGCAGTTAGGCGCTGGGAAGGGTCTACCC
               Consensus   (1101) CAG CAAGCTCAAGGATGGA GTGCAGTTAGGC CTGGGAAGGGTCTACCC
                                  1151                                              1200
SEQ ID NO: 81  NM_013476     (68) ACGGCCGCGATCCAAGACCTATCGAGGACGGTTCCAGAATCTGTTCCAGA
SEQ ID NO: 1   NM_000044   (1151) TCGGCCGCCGTCCAAGACCTACCGAGGAGCTTTCCAGAATCTGTTCCAGA
               Consensus   (1151)  CGGCC CC TCCAAGACCTA CGAGGAGC TTCCAGAATCTGTTCCAGA
                                  1201                                              1250
SEQ ID NO: 81  NM_013476    (118) GCGTGCGCGAAGCGATCCAGAACCCGGGCCCCAGGCACCCTGAGGCCGT
SEQ ID NO: 1   NM_000044   (1201) GCGTGCGCGAAGTGATCCAGAACCCGGGCCCCAGGCACCCAGAGGCCGGG
               Consensus   (1201) GCGTGCGCGAAG GATCCAGAACCCGGGCCCCAGGCACCC GAGGCCG
                                  1251                                              1300
SEQ ID NO: 81  NM_013476    (168) ACATAGCGCCTCCCGGCGCCGTTAC-------------------------
SEQ ID NO: 1   NM_000044   (1251) AGCGCAGCGCCTCCCGGCGCCAGTTTCTGCTGCTGGAGCAGCAGCAGCA
               Consensus   (1251) A C AGCGCCTCCCGGCGCC GTTT C
                                  1301                                              1350
SEQ ID NO: 81  NM_013476    (196) ------------------------------------------AGCAG
SEQ ID NO: 1   NM_000044   (1301) GCAGCAGCAGCAGCAGCAGCAGCAGCAGCAGCAGCAGCAGCAGCAGCAGC
               Consensus   (1301)                                            AGCAG
                                  1351                                              1400
SEQ ID NO: 81  NM_013476    (202) GGCAGGAGACTAGCCCCCGCCGGCGCGGCGGCAGCAGCACACTGAGGAT
SEQ ID NO: 1   NM_000044   (1351) AGCAAGAGACTAGCCCCAGCCGGCGAGCAG---CAGCAGCAGGCTGAGGAT
               Consensus   (1351) GCA GAGACTAGCCCC GGC GC GC G    CAGCAGCA   TGAGGAT
                                  1401                                              1450
SEQ ID NO: 81  NM_013476    (252) GGTTCTCCTCAAGCCCACATCGAGAGGCCCCACAGGCTACCTGGCCCTGGA
SEQ ID NO: 1   NM_000044   (1399) GGTTCTCCCCAAGCCCATCGTAGAGGCCCGCACAGGCTACCTGGTCCTGGA
               Consensus   (1401) GGTTCTCC CAAGCCCA  AGAGGCCCCACAGGCTACCTGG CCTGGA
                                  1451                                              1500
SEQ ID NO: 81  NM_013476    (302) GGAGGAACAGCAGCCTTCACAGCAGCAGCAGCCTCCGAGGCCCACCCTG
SEQ ID NO: 1   NM_000044   (1448) TGAGGAACAGCAACCTTCACAGCCCAGTGGCCCTGGAGTCCACCCCG
               Consensus   (1451) GAGGAACAGCA CCTTCACAGC GCAG C  CC   GAG  CCACCC G
```

FIG. 3C

```
                                 1501                                              1550
SEQ ID NO: 81  NM_013476   (352) AGAGCAGGTGCGTCCCGAGCCTGGCGGCGCACCGGTCTTCGCAAGGGG
SEQ ID NO: 1   NM_000044  (1498) ACAAAGGTTTGCGTCCCAGAGCCTGGAGCGCCCGTGGCGCGCAGCAAGGGG
               Consensus  (1501) AGAG  G TGC TCCC GAGCCTGG GC GCC    GC C  GCAAGGGG
                                 1551                                              1600
SEQ ID NO: 81  NM_013476   (402) CTGCCGCAGCAGCCACCAGCTCCTCCAGATCAGGATGACTCAGCTGCCCC
SEQ ID NO: 1   NM_000044  (1548) CTGCCGCAGCAGCTGCCAGCACCTCCGGACGAGGATGACTCAGCTGCCCC
               Consensus  (1551) CTGCCGCAGCAGC CCAGC CCTCC GA AGGATGACTCAGCTGCCCC
                                 1601                                              1650
SEQ ID NO: 81  NM_013476   (452) ATCCACGTTGTCCCTGCTGGGCCCCACTTTCCCAGGCTTAAGCAGCTGCT
SEQ ID NO: 1   NM_000044  (1598) ATCCACGTTGTCCCTGCTGGGCCCCACTTTCCCGGGCTTAAGCAGCTGCT
               Consensus  (1601) ATCCACGTTGTCCCTGCTGGGCCCCACTTTCCC GGCTTAAGCAGCTGCT
                                 1651                                              1700
SEQ ID NO: 81  NM_013476   (502) CCGCGGACATTAAAGACATTTGAACGAGGCCGGCACCATGCAACTTCTT
SEQ ID NO: 1   NM_000044  (1648) CCGGTGACATTAAAGACATCCTGAGCGAGGCCAGCACCATGCAACTCCTT
               Consensus  (1651) CCGC GAC TTAAAGACAT  TGA CGAGGCC GCACCATGCAACT CTT
                                 1701                                              1750
SEQ ID NO: 81  NM_013476   (552) CAGCAGCAGCAACACAGCAGAGCACCAACAGCAGCACCAACAGCACCA
SEQ ID NO: 1   NM_000044  (1698) CAGCA-----ACACAGCAGA--------------------------A
               Consensus  (1701) CAGCA     ACA CAGCAG A
                                 1751                                              1800
SEQ ID NO: 81  NM_013476   (602) ACAGCAGCAGCAGGCAATCTCCGAAGGCAGCAGCGCAAGAGCCAGGGAGG
SEQ ID NO: 1   NM_000044  (1716) GCAGCAGCCCAAGGCA---------G-CAGCAGCGGCAGAGCGAGGGAGG
               Consensus  (1751) CAG A C G AGG A         G CAGCAGCG  AGAGC AGGGAGG
                                 1801                                              1850
SEQ ID NO: 81  NM_013476   (652) CCACGGGGGCTCCCCTTCCTCCAAGGAAGTTACCTAGGGGGCACTTCA
SEQ ID NO: 1   NM_000044  (1756) CCTCGGGGGCTCCCACTTCCTCCAAGGACATTTACTTAGCGGCACTTGC
               Consensus  (1801) CC CGGGGGCTCCC CTTCCTCCAAGGA A TTAC TAGCGGGCA TTC
                                 1851                                              1900
SEQ ID NO: 81  NM_013476   (702) ACCATATCTGACAGTGCCAAGGAGTTGTGTAA-GCAGTGTGTGTCCAT
SEQ ID NO: 1   NM_000044  (1806) ACCATTTCTGACAACGCCAAGGAGTTGTGTAAGCAGTGTCGGTGTCCAT
               Consensus  (1851) ACCAT TCTGACA  GCCAAGGAGTTGTGTAA GCAGTGTC GTGTCCAT
                                 1901                                              1950
SEQ ID NO: 81  NM_013476   (752) GGAATTGGGTGTGGAAGCATTGGAACATCTGAGTCCAGGGAACAGCTTC
SEQ ID NO: 1   NM_000044  (1856) GGGCCTGGGTGTGGAGGCGTTGGACCATCTGAGTCCAGGGAACAGCTTC
               Consensus  (1901) GG  TGGGTGTGGA GC TTGGA CATCTGAGTCCAGGGAACAGCTTC
                                 1951                                              2000
SEQ ID NO: 81  NM_013476   (802) GGGGAGATGCATGTACGGGTGCTCCTGGGAGGTCCACCCGCGGTGCGT
SEQ ID NO: 1   NM_000044  (1906) GGGGCATTGCATGTACGCCCGCCTTTGGAGTTCCACCCGCTGTGCGT
               Consensus  (1951) GGGG GA TGCATGTACGC  C CT  TGGAG TCCACCCGC GTGCGT
                                 2001                                              2050
SEQ ID NO: 81  NM_013476   (852) CCCACTCCTTGTGCCCGCTGCTCGAATGCAAAGGTCTTCCCTTGACGA
SEQ ID NO: 1   NM_000044  (1956) CCCACTCCTTGTGCCCCATTGCCCGAATGCAAAGGTTTCTGCTAGACGA
               Consensus  (2001) CCCACTCCTTGTGCC CC TG CCGAATGCAAAGGT TC CT GACGA
                                 2051                                              2100
SEQ ID NO: 81  NM_013476   (902) AGGCCAGGCAAAAGCACTGAAGAACTGCTGAGTATTCCTCTTTCAAGG
SEQ ID NO: 1   NM_000044  (2006) CGGCCCAGGCAAGAGCACTGAAGATACTGCTGAGTATTCCCCTTTCAAGG
               Consensus  (2051)   GC CAGGCAA AGCACTGAAGA ACTGCTGAGTATTCC CTTTCAAGG
                                 2101                                              2150
SEQ ID NO: 81  NM_013476   (952) GAGGTTACGCCAAAGGATTGAAGGCTGAGAGCTTGGGTGCTCTGGCAGC
SEQ ID NO: 1   NM_000044  (2056) GAGGTTACACCAAAGGGCTAGAAGGCGAGAGCCTGGGTGCTCTGGCAGC
               Consensus  (2101) GAGGTTAC CCAAAGG T GAAGG GAGAGC T GG TGCTCTGGCAGC
```

FIG. 3D

```
                                    2151                                              2200
SEQ ID NO: 81   NM_013476  (1002)  AGTGAAGCAGGTAGCTCTGGGACACTTGAGATCCCGTCCTCTCTGTCTCT
SEQ ID NO: 1    NM_000044  (2106)  GCTGCAGCAGGTAGCTCTGGACACTCTTGAACTGCCGTCTACCCTGTCTCT
                Consensus  (2151)     TG AGCAGG AGCTC GGGACACTTGA  T CCGTC  C CTGTCTCT
                                    2201                                              2250
SEQ ID NO: 81   NM_013476  (1052)  GTTTAAATCTGGAGCACTAGACGAGGCAGCAGCATACCAGAATCGCGACT
SEQ ID NO: 1    NM_000044  (2156)  CTATAAATCTGGAGCACTCGACGAGGCAGCTGCGTACCAGAGTCGCGACT
                Consensus  (2201)   TA AA TC GGAGCACT GACGAGGCAGC GC TACCAGA TCGCGACT
                                    2251                                              2300
SEQ ID NO: 81   NM_013476  (1102)  ACTACAACTTTCCGCTGGCTCTGTCCGGCCGCCGCACCGCCGCCCCCT
SEQ ID NO: 1    NM_000044  (2206)  ACTACAACTTTCCACTGGCTCTGGCCGGACCGCCGCCCCGTCCGCGCCCT
                Consensus  (2251)  ACTACAACTTTCC CTGGCTCTG CCGG CCGCCGC CCC CCGCC CCT
                                    2301                                              2350
SEQ ID NO: 81   NM_013476  (1152)  ACCCATCCACACGGCGCTATCAAGCTGGAGAACCCATTGGACTACGGCAG
SEQ ID NO: 1    NM_000044  (2256)  CCCCATCCTCACGCTGCATCAAGCTGGAGAACCCGCTGGACTACGGCAG
                Consensus  (2301)   CCCATCC CACGC CG ATCAAGCTGGAGAACCC  TGGACTACGGCAG
                                    2351                                              2400
SEQ ID NO: 81   NM_013476  (1202)  CGCCTGGGCTGGGCGCGGAACCGCAATGCCGCTATGGGGACTGCGGTAGTC
SEQ ID NO: 1    NM_000044  (2306)  CGCCTGGGCGCGTCGGGCCGCACTGCCGCTATGCGGAGCTGCCGAGCG
                Consensus  (2351)  CGCCTGGGC GC GCGGC GCGCA TGCCGCTATGGGGAC TGG  AG C
                                    2401                                              2450
SEQ ID NO: 81   NM_013476  (1252)  TACATGGACGGCGTGTAGCCGGCCCAGCACTGGATGCCCCAGCCACC
SEQ ID NO: 1    NM_000044  (2356)  TGCATGGACGGCGTGCAGCGGACCCGGTTCTGGGTGCCCCTCAGCCGCC
                Consensus  (2401)  T CATGG G G GTG AGC GG CCC G CTGG TC CCC CAGCC CC
                                    2451                                              2500
SEQ ID NO: 81   NM_013476  (1302)  ACCTCTTCTTCCTGGCATACTCTCTTCACAGCTGAAGAAGGCCAATTATA
SEQ ID NO: 1    NM_000044  (2406)  CTTTCTCATCCTGGCACACTCTCTTCACAGCGAAGAAGCCCAGTTGTA
                Consensus  (2451)  C TC TC TCCTGGCA ACTCTCTTCACAGC GAAGAAGCCCA TT TA
                                    2501                                              2550
SEQ ID NO: 81   NM_013476  (1352)  TGGGCCGA---------------------------------G
SEQ ID NO: 1    NM_000044  (2456)  TGGACCGGTGTGGTGGTGGTGGGGGTGGTGGCGGCGGCGGCGGCGGCGG
                Consensus  (2501)  TGG CC                                            G
                                    2551                                              2600
SEQ ID NO: 81   NM_013476  (1360)  GAGGCGGCGGCGGCAGCAGAGCCCAACCGACGCCGCGGCTTGTAGCCCCC
SEQ ID NO: 1    NM_000044  (2506)  GCGGCGGCGGCGGCGGCGGCGCGGCCGCCGAAGGCCGGAGCTGTAGCCCCC
                Consensus  (2551)  G GGCGG GGCGGC GC GC GC   GCGA GC GG  CTGTAGCCCCC
                                    2601                                              2650
SEQ ID NO: 81   NM_013476  (1410)  TATGGCTACACTCGGCCCCCTCAGGGGCTGACAAGCCAGGAGAGTGACTA
SEQ ID NO: 1    NM_000044  (2556)  TAGGCTACACTCGGCCCCCTCAGGGGCTGGCGCCAGGAAAGCGACTT
                Consensus  (2601)  TA GGCTACACTCGGCCCCCTCAGGGGCTG C GCCAGGA AG GACT
                                    2651                                              2700
SEQ ID NO: 81   NM_013476  (1460)  CTCTGCCTCCGAACTGTGGTATCCTGGTGGAGTTGTGACAGAGTACCCT
SEQ ID NO: 1    NM_000044  (2606)  CACCGACCCGATCGTGTGGTACCCTGGCGCATCGTGACAGAGTCCCCT
                Consensus  (2651)  C C CC  C GA GTGTGGTA CCTGG GG  T GTGA CAGAGT CCCT
                                    2701                                              2750
SEQ ID NO: 81   NM_013476  (1510)  ATCCCAGTCCCAATTGTGTCAAAAGTGAAATGGGACTTTGGATGGAGAAC
SEQ ID NO: 1    NM_000044  (2666)  ATCCCAGTCCCACTTGTGTCAAAAGCGAAATGGGCCCTGGATGGATACC
                Consensus  (2701)  ATCCCAGTCCCA TTGTGTCAAAAG GAAATGGG CC TGGATGGA A C
                                    2751                                              2800
SEQ ID NO: 81   NM_013476  (1560)  TACTCCGGACCTTATGGGGACATGCGTTTGGAAGTACCAGGGACCATGT
SEQ ID NO: 1    NM_000044  (2706)  TACTCCGGACCTTGGGGGACATGCGTTTGGAGATTCCAGGGACCATGT
                Consensus  (2751)  TACTCCGGACCTTA GGGGACATGCGTTTGGA A T CCAGGGACCATGT
```

FIG. 3E

```
                              3451                                         3500
SEQ ID NO: 81   NM_013476  (2260) ACTTTGCACCTGACTTGGTTTTCAATGAGTACCGCATGCACAAGTCTCGG
SEQ ID NO: 1    NM_000044  (3406) ACTTCGCCCTGATCTGGTTTTCAATGAGTACCGCATGCACAAGTCCCGG
                Consensus  (3451) ACTT GC CCTGA TGGTTTTCAATGAGTACCGCATGCACAAGTC CGG
                              3501                                         3550
SEQ ID NO: 81   NM_013476  (2310) ATGTACAGCCAGTGTGTGATGAGGCACCTTCTCAAGAGTTTGGATG
SEQ ID NO: 1    NM_000044  (3456) ATGTACAGCCAGTGTGTCCAATGAGGCACCTTCTCAAGAGTTTGGATG
                Consensus  (3501) ATGTACAGCCAGTGTGT  G ATGAGGCACCT TCTCAAGAGTTTGGATG
                              3551                                         3600
SEQ ID NO: 81   NM_013476  (2360) GCTCCAAATAACCCCCAGGAATTCCTGTGCATGAAAGCACTGCTCCTCT
SEQ ID NO: 1    NM_000044  (3506) GCTCCAAATCACCCCCAGGAATTCCTGTGCATGAAAGCACTGCTACTCT
                Consensus  (3551) GCTCCAAAT ACCCCCAGGAATTCCTGTGCATGAAAGCACTGCT CTCT
                              3601                                         3650
SEQ ID NO: 81   NM_013476  (2410) TCAGCATTATTCCAGTGGATGGGCTGAAAAATCAAAATTCTTTGATGAA
SEQ ID NO: 1    NM_000044  (3556) TCAGCATTATTCCAGTCGATGGGCTGAAAAATCAAAATTCTTTGATGAA
                Consensus  (3601) TCAGCATTATTCCAGTGGATGGGCTGAAAAATCAAAATTCTTTGATGAA
                              3651                                         3700
SEQ ID NO: 81   NM_013476  (2460) CTTCGAATGAACTACATCAAGGAACTCGATCGGATCATTGCATGCAAAG
SEQ ID NO: 1    NM_000044  (3606) CTTCGAATGAACTACATCAAGGAACTCGATCGAATCATTGCATGCAAAG
                Consensus  (3651) CTTCGAATGAACTACATCAAGGAACTCGATCG ATCATTGCATGCAAAG
                              3701                                         3750
SEQ ID NO: 81   NM_013476  (2510) AAAAAATCCCACATCCTGCTCAAGGCGCTTCTACCAGCTCACCAAGCTCC
SEQ ID NO: 1    NM_000044  (3656) AAAAAATCCCACATCCTGCTCAAGACGCTTCTACCAGCTCACCAAGCTCC
                Consensus  (3701) AAA AATCCCACATCCTGCTCAAG CGCTTCTACCAGCTCACCAAGCTCC
                              3751                                         3800
SEQ ID NO: 81   NM_013476  (2560) TGCATTCTGTGCAGCCTATTGCAGAGAGCTGCATCAGTTCACTTTTTGAC
SEQ ID NO: 1    NM_000044  (3706) TGGATTCGTGCAGCCTATTGCAGAGAGCTGCATCAGTTCACTTTTTGAC
                Consensus  (3751) TG A TC GTGCAGCCTATTGC AGAGAGCTGCATCAGTTCACTTTTGAC
                              3801                                         3850
SEQ ID NO: 81   NM_013476  (2610) CTGCTAATCAAGTCCATATGGTGAGCGTGGACTTTCCTGAAATGATCGC
SEQ ID NO: 1    NM_000044  (3756) CTGCTAATCAAGTCCACATGGTGAGCGTGGACTTTCCGGAAATGATCGC
                Consensus  (3801) CTGCTAATCAAGTC CA ATGGTGAGCGTGGACTTTCC GAAATGATCGC
                              3851                                         3900
SEQ ID NO: 81   NM_013476  (2660) AGAGATCATCTCTGTGCAAGTGCCCAAGATCCTTTCTGGGAAAGTCAAGC
SEQ ID NO: 1    NM_000044  (3806) AGAGATCATCTCTGTGCAAGTGCCCAAGATCCTTTCTGGGAAAGTCAAGC
                Consensus  (3851) AGAGATCATCTCTGTGCAAGTGCCCAAGATCCTTTCTGGGAAAGTCAAGC
                              3901                                         3950
SEQ ID NO: 81   NM_013476  (2710) CCATCTATTTCCACACACAGTGAAGATTTGGAAACCCTATTCCCAAAAC
SEQ ID NO: 1    NM_000044  (3856) CCATCTATTTCCACACCCAGTGAAGCATTGGAAACCCTATTTCCCACC
                Consensus  (3901) CCATCTATTTCCACAC CAGTGAAG  TTGGAAACCCTA T CCC A  C
                              3951                                         4000
SEQ ID NO: 81   NM_013476  (2760) CCACTTGTTCCT-TTCCAGATGTCTTCTGCCTGTTATATAACTCTGCA
SEQ ID NO: 1    NM_000044  (3906) CCAGCTCATGCCCCTTTCAGATGTCTTCTGCCTGTTAT--AACTCTGCA
                Consensus  (3951) CCA CT  T CCC  TT CAGATGTCTTCTGCCTGTTAT  AACTCTGCA
                              4001                                         4050
SEQ ID NO: 81   NM_013476  (2809) CTACTCTCTGCAGTGCCTTGGGGAAATTCCTCTATGATGTACAGTCT
SEQ ID NO: 1    NM_000044  (3953) CTACTCTCTGCAGTGCCTTGGGG-AATTCCTCTATGATGTACAGTCT
                Consensus  (4001) CTACT CTCTGCAGTGCCTTGGGG AA TTCCTCTA TGATGTACAGTCT
                              4051                                         4100
SEQ ID NO: 81   NM_013476  (2859) GTCCTGAACAGGTTCCTAGTTCTATTTCTGGGCT-------CTCTT
SEQ ID NO: 1    NM_000044  (4002) GTCATGAACATGTTCCTGATTCTATTTCTGGGCTTTTTTTTCTCTT
                Consensus  (4051) GTC TGAACA GTTCCT A TTCTATTT CTGGGCT       CTC TT
```

FIG. 3F

```
                                        4101                                           4150
SEQ ID NO: 81   NM_013476  (2902)  CT------TTTTTCTTCTTCCCTCCCT  T  ACCCTCCCATGGCAC
SEQ ID NO: 1    NM_000044  (4052)  CTCTCCT TTCTTTTCTTCTTCCCTCCC AT AAACCCTCCCATGGCAGC
                Consensus  (4101)  CT       TT TTTTTCTTCTTCCCTCCCT T T  ACCCTCCCATGGCAC
                                        4151                                           4200
SEQ ID NO: 81   NM_013476  (2947)  TTTGA T TGCT C  ATTGTGGCTCCTGG CT TGTTTTGA T TGTT
SEQ ID NO: 1    NM_000044  (4102)  TTCACAG T GCTT CC ATTGTGGCTCCTAT CT GTGTTTGAA GG TGG T
                Consensus  (4151)  TT   GA T TGCT C  ATTGTGGCTCCT  CT TGTTTTGA T  TGTT
                                        4201                                           4250
SEQ ID NO: 81   NM_013476  (2997)  GTA--------------------------------------------
SEQ ID NO: 1    NM_000044  (4152)  GTATGCCTTTAAATCTGTGATGATCCTCATATGGCCCAGTGTCAAGTTGT
                Consensus  (4201)  GTA
                                        4251                                           4300
SEQ ID NO: 81   NM_013476  (3000)  --------------------------------------------------
SEQ ID NO: 1    NM_000044  (4202)  GCTTGTTTACAGCACTACTCTGTGCCAGCCACACAAACGTTTACTTATCT
                Consensus  (4251)
                                        4301                                           4350
SEQ ID NO: 81   NM_013476  (3000)  --------------------------------------------------
SEQ ID NO: 1    NM_000044  (4252)  TATGCCACGGGAAGTTTAGAGAGCTAAGATTATCTGGGGAAATCAAAACA
                Consensus  (4301)
                                        4351      4363
SEQ ID NO: 81   NM_013476  (3000)  --------------
SEQ ID NO: 1    NM_000044  (4302)  AAAACAAGCAAAC
                Consensus  (4351)
```

FIG. 4A

SEQ ID NO: 1
NM_000044

ORIGIN
```
   1 cgagatcccg ggcagccagc ttgctgggag agcgggacgg tccggagcaa gcccagaggc
  61 agaggaggcg acagaggcag aagcggccga gctagccgct ccagtgctgt acaggagccg
 121 aagggacgca ccacgcaagc cccagccgg ctccagcgac agccaacgcc tcttgcagcg
 181 cgcggcttc gaagctgccg ccggagctg ccctttcctc ttgggtgaag tttctaaaag
 241 ctgctaaaga gtcggaggaa gcaaggaaag tgcctggtag gactgacggc tgccttgtc
 301 ctcctcctct ccaccgcc tcgccccacc ctgccttccc ccctccccc gtcttctctc
 361 ccgcagctgc ctcagtcggc tactctcagc caaccccct caccaccctt ctcccaccc
 421 gccccccgc cccgtcggc acagcgctgc cagccgagt ttgcagagag gtaactccct
 481 ttggctgcga gcgggcgagc tagctgcaca ttgcaaagaa ggctcttagg agacaggaga
 541 ctgaggagcg gcttcagcac tgcagccacg agccgcctgg ttggcttgca cgccgagga
 601 acgctctgtt ttcccccact ctctctccac ctcctcctgc cttcccaac ccgagtcagg
 661 agccagagat cagaagatga aacggcagtc aggtcttcag tagccaataa accaaacaa
 721 caaaaacaaa aaagccgaaa taacgacto agatasteac tcagttctta attgccccta
 781 cttcagtgga cactgaattt gaggggtgga ggatttgtt tttctctttt aggatctggg
 841 catctttga atctaccctt cagtattaa gagacagacc gtcagcctag cagggcagat
 901 cttgtccacc gtgtgtcttc ttctgcaggg gactttgagg ctgtcagagc gcttttgcg
 961 tggttgatcc cgcaagttttc cttctctgga gcttccgca ggtggcagc tagctgcagc
1021 gactaccgca tcatcacagc ctgttgaact cctctgagca agagaaggggg aggcggggta
1081 agggaagtag gtggaagatt cagccatgct cdaggatgga agtgcagtta ggctcggga
1141 gggtctaccc tcggccgtcc tccaagaccct accgaggagc tctccagaat ctgttccaga
1201 gtgtgcgga agtgatacag aaccgagcc ccagccacc agaggcagg agcgagcac
1261 ctccggcgc aagttgctg ctgtgtcgc agcagcagca gcagcagcag cagcagcagc
1321 agtagcagca gcagcagcag cagcagcagc agcaagagac tagcccagg cagcagcagc
```
SEQ ID NO:44                                                SEQ ID NO:45
```
1381 agcagcagg tgaggatggt tctccccaag ccatcgtag aggccccaca ggctacctgg
1441 tcctgatgc gaaccgcaa ccttcacagc cgcagtcggc cctgtactgc cacgccgaga
1501 gaggtcgcgt cccagagcct ggagcccacg tggccgccag caaggggctg ccgcagcagc
1561 tgccagcacc tccggacgag gatgactcag ctgccccatc cacgttgtcc ctgctgggcc
1621 ccactttccc cggcttaagc agctgcttcg ctgaccttaa agacatcctg agcgaggcca
1681 gcaccatgca actccttcag caacaggcag aggagcagt atccgaaggc agcagcagcg
1741 ggagagtgag ggagcctcg gggctccca cttcctccaa ggacaattac ttaggcggca
1801 cttcgaccat ttctgccaac gccaggcagt tgtgtaaggc agtgtcggtg tccatgggcc
```
SEQ ID NO:46
```
1861 tgggtgtgga ggcgttggag catctgagtc cagggggaaca gcttcggggg gatcgcatgt
```
SEQ ID NO:47
```
1921 acgccccact tttgggagtt ccaccgctg tggtcccaag tgattgtgac ccttgccgc
1981 aatgcaaagg ttctctgct gacgacgcg caggcagag cactgaagat actgctgagt
2041 attcccactt caagggaggt tacccaaag ggctggagg cgagcccta ggctgtctg
2101 gcagcgctgc agccgggagc tcgggacac ttgaattgcc gtctaccctg tctctctcca
2161 agtccggage actggacgag gcagctgcgt accagagtcg agactactac aacttcccac
2221 tggctctggc cggaccgccg cccctccgc agctccca tcccacgct cgcatcagc
2281 tggagaaccc gctggactac ggcagcgct cggcggctgc ggcggcgcag tgccgctatg
2341 gggacctgc gagcctgcat ggcgcggtg cagcgggacc cggtcctggg tcaccctcag
```
SEQ ID NO:48
```
2401 ccgccgcttc ctcatcctgg cacactctct tcacagccga agaaggccag ttgtatgaac
2461 cgtgtggtgg tggtgggt ggtggcggcg gcggcgcgg cggcggcgg ggcggcggcc
2521 gcgcgacgc cgcgagcg gggctgtag cccctacgg ctacactgg cccctcagg
2581 ggctggcgg ccaggaagc gccttcaccg cacctgatgt gtggcaccct ggcggcatgg
```
SEQ ID NO:51
```
2641 tgagcagagt gccctatccc agtccacctt gtgtcaaaag cgaaatgggc cctggatgg
2701 atcgctactc cggaccttac ggggacatgc gttgagacc tgccagggac catgtttgc
```
SEQ ID NO:54
```
2761 ccattgacta ttactttccc cccagaaga cctgcctgat ctgtggagat caagcttctg
2821 gtgtcacta tggagctctc acatgtgga gtgcaggt cttcttcaaa agagccgctg
2881 aagggaaaca gaagtaccctg tgcgcaagca gaaatgattg cactattgat aaattacgaa
```
SEQ ID NO:57
```
2941 ggaaaaattg tccatccttgt cgtcttcggt aatgttatga agaagggtata gctctgggag
```
SEQ ID NO:58

FIG. 4B

SEQ ID NO: 1

FIG. 5A

SEQ ID NO: 1

FIG. 5B

SEQ ID NO: 1

Figure 6

```
SEQ ID NO: 81
LOCUS       NM_013476              2999 bp    mRNA    linear
DEFINITION  Mus musculus androgen receptor (Ar), mRNA.
ACCESSION   NM_013476
VERSION     NM_013476.3  GI:118129906
SOURCE      Mus musculus (house mouse)
ORIGIN
        1 gaattcggtg gaagctacag acaagctcaa ggatggaggt gcagttaggg ctgggaaggg
       61 tctacccacg gcccccatcc aagacctatc gaggagcgtt ccagaatctg ttccagagcg
      121 tgcgcgaagc gatccagaac ccgggcccca ggcaccctga ggccgctaac atagcacctc
      181 ccggcgcctg tttacagcag aggcaggaga ctagccccg gcggcggcg cggcagcagc
      241 acactgagga tggttctcct caagcccaca tcagaggccc cacaggctac ctggccctgg
      301 aggaggaaca gcagccttca cagcagcagg cagcctccga gggccaccct gagagcagct
      361 gcctccccga gcctggggcg gccaccgctc ctggcaaggg gctgccgcag cagccaccag
      421 ctcctccaga tcaggatgac tcagctgccc catccacgtt gtccctgctg ggcccactt
      481 tccaggctt aagcagctgc tccgccgaca ttaaagacat tttgaacgag gccggcacca
      541 tgcaacttct tcagcagcag caacaacagc agcagcacca acagcagcac caacagcacc
      601 aacagcagca ggaggtaatc tccgaaggca gcagcgcaag agccaggag gccacggggg
      661 ctccctcttc ctccaaggat agttacctag ggggcaattc aaccatatct gacagtgcca
      721 aggagttgtg taaagcagtg tctgtgtcca tgggattggg tgtggaagca ttggaacatc
      781 tgagtccagg gaacagctt cggggagact gcatgtacgc gtcgctcctg ggaggtccac
      841 ccgcggtgcg tcccactcct tgtgcgccgc tgcccgaatg caaaggtctt cccctggacg
      901 aaggcccagg caaaagcact gaagagactg ctgagtattc ctctttcaag ggaggttacg
      961 ccaaaggatt ggaaggtgag agcttgggt gctctggcag cagtgaagca ggtagctctg
     1021 ggacacttga gatcccgtcc tctctgtctc tgtataaaatc tggagcacta gacgaggcag
     1081 cagcatacca gaatcgcgac tactcaaact ttccgctggc tctgtccggg ccgccgcacc
     1141 ccccgccccc tacccatcca cacgccgta tcaagctgga gaaccattg gactacggca
     1201 gcgcctgggc tgcggcggca gcgcaatgcc gctatgggga cttgggtagt ctacatggag
     1261 ggagtgtagc cgggcccagc actggatcgc ccccagccac cacctcttct tcctggcata
     1321 ctctcttcac agctgaagaa ggccaattat atggggcagg aggcgggggc ggcagcagca
     1381 gcccaagcga tgccgggcct gtagccccct atggctacac tcggccccct caggggctga
     1441 caagccagga gagtgactac tctgcctccg aagtgtggta tcctggtgga gttgtgaaca
     1501 gagtacccta tcccagtccc aattgtgtca aaagtgaaat gggaccttgg atggagaact
     1561 actccggacc ttatgggac atgcgtttgg acagtaccag ggaccatgtt ttacccatcg
     1621 actattactt tccaccccag aagacctgcc tgatctgtgg agatgaagct tctggctgtc
     1681 actacggagc tctcacttgt ggcagctgca aggtcttctt caaaagagcc gctgaaggga
     1741 aacagaagta tctatgtgcc agcagaaacg attgtaccat tgataaattt cggaggaaaa
     1801 attgcccatc ttgtcgtctc cggaaatgtt atgaagcagg gatgactctg ggagctcgta
     1861 agctgaagaa acttggaaat ctaaaactac aggaggaagg agaaaactcc aatgctggca
     1921 gcccccactga ggacccatcc cagaagatga ctgtatcaca cattgaaggc tatgaatgtc
     1981 agcctatctt tcttaacgtc ctggaagcgt ttgagccagg agtggtgtgt gccggacatg
     2041 acaacaacca accagattcc tttgctgcct tgttatctag cctcaatgag cttggagaga
     2101 ggcagcttgt gcatgtggtc aagtgggcca aggccttgcc tggcttccgc aacttgcatg
     2161 tggatgacca gatggcggtc attcagtatt cctggatggg actgatggta tttgccatgg
     2221 gttggcggtc cttcactaat gtcaactcca ggatgctcta ctttgcacct gacttggttt
     2281 tcaatgagta ccgcatgcac aagtctcgga tgtacagcca gtgtgtgagg atgaggcacc
     2341 tgtctcaaga gtttggatgg ctccaaataa ccccccagga attcctgtgc atgaaagcac
     2401 tgctgctctt cagcattatt ccagtggatg ggctgaaaaa tcaaaaattc tttgatgaac
     2461 ttcgaatgaa ctacatcaag gaactcgatc gcatcattgc atgcaaaaga aagaatccca
     2521 catcctgctc aaggcgcttc taccagctca ccaagctcct ggattctgtg cagcctattg
     2581 caagagagct gcatcagttc actttgacc tgctaatcaa gtcccatatg gtgagcgtgg
     2641 actttcctga aatgatggca gatcatcatc tgtgcaagt gcccaagatc ctttctggga
     2701 aagtcaagcc catctatttc cacacacagt gaagatttgg aaaccctaat acccaaaacc
     2761 caccttgttc cctttccaga tgtcttctgc ctgttatata actctgcact acttctctgc
     2821 agtgccttgg gggaaattcc tctactgatg tacagtctgt cgtgaacagg ttcctcagtt
     2881 ctatttcctg ggcttctcct tcttttttt tcttcttccc tccctctttc accctcccat
     2941 ggcacatttt gaatctgctg cgtattgtgg ctcctgcctt tgttttgatt tctgttgta
//
```

Figure 7

SEQ ID NO: 82
```
LOCUS       NM_001032911            3175 bp    mRNA
DEFINITION  Macaca mulatta androgen receptor (AR), mRNA.
ACCESSION   NM_001032911
VERSION     NM_001032911.1  GI:74136372
SOURCE      Macaca mulatta (rhesus monkey)

ORIGIN
        1 cccaaaaaat aaaaacaaac aaaaacaaaa caaaacaaaa aaaacgaata aagaaaaagg
       61 taataactca gttcttattt gcacctactt ccagtggaca ctgaatttgg aaggtggagg
      121 attcttgttt tttcttttaa gatcgggcat cttttgaatc taccoctcaa gtgttaagag
      181 acagactgtg agcctagcag ggcagatctt gtccaccgtg tgtcttcttt tgcaggagac
      241 tttgaggctg tcagagcgct ttttgcgtgg ttgctccogc aagtttcctt ctctggagct
      301 tcccgcaggt gggcagctag ctgcagcgac taccgcatca tcacagcctg ttgaactctt
      361 ctgagcaaga gaaggggagg cggggtaagg gaagtaggtg gaagattcag ccaagctcaa
      421 ggatggaggt gcagttaggg ctggggaggg tctaccctcg gccgccgtcc aagacctacc
      481 gaggagcttt ccagaatctg ttccagagcg tgcgcgaagt gatccagaac ccgggcccca
      541 ggcacccaga ggccgcgagc gcagcacctc ccggcgccag tttgcagcag cagcagcagc
      601 agcagcaaga aactagcccc cggcaacagc agcagcagca gcagggtgag gatggttctc
      661 cccaagccca tcgtagaggc cccacaggct acctggtcct ggatgaggaa cagcagcctt
      721 cacagcctca gtcagcccg gagtgccacc ccgagagagg ttgcgtccca gagcctggag
      781 ccgccgtggc cgccggcaag gggctgccgc agcagctgcc agcacctccg gacgaggatg
      841 actcagctgc cccatccacg ttgtctctgc tgggccccac tttccccggc ttaagcagct
      901 gctccgccga ccttaaagac atcctgagcg aggccagcac catgcaactc cttcagcaac
      961 agcagcagga agcagtatcc gaaggcagca gcagcgggga agcgagggag gcctcggggg
     1021 ctcccactc ctccaaggac aattacttag agggcacttc gaccatttct gacacgctga
     1081 aggagctgtg taaggcagtg tcggtgtcca tgggcttggg tgtggaggcg ttggagcatc
     1141 tgagtccagg ggaacagctt cgggggggatt gcatgtacgc cccagttttg ggagttccac
     1201 ccgctgtgcg tcccactccg tgtgcccat tggccgaatg caaaggttct ctgctagacg
     1261 acagcgcagg caagagcact gaagatactg ctgagtattc cccttcaag ggaggttaca
     1321 ccaaagggct agaaggcgag agcctaggct gctctggcag cgctgcagca gggagctccg
     1381 ggacacttga actgccgtcc accctgtctc tctacaagtc cggagcactg gacgaggcag
     1441 ctgcgtacca gagtcgcgac tactacaact ttccactggc tctggccggg ccgcccgccc
     1501 ctccaccgcc tcccatccc cacgctcgca tcaagctgga gaacccgctg gactatggca
     1561 gcgcctgggc ggctgcggcg gcgcagtgcc gctatgggga cctggcgagc ctgcatggcg
     1621 cgggtgcagc gggaccoggc tctgggtcac cctcagcggc cgctcctca tcctgcaca
     1681 ctctcttcac agccgaagaa ggccagttgt atggaccgtg tggtggtggg ggcggcggcg
     1741 gtggcggcgg cggcggcggc gcaggcgagg cgggagctgt agcccctac ggctacactc
     1801 ggccacctca gggctggcg ggccaggaag gcgacttcac cgcacctgat gtgtggtacc
     1861 ctggcggcat ggtgagcaga gtgccctatc ccagtcccac ttgtgtcaaa agcgagatgg
     1921 gcccctggat ggatagctac tccggaccytt acggggacat gcgtttggag actgccaggg
     1981 accatgtttt gccaattgac tattactttc caccccagaa gacctgcctg atctgtggag
     2041 atgaagcttc tgggtgtcac tatggagctc tcacatgtgg aagctgcaag gtcttcttca
     2101 aaagagccgc tgaagggaaa cagaagtacc tgtgtgcag cagaaatgat tgcactattg
     2161 ataaattccg aaggaaaaat tgtccatctt gccgtcttcg gaaatgttat gaagcaggga
     2221 tgactctggg agcccggaag ctgaagaaac ttggtaatct gaaactacag gaggaaggag
     2281 aggcttccag caccaccagc ccccactgagg agacgccca gaagctgaca gtgtcacaca
     2341 ttgaaggcta tgaatgtcag cccatcttc tgaatgtcct ggaggccatt gagccaggtg
     2401 tggtgtgtgc tggacatgac aacaaccagc ccgactcctc cgcagccttg ctctctagcc
     2461 tcaatgaact gggagagaga cagcttgtac atgtggtcaa gtgggccaag gccttgcctg
     2521 gcttccgcaa cttacacgtg gacgaccaga tggctgtcat tcagtactcc tggatggggc
     2581 tcatggtgtt tgccatgggc tggcgatcct tcaccaatgt caactccagg atgctctact
     2641 ttgcccctga tctggttttc aatgagtacc gcatgcacaa atccgggatg tacagccagt
     2701 gtgtccgaat gaggcacctc tctcaagagt ttggatggct ccaaatcacc ccccaggaat
     2761 tcctgtgcat gaaagcgctg ctactcttca gcattattcc agtggatggg ctgaaaaatc
     2821 aaaaattctt tgatgaactt cgaatgaact acatcaagga actcgatcgt atcattgcat
     2881 gcaaaagaaa aaatcccaca tcctgctcaa ggcgtttcta ccagctcacc aagctcctgg
     2941 actccgtgca gcctattgcg agagagctgc atcagttcac ttttgaccotg ctaatcaagt
     3001 cacacatggt gagcgtggac tttccggaaa tgatggcaga gatcatctct gtgcaagtgc
     3061 ccaagatcct ttctgggaaa gtcaagccca tctatttcca cacccagtga agcattggaa
     3121 atccctattt cctcacccca gctcatgccc cctttcagat gtcttctgcc tgtta
```

Figure 8

SEQ ID NO:83
```
LOCUS       NP_000035                920 aa
DEFINITION  androgen receptor isoform 1 [Homo sapiens].
ACCESSION   NP_000035
VERSION     NP_000035.2  GI:21322252
DBSOURCE    REFSEQ: accession NM_000044.2
SOURCE      Homo sapiens (human)

ORIGIN
        1 mevqlglgrv yprppsktyr gafqnlfqsv reviqnpgpr hpeaasaapp gaslllqqq
       61 qqqqqqqqqq qqqqqqqqqq etsprqqqqq qgedgspqah rrgptgylvl deeqqpsqpq
      121 salechperg cvpepgaava askglpqqlp appdeddsaa pstlsllgpt fpglsscsad
      181 lkdilseast mqllqqqqqe avsegsssgr areasgapts skdnylggts tisdnakelc
      241 kavsvsmglg vealehlspg eqlrgdcmya pllgvppavr ptpcaplaec kgslldsag
      301 kstedtaeys pfkggytkgl egeslgcsgs aaagssgtle lpstlslyks galdeaaayq
      361 srdyynfpla lagpppppp phpharikle npldygsawa aaaaqcrygd laslhgagaa
      421 gpgsgspsaa asswhtlft aeeqglygpc gggggggggg gggggggggg gggeagavap
      481 ygytrppqgl agqesdftap dvwypggmvs rvpypsptcv ksemgpwmds ysgpygdmrl
      541 etardhvlpi dyyfppqktc licgdeasgc hygaltcgsc kvffkraaeg kqkylcasrn
      601 dctidkfrrk ncpscrlrkc yeagmtlgar klkklgnlkl qeegeasstt spteettqkl
      661 tvshiegyec qpiflnvlea iepgvvcagh dnnqpdsfaa llsslnelge rqlvhvvkwa
      721 kalpgfrnlh vddqmaviqy swmglmvfam gwrsftnvns rmlyfapdlv fneyrmhksr
      781 mysqcvrmrh lsqefgwlqi tpqeflcmka lllfsiipvd glknqkffde lrmnyikeld
      841 riiackrknp tscsrrfyql tklldsvqpi arelhqftfd lliksmhvsv dfpemmaeii
      901 svqvpkilsg kvkpiyfhtq
//
```

Figure 9

SEQ ID NO:84
```
LOCUS       NP_038504                899 aa
DEFINITION  androgen receptor [Mus musculus].
ACCESSION   NP_038504
VERSION     NP_038504.1  GI:7304901
DBSOURCE    REFSEQ: accession NM_013476.3
SOURCE      Mus musculus (house mouse)

ORIGIN
        1 mevqlglgrv yprppsktyr gafqnlfqsv reaiqnpgpr hpeaaniapp gaclqqrqet
       61 sprrrrqqh tedgspqahi rgptgylale eeqqpsqqqa aseghpessc lpepgaatap
      121 gkglpqqppa ppdqddsaap stlsllgptf pglsscsadi kdilneagtm qllqqqqqqq
      181 qhqqqhqqhq qqqevisegs sarareatga pssskdsylg gnstisdsak elckavsvsm
      241 glgvealehl spgeqlrgdc myasllggpp avrptpcapl peckglplde gpgksteeta
      301 eyssfkggya kglegeslgc sgsseagssg tleipsslsl yksgaldeaa ayqnrdyynf
      361 plalsgpphp pppthphari klenpldygs awaaaaaqcr ygdlgslhgg svagpstgsp
      421 pattssswht lftaeeqqly gpggggggsss psdagpvapy gytrppqglt sqesdysase
      481 vwypggvvnr vpypspncvk semgpwmeny sgpygdmrld strdhvlpid yyfppqktcl
      541 icgdeasgch ygaltcgsck vffkraaegk qkylcasrnd ctidkfrrkn cpscrlrkcy
      601 eagmtlgark lkklgnlklq eegensnags ptedpsqkmt vshiegyecq piflnvleai
      661 epgvvcaghd nnqpdsfaal lsslnelger qlvhvvkwak alpgfrnlhv ddqmaviqys
      721 wmglmvfamg wrsftnvnsr mlyfapdlvf neyrmhksrm ysqcvrmrhl sqefgwlqit
      781 pqeflcmkal llfsiipvdg lknqkffdel rmnyikeldr iiackrknpt scsrrfyqlt
      841 klldsvqpia relhqftfdl likshmvsvd fpemmaeiis vqvpkilsgk vkpiyfhtq
//
```

Figure 10

```
SEQ ID NO:85
LOCUS       NP_001028083                895 aa
DEFINITION  androgen receptor [Macaca mulatta].
ACCESSION   NP_001028083
VERSION     NP_001028083.1  GI:74136373
DBSOURCE    REFSEQ: accession NM_001032911.1
SOURCE      Macaca mulatta (rhesus monkey)

ORIGIN
        1 mevqlglgrv yprppsktyr gafqnlfqsv reviqnpgpr hpeaasaapp gaslqqqqqq
       61 qqetsprqqq qqqqgedgsp qahrrgptgy lvldeeqqps qpqsapechp ergcvpepga
      121 avaagkglpq qlpappdedd saapstlsll gptfpglssc sadlkdilse astmqllqqq
      181 qqeavsegss sgrareasga ptsskdnyle gtstisdsak elckavsvsm glgvealehl
      241 spgeqlrgdc myapvlgvpp avrptpcapl aeckgslldd sagkstedta eyspfkggyt
      301 kglegeslgc sgsaaagssg tlelpstlsl yksgaldeaa ayqsrdyynf plalagpppp
      361 pppphphari klenpldygs awaaaaagcr ygdlaslhga gaagpgsgsp saaassswht
      421 lftaeegqly gpcgggggg ggggggagea gavapygytr ppqglagqeg dftapdvwyp
      481 ggmvsrvpyp sptcvksemg pwmdsysgpy gdmrletard hvlpidyyfp pqktclicgd
      541 easgchygal tcgsckvffk raaegkqkyl casrndctid kfrrkncpsc rlrkcyeagm
      601 tlgarklkkl gnlklqeege assttsptee taqkltvshi egyecqpifl nvleaiepgv
      661 vcaghdnnqp dsfaallssl nelgerqlvh vvkwakalpg frnlhvddqm aviqyswmgl
      721 mvfamgwrsf tnvnsrmlyf apdlvfneyr mhksrmysqc vrmrhlsqef gwlqitpqef
      781 lcmkalllfs iipvdglknq kffdelrmny ikeldriiac krknptscsr rfyqltklld
      841 svqpiarelh qftfdlliks hmvsvdfpem maeiisvqvp kilsgkvkpi yfhtq
//
```

METHODS FOR TREATING ANDROGEN RECEPTOR DEPENDENT DISORDERS INCLUDING CANCERS

This application is a continuation-in-part of U.S. application Ser. No. 12/726,554 filed Mar. 18, 2010, which is a continuation of U.S. Application Ser. No. 12/324,033 filed Nov. 26, 2008 (now U.S. Pat. No. 7,737,125) which claims the benefit under 35 U.S.C. §119(e) of U.S. Provisional Application Ser. No. 60/990,125 filed Nov. 26, 2007, each of which is incorporated herein by reference in its entirety.

FIELD OF INVENTION

The invention relates to the field of androgen receptor targeted therapies.

BACKGROUND

The androgen receptor (AR) is a type of nuclear receptor which is activated by binding of either of the androgenic hormones testosterone or dihydrotestosterone. The main function of the androgen receptor is as a DNA binding transcription factor which regulates gene expression. However the androgen receptor also has additional functions independent of DNA binding. The androgen receptor is most closely related to the progesterone receptor, and progestins in higher dosages can block the androgen receptor.

Whilst in humans the AR gene is single copy and found on the X chromosome at position Xq11-12, the receptor itself exists in two iso-forms (A and B). AR-A is an 87 kDa protein which lacks the first 187 amino acids (N-terminal truncation). Isoform AR-B is the full length 110 kDa version.

The binding of androgen to the androgen receptor induces a conformational change to the receptor, resulting in a dissociation of heat shock proteins, dimerization and transport from the cytosol to the cell nucleus where the androgen receptor dimer binds to specific DNA sequences—referred to as hormone response elements. Depending on the interaction with other nuclear proteins, the AR controls gene expression, either increasing or decreasing transcription of specific genes, such as insulin-like growth factor I (IGF-1).

Androgen receptors can also have cytoplasmic activities though with signal transduction proteins in the cytoplasm. Androgen binding to cytoplasmic androgen receptors can cause rapid changes in cell function independent of gene transcription, for example ion transport, as well as indirect influence of gene transcription, for example via mediating other signal transduction pathways, thereby influencing the activity of other transcription factors.

The over-expression of androgen receptor, or expression of mutated androgen receptor genes has been indicated in several diseases, such as cancer, including prostate cancer and breast cancer, as well as other disorders such as polyglutamate disease (Monks et al., PNAS Nov. 2, 2007, published on line) alopecia, benign prostatic hyperplasia, spinal and muscular atrophy and Kennedy disease.

WO97/11170 reports on a method of treating a patient diagnosed as having benign prostatic hyperplasia or a prostate cancer comprising administering an antisense oligonucleotide which selectively hybridises to the androgen receptor mRNA. Three antisense oligonucleotide sequences of between 27-29 nucleotides are disclosed.

U.S. Pat. No. 6,733,776 and EP 0 692 972 report on a method for treating androgenic alopecia by applying liposomes comprising an antisense nucleic acid that hybridises to an androgen receptor gene. No antisense molecules with specific sequences and targeting the androgen receptor are provided.

US 2005/0164970 reports on a method of treating prostate cancer using siRNA complexes targeting the androgen receptor mRNA.

WO 2005/027833 reports on a method of treating prostate cancer comprising of administering a morpholino oligonucleotide of between 12-40 morpholino sub-units in length to the patient.

WO 2001/083740 reports on an antisense compound having an uncharged morpholino backbone of between 18 to 20 contiguous units which targets the human androgen receptor. Morpholino antisense compounds work via binding to the nucleic acid target to block access to the mRNA by other molecules, such as molecules involved in mRNA splicing or translation initiation.

U.S. Pat. No. 7,067,256 reports on a ribozyme which apparently mediates inactivation of the androgen receptor. A 19 nucleotide RNA molecule antisense to a corresponding region of the androgen receptor mRNA is provided.

However, despite the application of siRNA, morpholino antisense and ribozymes, none of the above androgen receptor inhibitors have been successful in efficiently down-regulating the androgen-receptor in vivo and at pharmacologically acceptable dosages.

U.S. Pat. No. 7,709,517 teaches diarylhydantoin compounds, including diarylthiohydantoins, which inhibit androgen receptor binding, methods for synthesizing the compounds and methods for using them in the treatment of hormone refractory prostate cancer.

What is needed and desirable are improved compositions and methods for the treatment of androgen receptor (AR) dependent medical disorders including AR-dependent cancers.

SUMMARY OF INVENTION

In an exemplary aspect, the present invention provides the use in combination of a new class of LNA antisense oligomer androgen receptor antagonists and diarylhydantoin androgen receptor binding inhibitors, such as 4-(3-(4-cyano-3-(trifluoromethyl)phenyl)-5,5-dimethyl-4-oxo-2-thioxoimidazolidin-1-yl)-2-fluoro-N-methylbenzamide ("MDV3100"), for the treatment of androgen receptor dependent medical disorders in mammals such as humans. The condition treated may, for example, be an androgen receptor-dependent cancer such as a breast cancer or a prostate cancer, for example, advanced prostate cancer, castration-resistant prostate cancer (CRPC), hormone refractory prostate cancer, alopecia, benign prostatic hyperplasia, spinal and muscular atrophy, Kennedy disease and polyglutamate disease. The present inventors have discovered that antisense oligomers targeting the androgen receptor strongly potentiate the effect of diarylhydantoin androgen receptor blockers.

One embodiment provides a method for treating a disease or a medical disorder as disclosed herein, such as a hyperproliferative disorder, such as cancer, said method comprising administering to a mammal in need of treatment for the disorder (1) an antisense oligomer, a conjugate or a pharmaceutical composition according to the invention, to a patient suffering from, or likely to suffer from said a disease or a medical disorder in an amount effective to decrease expression of AR and (2) a diarylhydantoin androgen receptor binding inhibitor, such as 4-(3-(4-cyano-3-(trifluoromethyl)phenyl)-5,5-dimethyl-4-oxo-2-thioxoimidazolidin-1-yl)-2-fluoro-N-methylbenzamide, in an amount effective to decrease the activity of AR in the mammal, such that the effect of the oligomer, conjugate thereof or composition is temporally overlapping with the effect of the diarylhydantoin AR inhibitor.

A related embodiment provides a method for decreasing AR activity in a cell, such as a mammalian cell, such as a human cell, said method comprising contacting the cell with (1) an antisense oligomer, a conjugate or a pharmaceutical composition according to the invention, to a patient suffering from, or likely to suffer from said a disease or a medical disorder in an amount effective to decrease expression of AR and (2) a diarylhydantoin androgen receptor binding inhibitor, such as 4-(3-(4-cyano-3-(trifluoromethyl)phenyl)-5,5-dimethyl-4-oxo-2-thioxoimidazolidin-1-yl)-2-fluoro-N-methylbenzamide, in an amount effective to decrease the activity of AR in the mammal, such that the effect of the oligomer, conjugate thereof or composition is temporally overlapping with the effect of the diarylhydantoin AR inhibitor.

The oligomer used may, for example, be between 10-50, such as 10-30 nucleotides in length which comprises a contiguous nucleotide sequence of a total of between 10-50, such as 10-30 nucleotides, wherein said contiguous nucleotide sequence is at least 80% (e.g., 85%, 90%, 95%, 98%, or 99%) homologous to a region corresponding to the reverse complement of a nucleic acid which encodes a mammalian androgen receptor, such as a mammalian Androgen Receptor gene or mRNA, such as SEQ ID NO: 1 or naturally occurring variants thereof. Thus, for example, the oligomer hybridizes to a single stranded nucleic acid molecule having the sequence of a (corresponding) portion of SEQ ID NO: 1.

The oligomer used may, for example, be between 10-50 nucleobases in length which comprises a contiguous nucleobase sequence of a total of between 10-50 nucleobases, wherein said contiguous nucleobase sequence is at least 80% homologous to a corresponding region of a nucleic acid which encodes a mammalian androgen receptor.

The oligomer used may, for example, be between 10-50 nucleobases in length which comprises a contiguous nucleobase sequence of a total of between 10-50 nucleobases, wherein said contiguous nucleobase sequence is at least 80% identical to the reverse complement of a target region of a nucleic acid which encodes a mammalian androgen receptor.

The oligomer used may, for example, consist of 10 to 30 contiguous monomers wherein adjacent monomers are covalently linked by a phosphate group or a phosphorothioate group, wherein said oligomer comprises a first region of at least 10 contiguous monomers; wherein at least one monomer of said first region is a nucleoside analogue; wherein the sequence of said first region is at least 80% identical to the reverse complement of the best-aligned target region of a mammalian androgen receptor gene or a mammalian androgen receptor mRNA.

In one preferred variation, an antisense oligomer selected from the group consisting of:

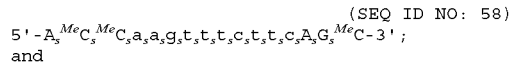
(SEQ ID NO: 58)

and

(SEQ ID NO: 77)

wherein uppercase letters denote beta-D-oxy-LNA monomers and lowercase letters denote DNA monomers, the subscript "s" denotes a phosphorothioate linkage, and $^{Me}C$ denotes a beta-D-oxy-LNA monomer containing a 5-methylcytosine base, or a conjugate thereof or a pharmaceutically acceptable salt of said compound or said conjugate, is used.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF FIGURES

FIG. 3. Sequence alignment of the human Androgen receptor mRNA sequence (GenBank Accession No.: NM_000044; SEQ ID NO: 1) and the mouse Androgen receptor mRNA sequence (GenBank Accession No.: NM_013476; SEQ ID NO: 81)

FIG. 4. Location of preferred target regions of the human AR mRNA (cDNA; SEQ ID NO: 1) targeted by oligomers according to the invention. Although 16mer target sites have been shown, in some embodiments, these target regions may comprise an additional 4 bases 5' or 3' to the regions shown—i.e. are target regions of up to 24 contiguous nucleotides.

Figure 5A:
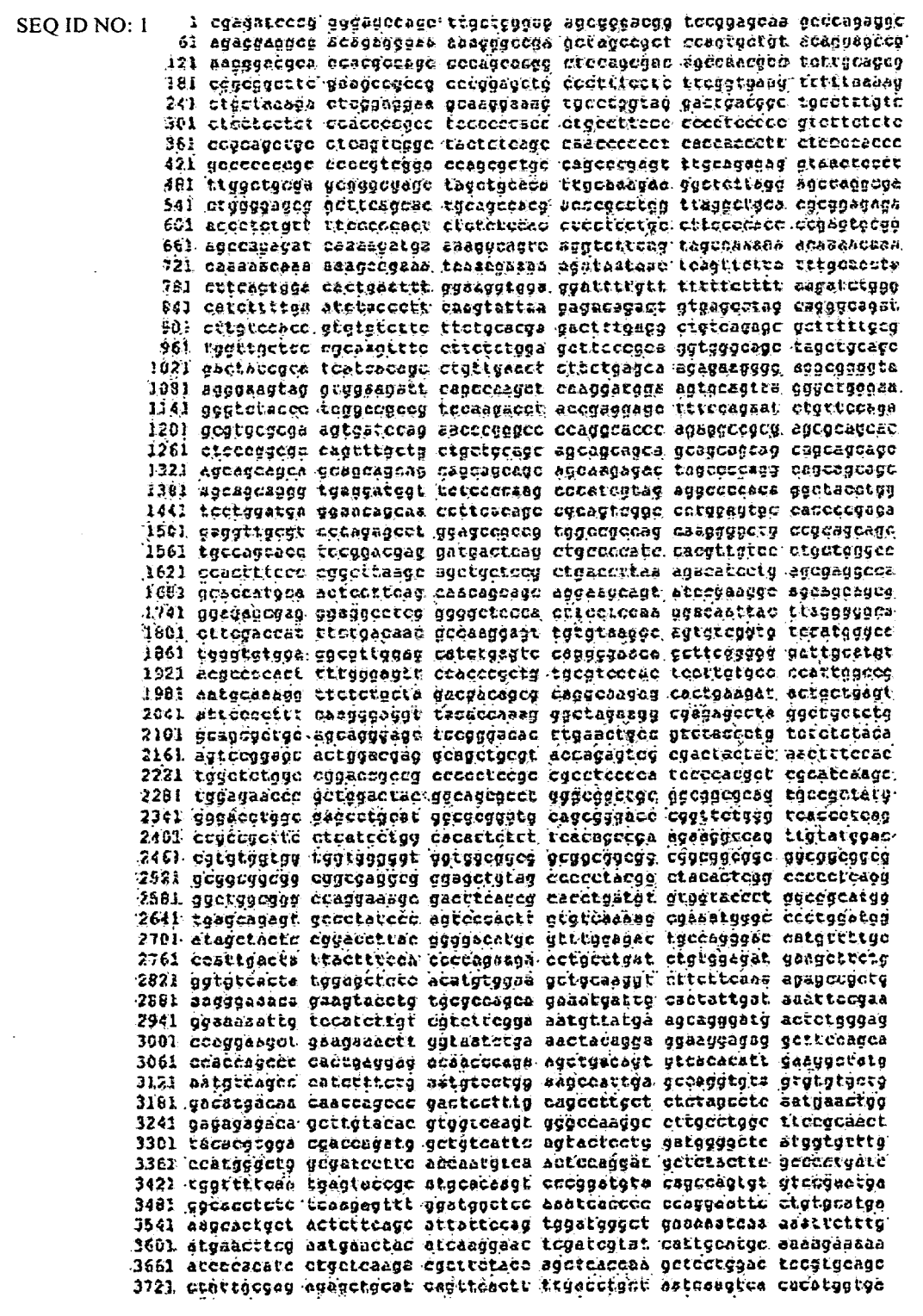
Figure 5B:
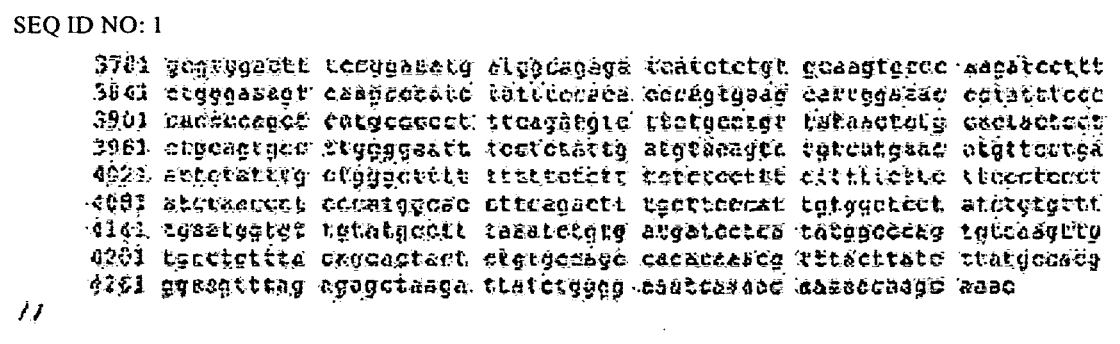

FIG. 5. SEQ ID NO:1 *Homo sapiens* androgen receptor (dihydrotestosterone receptor; testicular feminization; spinal and bulbar muscular atrophy; Kennedy disease) (AR), transcript variant 1, mRNA. (Genbank Accession number NM_000044).

FIG. 6. SEQ ID NO 81: Mouse androgen receptor mRNA sequence.

FIG. 7. SEQ ID NO 82: Rhesus monkey androgen receptor mRNA sequence.

FIG. 8. SEQ ID NO 83: *Homo sapiens* androgen receptor protein amino acid sequence.

FIG. 9. SEQ ID NO 84: Mouse androgen receptor protein amino acid sequence.

FIG. 10. SEQ ID NO 85: Rhesus monkey androgen receptor protein amino acid sequence.

DETAILED DESCRIPTION OF INVENTION

The Oligomer

Figure 1:
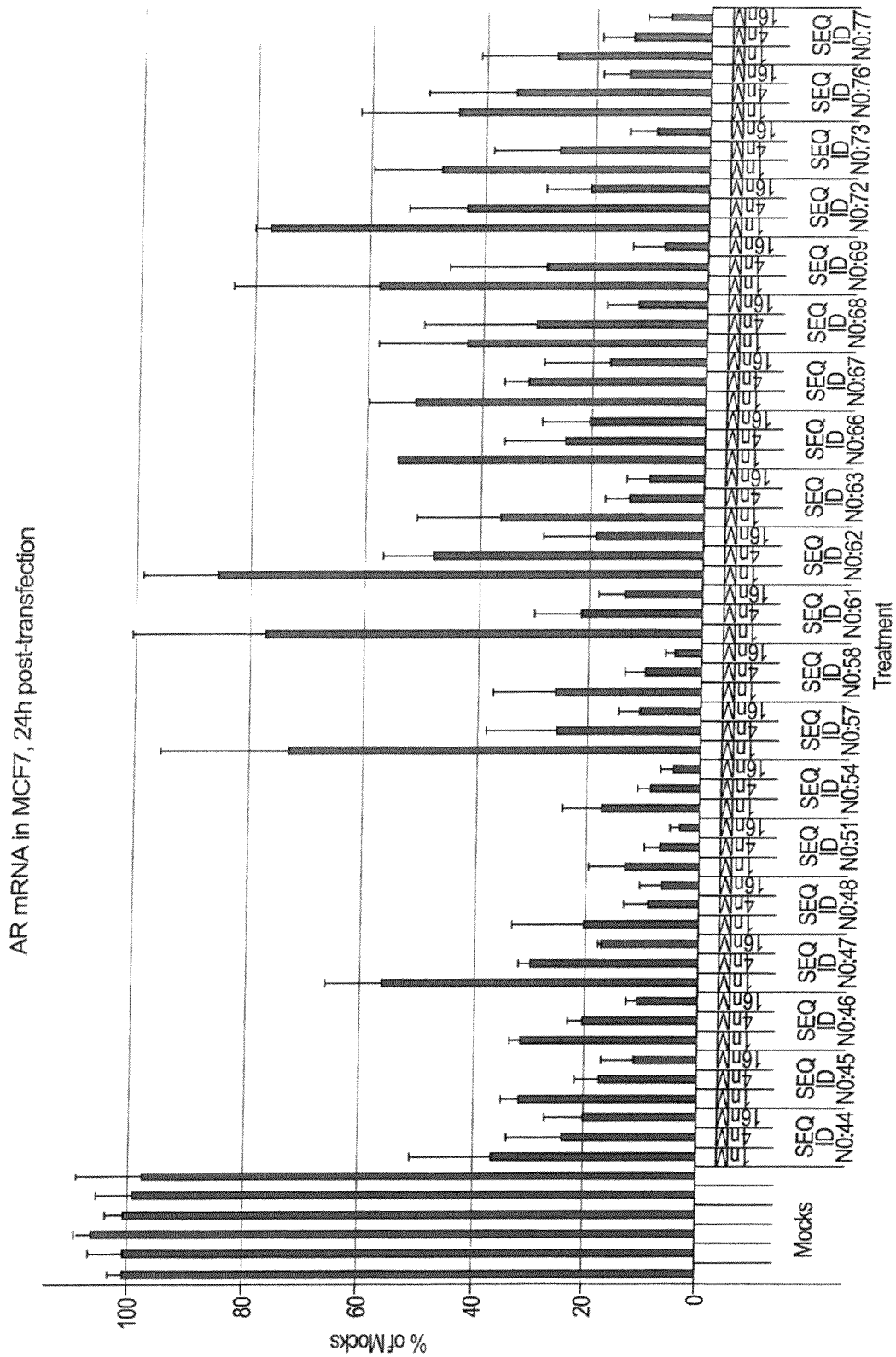
FIG. 1. Oligonucleotides presented in Table 3 were evaluated for their potential to knockdown the androgen receptor mRNA at concentrations of 1, 4 and 16 nM in MCF7 cells 24 hours after transfection using Real-time PCR. All results were normalised to GAPDH and inhibition of AR mRNA is shown as percent of untreated control. Results shown are an average of three independent experiments.

The present invention employs oligomeric compounds (referred herein as oligomers), for use in modulating the function of nucleic acid molecules encoding mammalian Androgen Receptor, such as the Androgen Receptor nucleic acid shown in SEQ ID NO 1, and naturally occurring variants of such nucleic acid molecules encoding mammalian Androgen Receptor. The term "oligomer" in the context of the present invention, refers to a molecule formed by covalent linkage of two or more nucleotides (i.e. an oligonucleotide). Herein, each single nucleotide, such as the nucleotides present in the oligomer of the invention, may also be referred to as a "monomer" or "unit". In some embodiments, the oligomer consists or comprises of a contiguous nucleotide sequence of between 10-30 nucleotides in length (i.e. comprises or consists of from 10-30 covalently linked monomers).

In various embodiments, the antisense oligomer targeting the androgen receptor does not comprise RNA (units). In various embodiments, the antisense oligomers according to the invention are linear molecules or are synthesised as a linear molecule. The oligomer, in such embodiments, is a single stranded molecule, and typically does not comprise short regions of, for example, at least 3, 4 or 5 contiguous nucleotides, which are complementary to another region within the same oligomer (i.e. duplexes) In this regards, in some embodiments, the oligomer is not (essentially) double stranded. In some embodiments, the oligomer is essentially not double stranded, such as is not a siRNA. In various embodiments, the oligomer of the invention may consist entirely of the contiguous nucleotide region. Thus, the oligomer is not substantially self-complementary. siRNAs comprise of 2 complementary short RNA (or equivalent nucleobase units) sequences, such as between 21 and 23 nts long, with, typically a 2 nt 3' overhang on either end. In order to enhance in vivo uptake, the siRNAs may be conjugated, such as conjugated to a sterol, such as a cholesterol group (typically at the 3' or 5' termini of one or both of the strands).

Figure 4B:
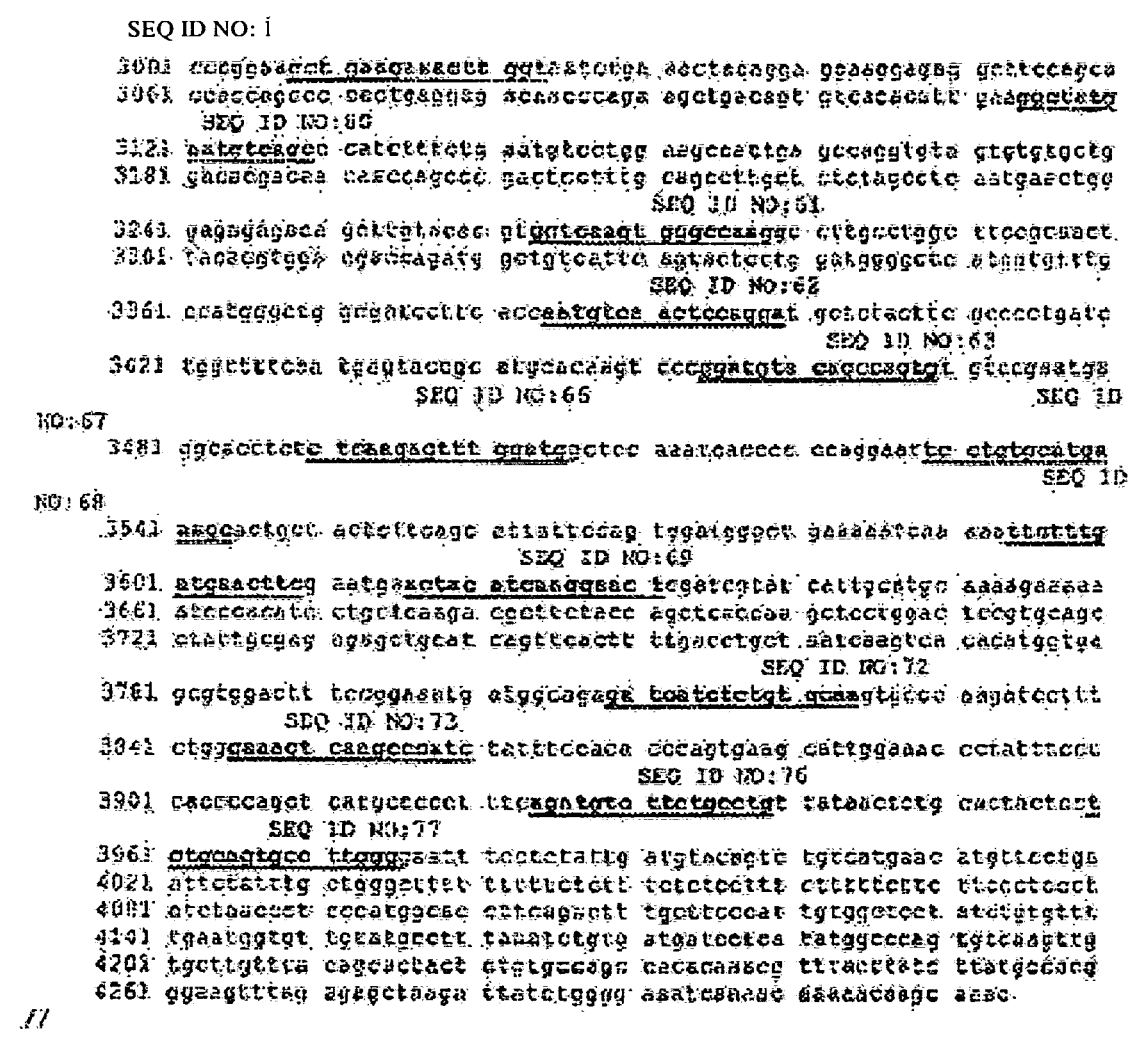

The invention further provides target sequences in the AR mRNA or gene, or an allelic variant thereof, in particular those corresponding to SEQ ID NOS: 2-22, wherein antisense oligonucleotides corresponding to said target sequences are capable of down-regulating AR. For example, target sequences which correspond to the antisense oligonucleotide sequences SEQ ID NOS: 2-22, respectively, are shown in FIG. 4 (bold and underlined, with the corresponding oligo SEQ ID NOS indicated above). Variant sequences, for example but not limited to allelic variants (such as a (AR) gene present at gene locus Xq11-12) of such target sequences are also within the scope of the invention. A variant sequence may have at least 60%, more preferably at least 70%, more preferably at least 80%, more preferably at least 85%, more preferably at least 90%, more preferably at least 91%, at least 92%, at least 93%, at least 94%, at least 95% sequence homology to a target sequence in AR. Typically, an oligomer of the invention corresponding to said variant sequences is still capable of down-regulating AR.

Specific designs of LNA oligonucleotides are also disclosed, for example those shown in SEQ ID NOS 44-80. The oligomers of the invention are considered to be potent inhibitors of androgen receptor mRNA and protein expression.

The Target

The mammalian androgen receptor is preferably selected from the group consisting of human or mouse androgen receptor. Preferably the mammalian androgen receptor is human androgen receptor, such as the Androgen receptor encoded by the nucleic acid as shown in SEQ ID NO 1. Further mammalian androgen receptor genes (targets) and their corresponding proteins are shown in the following table:

|  | Genbank Accession Numbers-Nucleic acid (mRNA/cDNA sequence) | Genbank Accession Numbers-Polypeptide (deduced) |
| --- | --- | --- |
| Human | NM_000044 | NP_000035 |
| Mouse | NM_013476 | NP_038504 |
| Rhesus monkey | NM_001032911 | NP_001028083 |

It should be recognised that the Androgen Receptor gene in humans does show a degree of allelic variation, and several of the polymorphisms are recognized. The above-disclosed GenBank Accession numbers for nucleic acids refer to cDNA sequences and not to mRNA sequences per se. The sequence of a mature mRNA can be derived directly from the corresponding cDNA sequence with thymine bases (T) being replaced by uracil bases (U).

It should be recognised that the Androgen Receptor gene in humans does show a degree of allelic variation, and several of the polymorphisms are associated with disease phenotypes (Mooney et al, NAR 15; 31(8) 2003). For example, a CAG repeat expansion is associated with polyglutamine expansion disorder, other characterised allelic variants include a (GGC)n trinucleotide repeat and R726L, T887A and L710H single nucleotide polymorphisms have been identified, and the latter two have been shown to be correlated to enhanced promiscuity of the AR receptor for other steroid ligands. In one embodiment n may range from between 5 and 31. CAG repeats of less than 22 have been associated with an enhanced risk of prostate cancer in African American males, and this may therefore be a preferred allelic variant.

In some embodiments, the target nucleic acid is an AR allelic variant which comprises one or more single nucleotide polymorphisms, including R726L, T887A and L710H.

Therefore, in some embodiments, the target is an AR allelic variant which comprises a (CAG)n trinucleotide repeat, or (GGC)n trinucleotide repeat.

The nucleic acid which encodes the mammalian androgen receptor is, in a preferable embodiment, the human androgen receptor cDNA sequence is shown as SEQ ID NO 1 and/or the mouse androgen receptor cDNA sequence is shown as SEQ ID NO 81, or allelic variants thereof. The oligomer according to the invention is an antisense oligonucleotide.

Therefore, 'the target' of the oligomer according to the invention is the androgen receptor mRNA. The oligomer when introduced into the cell which is expressing the androgen receptor gene, results in reduction of the androgen receptor mRNA level, resulting in reduction in the level of expression of the androgen receptor in the cell.

The androgen receptor is known to regulate the expression of several genes, such as a gene selected from the group consisting of Protein kinase C delta (PRKCD), Glutathione S-transferase theta 2 (GSTT2), transient receptor potential cation channel subfamily V member 3 (TRPV3), Pyrroline-5-carboxylate reductase 1 (PYCR1) or ornithine aminotransferase (OAT)—such genes are referred to as androgen receptor targets herein, and as such, in some embodiments, the oligomers according to the invention may be used to modulate the expression of one or more androgen receptor targets in a cell which is expressing, or is capable of expressing (i.e. in the case of alleviation of repression (by the AR) of the androgen receptor target in a cell) said androgen receptor target.

The oligomers which target the androgen receptor mRNA, may hybridize to any site along the target mRNA nucleic acid, such as the 5' untranslated leader, exons, introns and 3' untranslated tail. However, it is preferred that the oligomers which target the androgen receptor mRNA hybridise to the mature mRNA form of the target nucleic acid.

Suitably the oligomer of the invention is capable of down-regulating expression of the Androgen Receptor gene. In this regards, the oligomer of the invention can effect the inhibition of Androgen Receptor, typically in a mammalian such as a human cell. In some embodiments, the oligomers of the invention bind to the target nucleic acid and effect inhibition of expression of at least 10% or 20% compared to the normal expression level, more preferably at least a 30%, 40%, 50%, 60%, 70%, 80%, 90% or 95% inhibition as compared to the normal expression level (such as immediately prior to dosing of the oligomer). In some embodiments, such modulation is seen when using between 0.04 and 25 nM, such as between 0.8 and 20 nM concentration of the compound of the invention. In the same or a different embodiment, the inhibition of expression is less than 100%, such as less than 98% inhibition, less than 95% inhibition, less than 90% inhibition, less than 80% inhibition, such as less than 70% inhibition. Modulation of expression level may be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR. When measuring via mRNA levels, the level of down-regulation when using an appropriate dosage, such as between 0.04 and 25 nM, such as between 0.8 and 20 nM concentration, is, in some embodiments, typically to a level of between 10-20% the normal levels in the absence of the compound of the invention.

The invention therefore provides a method of down-regulating or inhibiting the expression of the androgen receptor protein and/or mRNA in a cell which is expressing the androgen receptor protein and/or mRNA, said method comprising administering or contacting the oligomer or conjugate according to the invention (suitably in an effective amount) to said cell to down-regulating or inhibiting the expression of the androgen receptor protein and/or mRNA in said cell. Suitably the cell is a mammalian cell such as a human cell. The administration or contacting may occur, in some embodiments, in vitro. The administration or contacting may occur, in some embodiments, in vivo.

The term "target nucleic acid", as used herein refers to the DNA or RNA encoding mammalian androgen receptor polypeptide, such as human androgen receptor, such as SEQ ID NO: 1. Androgen receptor encoding nucleic acids or naturally occurring variants thereof, and RNA nucleic acids derived therefrom, preferably mRNA, such as pre-mRNA, although preferably mature mRNA. In some embodiments, for example when used in research or diagnostics the "target nucleic acid" may be a cDNA or a synthetic oligonucleotide derived from the above DNA or RNA nucleic acid targets. The oligomer according to the invention is preferably capable of hybridising to the target nucleic acid. It will be recognised that SEQ ID NO: 1 is a cDNA sequences, and as such, corresponds to the mature mRNA target sequence, although uracil is replaced with thymidine in the cDNA sequences.

The term "naturally occurring variant thereof" refers to variants of the androgen receptor polypeptide of nucleic acid sequence which exist naturally within the defined taxonomic group, such as mammalian, such as mouse, monkey, and preferably human. Typically, when referring to "naturally occurring variants" of a polynucleotide the term also may encompass any allelic variant of the androgen receptor encoding genomic DNA which are found at the Chromosome X: 66.68-66.87 Mb by chromosomal translocation or duplication, and the RNA, such as mRNA derived therefrom. "Naturally occurring variants" may also include variants derived from alternative splicing of the androgen receptor mRNA. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc.

Oligomer Sequences

The oligomers comprise or consist of a contiguous nucleotide sequence which corresponds to the reverse complement of a nucleotide sequence present in SEQ ID NO: 1. Thus, the oligomer can comprise or consist of, or a sequence selected from the group consisting of SEQ ID NOS: 2-22 and 86-106, wherein said oligomer (or contiguous nucleotide portion thereof) may optionally have one, two, or three mismatches against said selected sequence.

The oligomer may comprise or consist of a contiguous nucleotide sequence which is fully complementary (perfectly complementary) to the equivalent region of a nucleic acid which encodes a mammalian androgen receptor (e.g., SEQ ID NO: 1). Thus, the oligomer can comprise or consist of an antisense nucleotide sequence.

However, in some embodiments, the oligomer may tolerate 1, 2, 3, or 4 (or more) mismatches, when hybridising to the target sequence and still sufficiently bind to the target to show the desired effect, i.e. down-regulation of the target. Mismatches may, for example, be compensated by increased length of the oligomer nucleotide sequence and/or an increased number of nucleotide analogues, such as LNA, present within the nucleotide sequence.

In some embodiments, the contiguous nucleotide sequence comprises no more than 3, such as no more than 2 mismatches when hybridizing to the target sequence, such as to the corresponding region of a nucleic acid which encodes a mammalian androgen receptor.

In some embodiments, the contiguous nucleotide sequence comprises no more than a single mismatch when hybridizing to the target sequence, such as the corresponding region of a nucleic acid which encodes a mammalian androgen receptor.

The nucleotide sequence of the oligomers of the invention or the contiguous nucleotide sequence is preferably at least 80% homologous to a corresponding sequence selected from the group consisting of SEQ ID NOS: 2-22 and 86-106, such as at least 85%, at least 90%, at least 91%, at least 92%, at least 93%, at least 94%, at least 95%, at least 96% homologous, such as 100% homologous (identical).

The nucleotide sequence of the oligomers of the invention or the contiguous nucleotide sequence is preferably at least 80% homologous to the reverse complement of a corresponding sequence present in SEQ ID NO: 1, such as at least 85%, at least 90%, at least 91%, at least 92% at least 93%, at least 94%, at least 95%, at least 96% homologous, at least 97% homologous, at least 98% homologous, at least 99% homologous, such as 100% homologous (identical).

The nucleotide sequence of the oligomers of the invention or the contiguous nucleotide sequence is preferably at least 80% complementary to a sub-sequence present in SEQ ID NO: 1, such as at least 85%, at least 90%, at least 91%, at least 92%, at least 93%, at least 94%, at least 95%, at least 96% complementary, at least 97% complementary, at least 98% complementary, at least 99% complementary, such as 100% complementary (perfectly complementary).

In some embodiments, the oligomer (or contiguous nucleotide portion thereof) is selected from, or comprises, one of the sequences selected from the group consisting of SEQ ID NOS: 2, 3, 4, 5, 6, 7, 8, 9, 10, 11, 12, 13, 14, 15, 16, 17, 18, 19, 20, 21, and 22, or a sub-sequence of at least 10 contiguous nucleotides thereof, wherein said oligomer (or contiguous nucleotide portion thereof) may optionally comprise one, two, or three mismatches when compared to the sequence.

In some embodiments, the oligomer (or contiguous nucleotide portion thereof) is selected from, or comprises, one of the sequences selected from the group consisting of SEQ ID NOS: 86, 87, 88, 89, 90, 91, 92, 93, 94, 95, 96, 97, 98, 99, 100, 101, 102, 103, 104, 105 and 106, or a sub-sequence of at least 10 contiguous nucleotides thereof, wherein said oligomer (or contiguous nucleotide portion thereof) may optionally comprise one, two, or three mismatches when compared to the sequence.

Other preferred oligomers include a (contiguous) nucleotide sequence, such as a sequence of 12, 13, 14, 15 or 16 contiguous nucleotides in length, which have a nucleotide sequence selected from a sequence from the group consisting of SEQ ID No 2, 3, 4, 5, 6, 7, 8, 9, 10, 11, 12, 13, 14, 15, 16, 17, 18, 19, 20, 21, and 22, wherein said oligomer (or contiguous nucleotide portion thereof) may optionally comprise one, two, or three mismatches against said selected sequence.

In some embodiments, the sub-sequence may consist of 11, 12, 13, 14, 15, 16, 17, 18, 19, 20, 21, 22, 23, 24, 25, 26, 27, 28, or 29 contiguous nucleotides, such as between 12-22, such as between 12-18 nucleotides. Suitably, in some embodiments, the sub-sequence is of the same length as the contiguous nucleotide sequence of the oligomer of the invention.

However, it is recognised that, in some embodiments the nucleotide sequence of the oligomer may comprise additional 5' or 3' nucleotides, such as, independently, 1, 2, 3, 4 or 5 additional nucleotides 5' and/or 3', which are non-complementary to the target sequence. In this respect the oligomer of the invention, may, in some embodiments, comprise a contiguous nucleotide sequence which is flanked 5' and or 3' by additional nucleotides. In some embodiments the additional 5' or 3' nucleotides are naturally occurring nucleotides, such as DNA or RNA. In some embodiments, the additional 5' or 3' nucleotides may represent region D as referred to in the context of gapmer oligomers herein.

In some embodiments, the oligomer according to the invention consists or comprises of a nucleotide sequence according to SEQ ID NO 2, such as SEQ ID NO 44, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 3, such as SEQ ID 45, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 4, such as SEQ ID NO 46, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 5, such as SEQ ID NO 47, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 6, such as SEQ ID NO 48, 49 or 50, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 7, such as SEQ ID NO 51, 52, or 53, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 8, such as SEQ ID 54, 55 or 56, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 9, such as SEQ ID 57, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 10, such as SEQ ID 58, 59, or 60, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 11, such as SEQ ID 61, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 12, such as SEQ ID 62, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 13, such as SEQ ID 63, 64 or 65 or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 14, such as SEQ ID 66, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 15, such as SEQ ID 67, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 16, such as SEQ ID 68, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 17, such as SEQ ID 69, 70 or 71, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 18, such as SEQ ID 72, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 19, such as SEQ ID 73, 74 or 75, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 20, such as SEQ ID 76, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 21, such as SEQ ID 77, 78 or 79, or a sub-sequence of at least 10 contiguous nucleotides thereof, such as 11, 12, 13, 14, 15 or 16 contiguous nucleotides thereof.

In some embodiments, the oligomer according to the invention consists or comprises of a nucleotide sequence according to SEQ ID 22, such as SEQ ID 80, or a sub-sequence of at least 10 contiguous nucleotides thereof, such as 11, 12, 13, 14, 15 or 16 contiguous nucleotides thereof.

When determining "homology" between the oligomers of the invention (or contiguous nucleotide sequence) and the nucleic acid which encodes the mammalian androgen receptor or the reverse complement thereof, such as those disclosed herein, the determination of homology may be made by a simple alignment with the corresponding nucleotide sequence of the compound of the invention and the corresponding region of the nucleic acid which encodes the mammalian androgen receptor (or target nucleic acid), or the reverse complement thereof, and the homology is determined by counting the number of bases which align and dividing by the total number of contiguous nucleotides in the compound of the invention, and multiplying by 100. In such a comparison, if gaps exist, it is preferable that such gaps are merely mismatches rather than areas where the number of nucleotides within the gap differ between the nucleotide sequence of the invention and the target nucleic acid.

The terms "corresponding to" and "corresponds to" refer to the comparison between the nucleotide sequence of the oligomer or contiguous nucleotide sequence (a first sequence) and the equivalent contiguous nucleotide sequence of a further sequence selected from either i) a sub-sequence of the reverse complement of the nucleic acid target, such as the mRNA which encodes the androgen receptor protein, such as SEQ ID NO: 1, and/or ii) the sequence of nucleotides provided herein such as the group consisting of SEQ ID NOS: 2-22 and 86-106, or sub-sequence thereof. Nucleotide analogues are compared directly to their equivalent or corresponding nucleotides. A first sequence which corresponds to a further sequence under i) or ii) typically is identical to that sequence over the length of the first sequence (such as the contiguous nucleotide sequence) or, as described herein may, in some embodiments, is at least 80% homologous to a corresponding sequence, such as at least 85%, at least 90%, at least 91%, at least 92% at least 93%, at least 94%, at least 95%, at least 96% homologous, at least 97% homologous, at least 98% homologous, at least 99% homologous, such as 100% homologous (identical).

The terms "corresponding nucleotide analogue" and "corresponding nucleotide" are intended to indicate that the nucleotide in the nucleotide analogue and the naturally occurring nucleotide are identical. For example, when the 2-deoxyribose unit of the nucleotide is linked to an adenine, the "corresponding nucleotide analogue" contains a pentose unit (different from 2-deoxyribose) linked to an adenine.

Oligomer Length

The oligomers comprise or consist of a contiguous nucleotide sequence of a total of between 10, 11, 12, 13, 14, 15, 16, 17, 18, 19, 20, 21, 22, 23, 24, 25, 26, 27, 28, 29 or 30 contiguous nucleotides in length.

In some embodiments, the oligomers comprise or consist of a contiguous nucleotide sequence of a total of between 10-22, such as 12-18, such as 13-17 or 12-16, such as 13, 14, 15, 16 contiguous nucleotides in length.

In some embodiments, the oligomers comprise or consist of a contiguous nucleotide sequence of a total of 10, 11, 12, 13, or 14 contiguous nucleotides in length.

In some embodiments, the oligomer according to the invention consists of no more than 22 nucleotides, such as no more than 20 nucleotides, such as no more than 18 nucleotides, such as 15, 16 or 17 nucleotides. In some embodiments the oligomer of the invention comprises less than 20 nucleotides.

Nucleotide Analogues

The term "nucleotide" as used herein, refers to a glycoside comprising a sugar moiety, a base moiety and a covalently linked phosphate group and covers both naturally occurring nucleotides, such as DNA or RNA, preferably DNA, and non-naturally occurring nucleotides comprising modified sugar and/or base moieties, which are also referred to as "nucleotide analogues" herein.

Non-naturally occurring nucleotides include nucleotides which have modified sugar moieties, such as bicyclic nucleotides or 2' modified nucleotides, such as 2' substituted nucleotides.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligonucleotide, i.e. have no functional effect on the way the oligonucleotide works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity to the target and/or increased resistance to intracellular nucleases and/or increased ease of transport into the cell. Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1:

Scheme 1

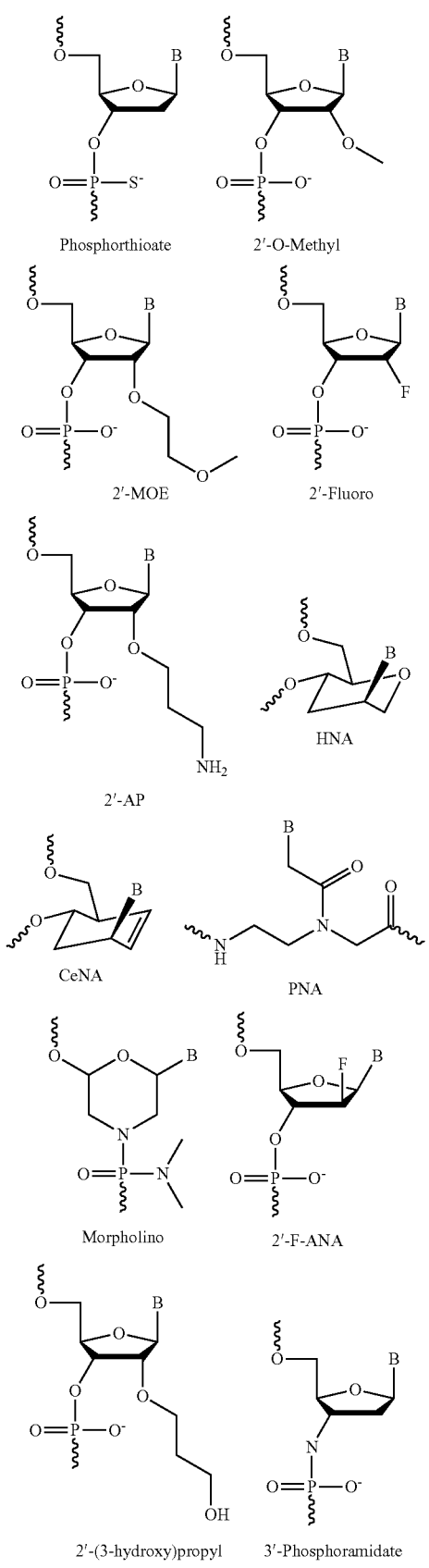

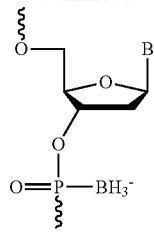

Boranophosphates

The oligomer may thus comprise or consist of a simple sequence of natural occurring nucleotides—preferably 2'-deoxynucleotides (referred to here generally as "DNA"), but also possibly ribonucleotides (referred to here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Examples of suitable and preferred nucleotide analogues are provided by International Pub. No. WO2007/031091 (PCT/DK2006/000512) or are referenced therein.

Incorporation of affinity-enhancing nucleotide analogues in the oligomer, such as LNA or 2'-substituted sugars, can allow the size of the specifically binding oligomer to be reduced, and may also reduce the upper limit to the size of the oligomer before non-specific or aberrant binding takes place.

In some embodiments the oligomer comprises at least 2 nucleotide analogues. In some embodiments, the oligomer comprises from 3-8 nucleotide analogues, e.g. 6 or 7 nucleotide analogues. In the by far most preferred embodiments, at least one of said nucleotide analogues is a locked nucleic acid (LNA); for example at least 3 or at least 4, or at least 5, or at least 6, or at least 7, or 8, of the nucleotide analogues may be LNA. In some embodiments all the nucleotides analogues may be LNA.

It will be recognised that when referring to a preferred nucleotide sequence motif or nucleotide sequence, which consists of only nucleotides, the oligomers of the invention which are defined by that sequence may comprise a corresponding nucleotide analogue in place of one or more of the nucleotides present in said sequence, such as LNA units or other nucleotide analogues, which raise the duplex stability/ $T_m$ of the oligomer/target duplex (i.e. affinity enhancing nucleotide analogues).

In some embodiments, any mismatches between the nucleotide sequence of the oligomer and the target sequence are preferably found in regions outside the affinity enhancing nucleotide analogues, such as region B as referred to herein, and/or region D as referred to herein, and/or at the site of non modified such as DNA nucleotides in the oligonucleotide, and/or in regions which are 5' or 3' to the contiguous nucleotide sequence.

Examples of such modification of the nucleotide include modifying the sugar moiety to provide a 2'-substituent group or to produce a bridged (locked nucleic acid) structure which enhances binding affinity and may also provide increased nuclease resistance.

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments the nucleotide analogues present within the oligomer of the invention (such as in regions A and C mentioned herein) are independently selected from, for example: 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'MOE units. In some embodiments there is only one of the above types of nucleotide analogues present in the oligomer of the invention, or contiguous nucleotide sequence thereof.

In some embodiments the nucleotide analogues are 2'-O-methoxyethyl-RNA (2'MOE), 2'-fluoro-DNA monomers or LNA nucleotide analogues, and as such the oligonucleotide of the invention may comprise nucleotide analogues which are independently selected from these three types of analogue, or may comprise only one type of analogue selected from the three types. In some embodiments at least one of said nucleotide analogues is 2'-MOE-RNA, such as 2, 3, 4, 5, 6, 7, 8, 9 or 10 2'-MOE-RNA nucleotide units. In some embodiments at least one of said nucleotide analogues is 2'-fluoro DNA, such as 2, 3, 4, 5, 6, 7, 8, 9 or 10 2'-fluoro-DNA nucleotide units.

In some embodiments, the oligomer according to the invention comprises at least one Locked Nucleic Acid (LNA) unit, such as 1, 2, 3, 4, 5, 6, 7, or 8 LNA units, such as between 3-7 or 4 to 8 LNA units, or 3, 4, 5, 6 or 7 LNA units. In some embodiments, all the nucleotide analogues are LNA. In some embodiments, the oligomer may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5' methyl-Cytosine. In some embodiments of the invention, the oligomer may comprise both LNA and DNA units. Preferably the combined total of LNA and DNA units is 10-25, preferably 10-20, even more preferably 12-16. In some embodiments of the invention, the nucleotide sequence of the oligomer, such as the contiguous nucleotide sequence consists of at least one LNA and the remaining nucleotide units are DNA units. In some embodiments the oligomer comprises only LNA nucleotide analogues and naturally occurring nucleotides (such as RNA or DNA, most preferably DNA nucleotides), optionally with modified internucleotide linkages such as phosphorothioate.

The term "nucleobase" refers to the base moiety of a nucleotide and covers both naturally occurring a well as non-naturally occurring variants. Thus, "nucleobase" covers not only the known purine and pyrimidine heterocycles but also heterocyclic analogues and tautomeres thereof.

Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments, at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA" refers to a bicyclic nucleotide analogue, known as "Locked Nucleic Acid". It may refer to an LNA monomer, or, when used in the context of an "LNA oligonucleotide" refers to an oligonucleotide containing one or more such bicyclic nucleotide analogues.

The LNA used in the oligonucleotide compounds of the invention preferably has the structure of the general formula I

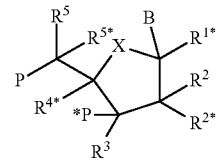

wherein X is selected from —O—, —S—, —N($R^{N*}$)—, —C($R^6R^{6*}$)—;

B is selected from hydrogen, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$ or equally applicable the substituent $R^{5*}$;

P* designates an internucleoside linkage to a preceding monomer, or a 3'-terminal group;

$R^{4*}$ and $R^{2*}$ together designate a biradical consisting of 1-4 groups/atoms selected from —C($R^aR^b$)—, —C($R^a$)=C ($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$), and each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1-5 carbon atom(s) alkylene chain which is optionally interrupted and/or terminated by one or more heteroatoms/groups selected from —O—, —S—, and —(NR$^N$)— where R$^N$ is selected from hydrogen and C$_{1-4}$-alkyl, and where two adjacent (non-geminal) substituents may designate an additional bond resulting in a double bond; and R$^{N*}$, when present and not involved in a biradical, is selected from hydrogen and C$_{1-4}$-alkyl; and basic salts and acid addition salts thereof;

In some embodiments R$^{5*}$ is selected from H, —CH$_3$, —CH$_2$—CH$_3$, —CH$_2$—O—CH$_3$, and —CH═CH$_2$.

In some embodiments, R$^{4*}$ and R$^{2*}$ together designate a biradical selected from —C(R$^a$R$^b$)—O—, —C(R$^a$R$^b$)—C(R$^c$R$^d$)—O—, —C(R$^a$R$^b$)—C(R$^c$R$^d$)—C(R$^e$R$^f$)—O—, —C(R$^a$R$^b$)—O—C(R$^c$R$^d$)—, —C(R$^a$R$^b$)—O—C(R$^c$R$^d$)—O—, —C(R$^a$R$^b$)—C(R$^c$R$^d$)—, —C(R$^a$R$^b$)—C(R$^c$R$^d$)—C(R$^e$R$^f$)—, —C(R$^a$)═C(R$^b$)—C(R$^c$R$^d$)—, —C(R$^a$R$^b$)—N(R$^c$)—, —C(R$^a$R$^b$)—C(R$^c$R$^d$)—N(R$^e$)—, —C(R$^a$R$^b$)—N(R$^c$)—O—, and —C(R$^a$R$^b$)—S—, —C(R$^a$R$^b$)—C(R$^c$R$^d$)—S—, wherein R$^a$, R$^b$, R$^c$, R$^d$, R$^e$, and R$^f$ each is independently selected from hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkyl-sulphonyloxy, nitro, azido, sulphanyl, C$_{1-6}$-alkylthio, halogen, DNA intercalators, photochemically active groups, thermochemically active groups, chelating groups, reporter groups, and ligands, where aryl and heteroaryl may be optionally substituted and where two geminal substituents R$^a$ and R$^b$ together may designate optionally substituted methylene (═CH$_2$), In a further embodiment R$^{4*}$ and R$^{2*}$ together designate a biradical (bivalent group) selected from —CH$_2$—O—, —CH$_2$—S—, —CH$_2$—NH—, —CH$_2$—N(CH$_3$)—, —CH$_2$—CH$_2$—O—, —CH$_2$—CH(CH$_3$)—, —CH$_2$—CH$_2$—S—, —CH$_2$—CH$_2$—NH—, —CH$_2$—CH$_2$—CH$_2$—, —CH$_2$—CH$_2$—CH$_2$—O—, —CH$_2$—CH$_2$—CH(CH$_3$)—, —CH═CH—CH$_2$—, —CH$_2$—O—CH$_2$—O—, —CH$_2$—NH—O—, —CH$_2$—N(CH$_3$)—O—, —CH$_2$—O—CH$_2$—, —CH(CH$_3$)—O—, —CH(CH$_2$—O—CH$_3$)—O—.

For all chiral centers, asymmetric groups may be found in either R or S orientation.

Preferably, the LNA used in the oligomer of the invention comprises at least one LNA unit according to any of the formulas

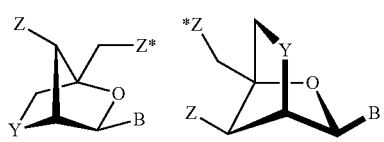

wherein Y is —O—, —O—CH$_2$—, —S—, —NH—, or N(R$^H$); Z and Z* are independently selected among an internucleotide linkage, a terminal group or a protecting group; B constitutes a natural or non-natural nucleotide base moiety, and R$^H$ is selected from hydrogen and C$_{1-4}$-alkyl.

Specifically preferred LNA units are shown in scheme 2:

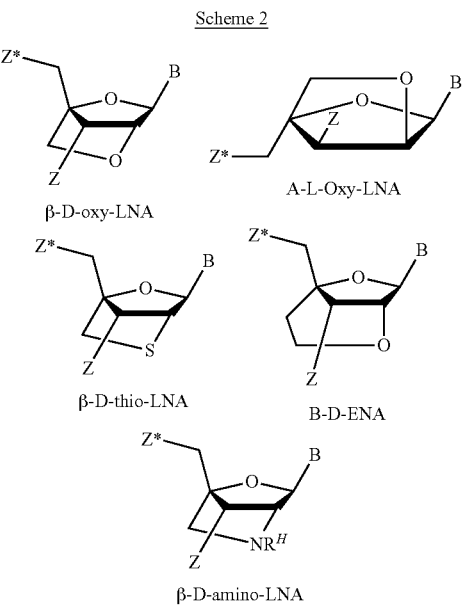

The term "thio-LNA" comprises a locked nucleotide in which Y in the general formula above is selected from S or —CH$_2$—S—. Thio-LNA can be in either the beta-D and alpha-L-configuration.

The term "amino-LNA" refers to a locked nucleotide in which Y in the general formula above is selected from —N(H)—, N(R)—, CH$_2$—N(H)—, and —CH$_2$—N(R)— where R is selected from hydrogen and C$_{1-4}$-alkyl. Amino-LNA can be in either the beta-D and alpha-L-configuration.

The term "oxy-LNA" refers to a locked nucleotide in which Y in the general formula above represents —O— or —CH$_2$—O—. Oxy-LNA can be in either the beta-D and alpha-L-configuration.

The term "ENA" refers to a locked nucleotide in which Y in the general formula above is —CH$_2$—O— (where the oxygen atom of —CH$_2$—O— is attached to the 2'-position relative to the base B).

In a preferred embodiment LNA is selected from beta-D-oxy-LNA, alpha-L-oxy-LNA, beta-D-amino-LNA and beta-D-thio-LNA, in particular beta-D-oxy-LNA.

RNAse Recruitment

It is recognised that an oligomeric compound may function via non RNase mediated degradation of target mRNA, such as by steric hindrance of translation, or other methods, however, the preferred oligomers of the invention are capable of recruiting an endoribonuclease (RNase), such as RNase H.

It is preferable that the oligomer, or contiguous nucleotide sequence, comprises of a region of at least 6, such as at least 7 consecutive nucleotide units, such as at least 8 or at least 9 consecutive nucleotide units (residues), including 7, 8, 9, 10, 11, 12, 13, 14, 15 or 16 consecutive nucleotides, which, when formed in a duplex with the complementary target RNA is capable of recruiting RNase. The contiguous sequence which is capable of recruiting RNAse may be region B as referred to in the context of a gapmer as described herein. In some embodiments the size of the contiguous sequence which is capable of recruiting RNAse, such as region B, may be higher, such as 10, 11, 12, 13, 14, 15, 16, 17, 18, 19 or 20 nucleotide units.

EP 1 222 309 provides in vitro methods for determining RNaseH activity, which may be used to determine the ability to recruit RNaseH. A oligomer is deemed capable of recruiting RNase H if, when provided with the complementary RNA target, it has an initial rate, as measured in pmol/l/min, of at least 1%, such as at least 5%, such as at least 10% or less than 20% of the equivalent DNA only oligonucleotide, with no 2' substitutions, with phosphorothioate linkage groups between all nucleotides in the oligonucleotide, using the methodology provided by Example 91-95 of EP 1 222 309.

In some embodiments, an oligomer is deemed essentially incapable of recruiting RNaseH if, when provided with the complementary RNA target, and RNaseH, the RNaseH initial rate, as measured in pmol/l/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

In other embodiments, an oligomer is deemed capable of recruiting RNaseH if, when provided with the complementary RNA target, and RNaseH, the RNaseH initial rate, as measured in pmol/l/min, is at least 20%, such as at least 40%, such as at least 60%, such as at least 80% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

Typically the region of the oligomer which forms the consecutive nucleotide units which, when formed in a duplex with the complementary target RNA is capable of recruiting RNase consists of nucleotide units which form a DNA/RNA like duplex with the RNA target—and include both DNA units and LNA units which are in the alpha-L configuration, particularly preferred being alpha-L-oxy LNA.

The oligomer of the invention may comprise a nucleotide sequence which comprises both nucleotides and nucleotide analogues, and may be in the form of a gapmer, a headmer or a mixmer.

A headmer is defined by a contiguous stretch of non-RNase recruiting nucleotide analogues at the 5'-end followed by a contiguous stretch of DNA or modified nucleotide units recognizable and cleavable by the RNase towards the 3'-end (such as at least 7 such nucleotides), and a tailmer is defined by a contiguous stretch of DNA or modified nucleotides recognizable and cleavable by the RNase at the 5'-end (such as at least 7 such nucleotides), followed by a contiguous stretch of non-RNase recruiting nucleotide analogues towards the 3'-end. Other chimeras according to the invention, called mixmers consisting of an alternate composition of DNA or modified nucleotides recognizable and cleavable by RNase and non-RNase recruiting nucleotide analogues. Some nucleotide analogues may also be able to mediate RNaseH binding and cleavage. Since α-L-LNA recruits RNaseH activity to a certain extent, smaller gaps of DNA or modified nucleotides recognizable and cleavable by the RNaseH for the gapmer construct might be required, and more flexibility in the mixmer construction might be introduced.

Gapmer Design

Preferably, the oligomer of the invention is a gapmer. A gapmer oligomer is an oligomer which comprises a contiguous stretch of nucleotides which is capable of recruiting an RNAse, such as RNAseH, such as a region of at least 6 or 7 DNA nucleotides, referred to herein in as region B, wherein region B is flanked both 5' and 3' by regions of affinity enhancing nucleotide analogues, such as between 1-6 nucleotide analogues 5' and 3' to the contiguous stretch of nucleotides which is capable of recruiting RNAse—these regions are referred to as regions A and C respectively.

Preferably the gapmer comprises a (poly)nucleotide sequence of formula (5' to 3'), A-B-C, or optionally A-B-C-D or D-A-B-C, wherein; region A (5' region) consists or comprises of at least one nucleotide analogue, such as at least one LNA unit, such as between 1-6 nucleotide analogues, such as LNA units, and; region B consists or comprises of at least five consecutive nucleotides which are capable of recruiting RNAse (when formed in a duplex with a complementary RNA molecule, such as the mRNA target), such as DNA nucleotides, and; region C (3' region) consists or comprises of at least one nucleotide analogue, such as at least one LNA unit, such as between 1-6 nucleotide analogues, such as LNA units, and; region D, when present consists or comprises of 1, 2 or 3 nucleotide units, such as DNA nucleotides.

In some embodiments, region A consists of 1, 2, 3, 4, 5 or 6 nucleotide analogues, such as LNA units, such as between 2-5 nucleotide analogues, such as 2-5 LNA units, such as 3 or 4 nucleotide analogues, such as 3 or 4 LNA units; and/or region C consists of 1, 2, 3, 4, 5 or 6 nucleotide analogues, such as LNA units, such as between 2-5 nucleotide analogues, such as 2-5 LNA units, such as 3 or 4 nucleotide analogues, such as 3 or 4 LNA units.

In some embodiments B consists or comprises of 5, 6, 7, 8, 9, 10, 11 or 12 consecutive nucleotides which are capable of recruiting RNAse, or between 6-10, or between 7-9, such as 8 consecutive nucleotides which are capable of recruiting RNAse. In some embodiments region B consists or comprises at least one DNA nucleotide unit, such as 1-12 DNA units, preferably between 4-12 DNA units, more preferably between 6-10 DNA units, such as between 7-10 DNA units, most preferably 8, 9 or 10 DNA units.

In some embodiments region A consist of 3 or 4 nucleotide analogues, such as LNA, region B consists of 7, 8, 9 or 10 DNA units, and region C consists of 3 or 4 nucleotide analogues, such as LNA. Such designs include (A-B-C) 3-10-3, 3-10-4, 4-10-3, 3-9-3, 3-9-4, 4-9-3, 3-8-3, 3-8-4, 4-8-3, 3-7-3, 3-7-4, 4-7-3, and may further include region D, which may have one or 2 nucleotide units, such as DNA units.

Further gapmer designs are disclosed in WO2004/046160 and are hereby incorporated by reference.

US provisional application, 60/977,409, hereby incorporated by reference, refers to 'shortmer' gapmer oligomers, which, in some embodiments may be the gapmer oligomer according to the present invention.

In some embodiments the oligomer is consisting of a contiguous nucleotide sequence of a total of 10, 11, 12, 13 or 14 nucleotide units, wherein the contiguous nucleotide sequence is of formula (5'-3'), A-B-C, or optionally A-B-C-D or D-A-B-C, wherein; A consists of 1, 2 or 3 nucleotide analogue units, such as LNA units; B consists of 7, 8 or 9 contiguous nucleotide units which are capable of recruiting RNAse when formed in a duplex with a complementary RNA molecule (such as a mRNA target); and C consists of 1, 2 or 3 nucleotide analogue units, such as LNA units. When present, D consists of a single DNA unit.

In some embodiments A consists of 1 LNA unit. In some embodiments A consists of 2 LNA units. In some embodiments A consists of 3 LNA units. In some embodiments C consists of 1 LNA unit. In some embodiments C consists of 2

LNA units. In some embodiments C consists of 3 LNA units. In some embodiments B consists of 7 nucleotide units. In some embodiments B consists of 8 nucleotide units. In some embodiments B consists of 9 nucleotide units. In some embodiments B comprises of between 1-9 DNA units, such as 2, 3, 4, 5, 6, 7 or 8 DNA units. In some embodiments B consists of DNA units. In some embodiments B comprises of at least one LNA unit which is in the alpha-L configuration, such as 2, 3, 4, 5, 6, 7, 8 or 9 LNA units in the alpha-L-configuration. In some embodiments B comprises of at least one alpha-L-oxy LNA unit or wherein all the LNA units in the alpha-L- configuration are alpha-L-oxy LNA units. In some embodiments the number of nucleotides present in A-B-C are selected from the group consisting of (nucleotide analogue units-region B-nucleotide analogue units): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1. In some embodiments the number of nucleotides in A-B-C are selected from the group consisting of: 2-7-1, 1-7-2, 2-7-2, 3-7-3, 2-7-3, 3-7-2, 3-7-4, and 4-7-3. In some embodiments both A and C consists of two LNA units each, and B consists of 8 or 9 nucleotide units, preferably DNA units.

Internucleotide Linkages

The terms "linkage group" or "internucleotide linkage" are intended to mean a group capable of covalently coupling together two nucleotides, two nucleotide analogues, and a nucleotide and a nucleotide analogue, etc. Specific and preferred examples include phosphate groups and phosphorothioate groups.

The nucleotides of the oligomer of the invention or contiguous nucleotides sequence thereof are coupled together via linkage groups. Suitably each nucleotide is linked to the 3' adjacent nucleotide via a linkage group.

Suitable internucleotide linkages include those listed within PCT/DK2006/000512, for example the internucleotide linkages listed on the first paragraph of page 34 of PCT/DK2006/000512 (hereby incorporated by reference).

It is, in some embodiments, preferred to modify the internucleotide linkage from its normal phosphodiester to one that is more resistant to nuclease attack, such as phosphorothioate or boranophosphate—these two, being cleavable by RNase H, also allow that route of antisense inhibition in reducing the expression of the target gene.

Suitable sulphur (S) containing internucleotide linkages as provided herein may be preferred. Phosphorothioate internucleotide linkages are also preferred, particularly for the gap region (B) of gapmers. Phosphorothioate linkages may also be used for the flanking regions (A and C, and for linking A or C to D, and within region D, as appropriate).

Regions A, B and C, may however comprise internucleotide linkages other than phosphorothioate, such as phosphodiester linkages, particularly for instance when the use of nucleotide analogues protects the internucleotide linkages within regions A and C from endo-nuclease degradation—such as when regions A and C comprise LNA nucleotides.

The internucleotide linkages in the oligomer may be phosphodiester, phosphorothioate or boranophosphate so as to allow RNase H cleavage of targeted RNA. Phosphorothioate is preferred, for improved nuclease resistance and other reasons, such as ease of manufacture.

In one aspect of the oligomer of the invention, the nucleotides and/or nucleotide analogues are linked to each other by means of phosphorothioate groups.

It is recognised that the inclusion of phosphodiester linkages, such as one or two linkages, into an otherwise phosphorothioate oligomer, particularly between or adjacent to nucleotide analogue units (typically in region A and or C) can modify the bioavailability and/or bio-distribution of an oligomer—see WO2008/053314, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleotide linkage groups are phosphorothioate. When referring to specific gapmer oligonucleotide sequences, such as those provided herein it will be understood that, in various embodiments, when the linkages are phosphorothioate linkages, alternative linkages, such as those disclosed herein may be used, for example phosphate (phosphodiester) linkages may be used, particularly for linkages between nucleotide analogues, such as LNA, units. Likewise, when referring to specific gapmer oligonucleotide sequences, such as those provided herein, when the C residues are annotated as 5' methyl modified cytosine, in various embodiments, one or more of the Cs present in the oligomer may be unmodified C residues in some embodiments Oligomeric Compounds The oligomers of the invention may, for example, be selected from the group consisting of 22-43 and 44 to 80.

Conjugates

In the context of this disclosure, the term "conjugate" indicates a heterogenous molecule formed by the covalent attachment ("conjugation") of the oligomer as described herein to one or more non-nucleotide, or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethylene glycol.

Therefore, in various embodiments, the oligomer of the invention may comprise both a polynucleotide region which typically consists of a contiguous sequence of nucleotides, and a further non-nucleotide region. When referring to the oligomer of the invention consisting of a contiguous nucleotide sequence, the compound may comprise non-nucleotide components, such as a conjugate component.

In various embodiments of the invention the oligomeric compound is linked to ligands/conjugates, which may be used, e.g. to increase the cellular uptake of oligomeric compounds. WO2007/031091 provides suitable ligands and conjugates, which are hereby incorporated by reference.

The invention also provides for a conjugate comprising the compound according to the invention as herein described, and at least one non-nucleotide or non-polynucleotide moiety covalently attached to said compound. Therefore, in various embodiments where the compound of the invention consists of a specified nucleic acid or nucleotide sequence, as herein disclosed, the compound may also comprise at least one non-nucleotide or non-polynucleotide moiety (e.g. not comprising one or more nucleotides or nucleotide analogues) covalently attached to said compound.

Conjugation (to a conjugate moiety) may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

The oligomers of the invention may also be conjugated to active drug substances, for example, aspirin, ibuprofen, a sulfa drug, an antidiabetic, an antibacterial or an antibiotic.

In certain embodiments the conjugated moiety is a sterol, such as cholesterol.

In various embodiments, the conjugated moiety comprises or consists of a positively charged polymer, such as a positively charged peptides of, for example between 1-50, such as 2-20 such as 3-10 amino acid residues in length, and/or polyalkylene oxide such as polyethylglycol (PEG) or polypropylene glycol—see WO 2008/034123, hereby incorporated by reference. Suitably the positively charged polymer, such as a polyalkylene oxide may be attached to the oligomer of the invention via a linker such as the releasable inker described in WO 2008/034123.

By way of example, the following conjugate moieties may be used in the conjugates of the invention:

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis. In some embodiments, the oligomers are functionalized with a hindered ester containing an aminoalkyl linker, wherein the alkyl portion has the formula $(CH_2)_w$, wherein w is an integer ranging from 1 to 10, pref-

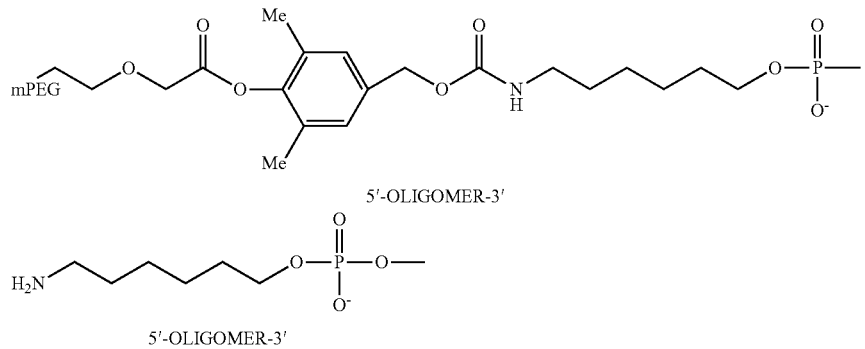

5'-OLIGOMER-3'

Activated Oligomers

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl. In some embodiments, the functional moiety is self-cleaving. In other embodiments, the functional moiety is biodegradable. See e.g., U.S. Pat. No. 7,087,229, which is incorporated by reference herein in its entirety.

erably about 6, wherein the alkyl portion of the alkylamino group can be straight chain or branched chain, and wherein the functional group is attached to the oligomer via an ester group $(-O-C(O)-(CH_2)_w NH)$.

In other embodiments, the oligomers are functionalized with a hindered ester containing a $(CH_2)_w$-sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group $(-O-C(O)-(CH_2)_w SH)$ In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular by methods disclosed in International Pub. No. WO 2008/034122 and the examples therein, which is incorporated herein by reference in its entirety.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention may have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.). In some embodiments in some embodiments Compositions The oligomer of the invention may be used in pharmaceutical formulations and compositions. Suitably, such compositions comprise a pharmaceutically acceptable diluent, carrier, salt or adjuvant. PCT/DK2006/000512 provides suitable and preferred pharmaceutically acceptable diluent, carrier and adjuvants—which are hereby incorporated by reference. Suitable dosages, formulations, administration routes, compositions, dosage forms, combinations with other therapeutic agents, pro-drug formulations are also provided in PCT/DK2006/000512-which are also hereby incorporated by reference.

Applications

The oligomers of the invention may be utilized as research reagents for, for example, diagnostics, therapeutics and prophylaxis.

In research, such oligomers may be used to specifically inhibit the synthesis of androgen receptor protein (typically by degrading or inhibiting the mRNA and thereby prevent protein formation) in cells and experimental animals thereby facilitating functional analysis of the target or an appraisal of its usefulness as a target for therapeutic intervention.

In diagnostics the oligomers may be used to detect and quantitate androgen receptor expression in cell and tissues by Northern blotting, in-situ hybridisation or similar techniques.

For therapeutics, an animal or a human, suspected of having a disease or disorder, which can be treated by modulating the expression of androgen receptor is treated by administering antisense compounds in accordance with this invention, suitably in an effective amount. Further provided are methods of treating a mammal, such as treating a human, suspected of having or being prone to a disease or condition, associated with expression and/or activity of androgen receptor by administering a therapeutically or prophylactically effective amount of one or more of the oligomers or compositions of the invention.

The pharmaceutical composition according to the invention may be used for the treatment of conditions associated with abnormal levels of androgen receptor activity, such as cancer, such as prostate or breast cancer, The pharmaceutical composition according to the invention may be used for the treatment of alopecia, benign prostatic hyperplasia, spinal and muscular atrophy and Kennedy disease. or polyglutamate disease.

It will be recognised that treatment as referred to herein may be prophylactic.

Suitable dosages, formulations, administration routes, compositions, dosage forms, combinations with other therapeutic agents, pro-drug formulations are also provided in PCT/DK2006/000512—which are hereby incorporated by reference, although it should be recognised that the aspects of PCT/DK2006/000512 which are only specifically applicable to the treatment of cancer may not be appropriate in the therapeutic/pharmaceutical compositions and methods of the present invention.

The invention also provides for a pharmaceutical composition comprising a compound or a conjugate as herein described or a conjugate, and a pharmaceutically acceptable diluent, carrier or adjuvant. PCT/DK2006/000512 provides suitable and preferred pharmaceutically acceptable diluent, carrier and adjuvants—which are hereby incorporated by reference.

The oligomer, a conjugate or a pharmaceutical composition according to the invention is typically administered in an effective amount.

The invention also provides for the use of the compound or conjugate of the invention as described for the manufacture of a medicament for the treatment of a disorder as referred to herein, or for a method of the treatment of as a disorder as referred to herein.

The invention also provides for a method for treating a disorder as referred to herein said method comprising administering a compound according to the invention as herein described, and/or a conjugate according to the invention, and/or a pharmaceutical composition according to the invention to a patient in need thereof.

Pharmaceutical Compositions Comprising More than One Active Ingredient

The pharmaceutical composition according to the invention may further comprise other active ingredients, including those which are indicated as being useful for the treatment of cancer such as prostate cancer or breast cancer, particularly agents used in conventional antiandrogen therapy.

One such class of compounds are Nonsteroidal antiandrogens (NSAAs), which block the binding of androgens at the receptor site. Diarylhydantoin type androgen receptor ligand binding inhibitors or pharmaceutically acceptable salts thereof including, for example, those disclosed in U.S. Pat. No. 7,709,517 may be used.

Luteinizing hormone-releasing hormone analogs (LHRH-As) suppress testicular production of androgens to castrate levels.

NSAAs, such as bicalutamide (CASODEX) when used with an LHRH-A as part of Combined Androgen Blockade therapy, help inhibit the growth of prostate cancer cells. In one embodiment, the present invention provides for a combined androgen blockade therapy, characterised in that the therapy comprises administering an antisense oligomer composition according to the invention, and an NSAA and/or LHRH-A agent, which may be administered prior to, during or subsequent to the administering of an antisense oligomer composition of the invention. Generally, the antisense oligomer composition and one or more androgen blockade agents may be administered so that their effects are concurrent, i.e., temporally overlapping in the subject.

The invention also provides a kit of parts wherein a first part includes an antisense oligomer, conjugate thereof and/or oligomer pharmaceutical composition according to the invention and a further part comprises a Nonsteroidal antiandrogen and/or a Luteinizing hormone-releasing hormone analog. One embodiment provides a kit that includes an antisense oligomer, pharmaceutically acceptable salt thereof, or conjugate thereof (or pharmaceutically acceptable salt of the conjugate) and a diarylhydantoin type androgen receptor ligand binding inhibitor or pharmaceutically acceptable salt thereof including, for example, those disclosed in U.S. Pat. No. 7,709,517. It is therefore envisaged that the kit of parts may be used in a method of treatment, as referred to herein, where the method comprises administering both the first part and the further part, either simultaneously or one after the other.

Oligomer Embodiments

The following AR antisense oligomer embodiments of the present invention may, for example, be used in combination with the diarylhydantoin AR ligand binding inhibitor embodiments described herein.

1. An oligomer of between 10-50 nucleobases in length which comprises as a contiguous nucleobase sequence of a total of between 10-50 nucleobases, wherein said contiguous nucleobase sequence is at least 80% homologous to a corresponding region of a nucleic acid which encodes a mammalian androgen receptor.
2. The oligomer according to embodiment 1, wherein said oligomer comprises at least one LNA unit.
3. The oligomer according to embodiment 1 or 2, wherein the contiguous nucleobase sequence comprises no more than 3, such as no more than 2 mismatches to the corresponding region of a nucleic acid which encodes a mammalian androgen receptor.
4. The oligomer according to embodiment 3, wherein said contiguous nucleobase sequence comprises no more than a single mismatch to the corresponding region of a nucleic acid which encodes a mammalian androgen receptor.
5. The oligomer according to embodiment 4, wherein said contiguous nucleobase sequence comprises no mismatches, (i.e. is complementary to) the corresponding region of a nucleic acid which encodes a mammalian androgen receptor.
6. The oligomer according to any one of embodiments 1-5, wherein the nucleobase sequence of the oligomer consists of the contiguous nucleobase sequence.
7. The oligomer according to any one of embodiments 1-6, wherein the nucleic acid which encodes a mammalian androgen receptor is the human androgen receptor nucleotide sequence such as SEQ ID No 1, or a naturally occurring allelic variant thereof.
8. The oligomer according to any one of embodiments 1-7, wherein the contiguous nucleobase sequence is complementary to a corresponding region of both the human androgen receptor nucleic acid sequence and a non-human mammalian androgen receptor nucleic acid sequence, such as the mouse androgen receptor nucleic acid sequence.
9. The oligomer according to any one of embodiments 1 to 8, wherein the contiguous nucleobase sequence comprises a contiguous subsequence of at least 7, nucleobase residues which, when formed in a duplex with the complementary androgen receptor target RNA is capable of recruiting RNaseH.
10. The oligomer according to embodiment 9, wherein the contiguous nucleobase sequence comprises of a contiguous subsequence of at least 8, at least 9 or at least 10 nucleobase residues which, when formed in a duplex with the complementary androgen receptor target RNA is capable of recruiting RNaseH.
11. The oligomer according to any one of embodiments 9 or 10 wherein said contiguous subsequence is at least 9 or at least 10 nucleobases in length, such as at least 12 nucleobases or at least 14 nucleobases in length, such as 14, 15 or 16 nucleobases residues which, when formed in a duplex with the complementary androgen receptor target RNA is capable of recruiting RNaseH.
12. The oligomer according to embodiment any one of embodiments 1-11 wherein said oligomer is conjugated with one or more non-nucleobase compounds.
13. The oligomer according to any one of embodiments 1-12, wherein said oligomer has a length of between 10-22 nucleobases.
14. The oligomer according to any one of embodiments 1-13, wherein said oligomer has a length of between 12-18 nucleobases.
15. The oligomer according to any one of embodiments 1-14, wherein said oligomer has a length of 14, 15 or 16 nucleobases.
16. The oligomer according to any one of embodiments 1-15, wherein said continuous nucleobase sequence corresponds to a contiguous nucleotide sequence present in a nucleic acid sequence selected from the group consisting of SEQ ID NO 86-106.
17. The oligomer according to any one of embodiments 1-16, wherein the oligomer or contiguous nucleobase sequence comprises, or is selected from a corresponding nucleobase sequence present in a nucleotide sequence selected from the group consisting of SEQ ID NO 2-22.
18. The oligomer according to any one of embodiments 1-17, wherein said contiguous nucleobase sequence comprises at least one affinity enhancing nucleotide analogue.
19. The oligomer according to embodiment 18, wherein said contiguous nucleobase sequence comprises a total of 2, 3, 4, 5, 6, 7, 8, 9 or 10 affinity enhancing nucleotide analogues, such as between 5 and 8 affinity enhancing nucleotide analogues.
20. The oligomer according to any one of embodiments 1-19 which comprises at least one affinity enhancing nucleotide analogue, wherein the remaining nucleobases are selected from the group consisting of DNA nucleotides and RNA nucleotides, preferably DNA nucleotides.
21. The oligomer according to any one of embodiments 1-20, wherein the oligomer comprises of a sequence of nucleobases of formula, in 5' to 3' direction, A-B-C, and optionally of formula A-B-C-D, wherein:

A consists or comprises of at least one nucleotide analogue, such as 1, 2, 3, 4, 5 or 6 nucleotide analogues, preferably between 2-5 nucleotide analogues, preferably 2, 3 or 4 nucleotide analogues, most preferably 2, 3 or 4 consecutive nucleotide analogues and;

B consists or comprises at least five consecutive nucleobases which are capable of recruiting RNAseH (when formed in a duplex with a complementary RNA molecule, such as the AR mRNA target), such as DNA nucleobases, such as 5, 6, 7, 8, 9, 10, 11 or 12 consecutive nucleobases which are capable of recruiting RNAseH, or between 6-10, or between 7-9, such as 8 consecutive nucleobases which are capable of recruiting RNAseH, and;

C consists or comprises of at least one nucleotide analogue, such as 1, 2, 3, 4, 5, or 6 nucleotide analogues, preferably between 2-5 nucleotide analogues, such as 2, 3 or 4 nucleotide analogues, most preferably 2, 3 or 4 consecutive nucleotide analogues, and;

D when present, consists or comprises, preferably consists, of one or more DNA nucleotide, such as between 1-3 or 1-2 DNA nucleotides.

22. The oligomer according to embodiment 21, wherein region A consists or comprises of 2, 3 or 4 consecutive nucleotide analogues.

23. The oligomer according to any one of embodiments 21-22, wherein region B consists or comprises of 7, 8, 9 or 10 consecutive DNA nucleotides or equivalent nucleobases which are capable of recruiting RNAseH when formed in a duplex with a complementary RNA, such as the androgen receptor mRNA target.

24. The oligomer according to any one of embodiments 21-23, wherein region C consists or comprises of 2, 3 or 4 consecutive nucleotide analogues.

25. The oligomer according to any one of embodiments 21-24, wherein region D consists, where present, of one or two DNA nucleotides.

26. The oligomer according to any one of embodiments 21-25, wherein:
A Consists or comprises of 3 contiguous nucleotide analogues;
B Consists or comprises of 7, 8, 9 or 10 contiguous DNA nucleotides or equivalent nucleobases which are capable of recruiting RNAseH when formed in a duplex with a complementary RNA, such as the androgen receptor mRNA target;
C Consists or comprises of 3 contiguous nucleotide analogues;
D Consists, where present, of one or two DNA nucleotides.

27. The oligomer according to embodiment 26, wherein the contiguous nucleobase sequence consists of 10, 11, 12, 13 or 14 nucleobases, and wherein;
A Consists of 1, 2 or 3 contiguous nucleotide analogues;
B Consists of 7, 8, or 9 consecutive DNA nucleotides or equivalent nucleobases which are capable of recruiting RNAseH when formed in a duplex with a complementary RNA, such as the androgen receptor mRNA target;
C Consists of 1, 2 or 3 contiguous nucleotide analogues;
D Consists, where present, of one DNA nucleotide.

28. The oligomer according to anyone of embodiments 21-27, wherein B comprises at least one LNA nucleobase which is in the alpha-L configuration, such as alpha-L-oxy LNA.

29. The oligomer according to any one of embodiments 1-28, wherein the nucleotide analogue(s) are independently or collectively selected from the group consisting of: Locked Nucleic Acid (LNA) units; 2'-O-alkyl-RNA units, 2'-OMe-RNA units, 2'-amino-DNA units, 2'-fluoro-DNA units, PNA units, HNA units, and INA units.

30. The oligomer according to embodiment 29 wherein all the nucleotide analogues(s) are LNA units.

31. The oligomer according to any one of embodiments 1-30, which comprises 1, 2, 3, 4, 5, 6, 7, 8, 9 or 10 LNA units such as between 2 and 8 nucleotide LNA units.

32. The oligomer according to any one of the embodiments 29-31, wherein the LNAs are independently selected from oxy-LNA, thio-LNA, and amino-LNA, in either of the beta-D and alpha-L configurations or combinations thereof.

33. The oligomer according to embodiment 32, wherein the LNAs are all beta-D-oxy-LNA.

34. The oligomer according to any one of embodiments 21-33, wherein the nucleotide analogues or nucleobases of regions A and C are beta-D-oxy-LNA.

35. The oligomer according to any one of embodiments 1-34, wherein at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

36. The oligomer according to any one of embodiments 1-35, wherein said oligomer hybridises with a corresponding mammalian androgen receptor mRNA with a $T_m$ of at least 50° C.

37. The oligomer according to any one of embodiments 1-36, wherein said oligomer hybridises with a corresponding mammalian androgen receptor mRNA with a $T_m$ of no greater than 80° C.

38. The oligomer according to any one of embodiments 1-37, wherein the internucleoside linkages are independently selected from the group consisting of: phosphodiester, phosphorothioate and boranophosphate.

39. The oligomer according to embodiment 38, wherein the oligomer comprises at least one phosphorothioate internucleoside linkage.

40. The oligomer according to embodiment 39, wherein the internucleoside linkages adjacent to or between DNA or RNA units, or within region B are phosphorothioate linkages.

41. The oligomer according to embodiment 39 or 40, wherein the linkages between at least one pair of consecutive nucleotide analogues is a phosphodiester linkage.

42. The oligomer according to embodiment 39 or 40, wherein all the linkages between consecutive nucleotide analogues are phosphodiester linkages.

43. The oligomer according to embodiment 42 wherein all the internucleoside linkages are phosphorothioate linkages.

44. A conjugate comprising the oligomer according to any one of the embodiments 1-43 and at least one non-nucleotide or non-polynucleotide moiety covalently attached to said compound.

45. A pharmaceutical composition comprising an oligomer as defined in any of embodiments 1-43 or a conjugate as defined in embodiment 44, and a pharmaceutically acceptable diluent, carrier, salt or adjuvant.

46. A pharmaceutical composition according to 45, wherein the oligomer is constituted as a pro-drug.

Antisense Oligomer Examples

Example 1

Monomer Synthesis

The LNA monomer building blocks and derivatives were prepared following published procedures and references cited therein—see WO07/031,081 and the references cited therein.

Example 2

Oligonucleotide Synthesis

Oligonucleotides were synthesized according to the method described in WO07/031,081. Table 1 shows examples of antisense oligonucleotide sequences of the invention. Tables 2 and 3 show examples of antisense oligonucleotides (oligos) of the invention.

Example 3

Design of the Oligonucleotides

In accordance with the present invention, a series of different oligonucleotides were designed to target different regions of human Androgen receptor mRNA (GenBank accession number NM_000044, SEQ ID NO: 1).

TABLE 1

Antisense oligonucleotide sequences of the invention: SEQ ID NOS: 2-22 are oligo sequences designed to target human Androgen receptor mRNA.

| SEQ ID NO | Sequence (5'-3') | Length (bases) | Target site NM_000044 |
|---|---|---|---|
| SEQ ID NO: 2 | GAGAACCATCCTCACC | 16 | 1389-1404 |
| SEQ ID NO: 3 | GGACCAGGTAGCCTGT | 16 | 1428-1443 |
| SEQ ID NO: 4 | CCCCTGGACTCAGATG | 16 | 1881-1896 |
| SEQ ID NO: 5 | GCACAAGGAGTGGGAC | 16 | 1954-1969 |
| SEQ ID NO: 6 | GCTGTGAAGAGAGTGT | 16 | 2422-2437 |
| SEQ ID NO: 7 | TTTGACACAAGTGGGA | 16 | 2663-2678 |
| SEQ ID NO: 8 | GTGACACCCAGAAGCT | 16 | 2813-2828 |
| SEQ ID NO: 9 | CATCCCTGCTTCATAA | 16 | 2975-2990 |
| SEQ ID NO: 10 | ACCAAGTTTCTTCAGC | 16 | 3008-3023 |
| SEQ ID NO: 11 | CTTGGCCCACTTGACC | 16 | 3263-3278 |
| SEQ ID NO: 12 | TCCTGGAGTTGACATT | 16 | 3384-3399 |
| SEQ ID NO: 13 | CACTGGCTGTACATCC | 16 | 3454-3469 |
| SEQ ID NO: 14 | CATCCAAACTCTTGAG | 16 | 3490-3505 |
| SEQ ID NO: 15 | GCTTTCATGCACAGGA | 16 | 3529-3544 |
| SEQ ID NO: 16 | GAAGTTCATCAAAGAA | 16 | 3594-3609 |
| SEQ ID NO: 17 | AGTTCCTTGATGTAGT | 16 | 3616-3631 |
| SEQ ID NO: 18 | TTGCACAGAGATGATC | 16 | 3809-3824 |
| SEQ ID NO: 19 | GATGGGCTTGACTTTC | 16 | 3845-3860 |
| SEQ ID NO: 20 | CAGGCAGAAGACATCT | 16 | 3924-3939 |
| SEQ ID NO: 21 | CCCAAGGCACTGCAGA | 16 | 3960-3975 |
| SEQ ID NO: 22 | GCTGACATTCATAGCC | 16 | 3114-3129 |
| SEQ ID NO: 86 | TGGGGAGAACCATCCTCACCCTGC | 24 | 1385-1408 |
| SEQ ID NO: 87 | TCCAGGACCAGGTAGCCTGTGGGG | 24 | 1424-1447 |
| SEQ ID NO: 88 | TGTTCCCCTGGACTCAGATGCTCC | 24 | 1877-1990 |
| SEQ ID NO: 89 | TGGGGCACAAGGAGTGGGACGCAC | 24 | 1950-1973 |
| SEQ ID NO: 90 | TTCGGCTGTGAAGAGAGTGTGCCA | 24 | 2418-2441 |

TABLE 1-continued

Antisense oligonucleotide sequences of the invention:
SEQ ID NOS: 2-22 are oligo sequences designed
to target human Androgen receptor mRNA.

| SEQ ID NO | Sequence (5'-3') | Length (bases) | Target site NM_000044 |
|---|---|---|---|
| SEQ ID NO: 91 | CGCTTTTGACACAAGTGGGACTGG | 24 | 2659-2682 |
| SEQ ID NO: 92 | CATAGTGACACCCAGAAGCTTCAT | 24 | 2809-2832 |
| SEQ ID NO: 93 | GAGTCATCCCTGCTTCATAACATT | 24 | 2971-2994 |
| SEQ ID NO: 94 | GATTACCAAGTTTCTTCAGCTTCC | 24 | 3004-3027 |
| SEQ ID NO: 95 | AGGCCTTGGCCCACTTGACCACGT | 24 | 3259-3282 |
| SEQ ID NO: 96 | AGCATCCTGGAGTTGACATTGGTG | 24 | 3380-3403 |
| SEQ ID NO: 97 | GACACACTGGCTGTACATCCGGGA | 24 | 3450-3473 |
| SEQ ID NO: 98 | GAGCCATCCAAACTCTTGAGAGAG | 24 | 3486-3509 |
| SEQ ID NO: 99 | CAGTGCTTTCATGCACAGGAATTC | 24 | 3525-3548 |
| SEQ ID NO: 100 | ATTCGAAGTTCATCAAAGAATTTT | 24 | 3590-3613 |
| SEQ ID NO: 101 | ATCGAGTTCCTTGATGTAGTTCAT | 24 | 3612-3635 |
| SEQ ID NO: 102 | GCACTTGCACAGAGATGATCTCTG | 24 | 3805-3828 |
| SEQ ID NO: 103 | AATAGATGGGCTTGACTTTCCCAG | 24 | 3841-3864 |
| SEQ ID NO: 104 | ATAACAGGCAGAAGACATCTGAAA | 24 | 3920-3943 |
| SEQ ID NO: 105 | ATTCCCCAAGGCACTGCAGAGGAG | 24 | 3956-3979 |
| SEQ ID NO: 106 | ATGGGCTGACATTCATAGCCTTCA | 24 | 3110-3133 |

TABLE 2

Oligonucleotide designs of the invention - In SEQ ID NOs: 23-43 upper case letters indicates nucleotide analogue units and subscript "s" represents phosphorothioate linkage. Lower case letters represent nucleotide units. Absence of "s" (if any) indicates phosphodiester linkage.
Oligonucleotide designs

| SEQ ID NO | Sequence (5'-3') |
|---|---|
| SEQ ID NO: 23 | 5'-$G_s A_s G_s$a$_s$a$_s$c$_s$c$_s$a$_s$t$_s$c$_s$c$_s$t$_s$c$A_s C_s$C-3' |
| SEQ ID NO: 24 | 5'-$G_s G_s A_s$c$_s$c$_s$a$_s$g$_s$g$_s$t$_s$a$_s$g$_s$c$_s$c$T_s G_s$T-3' |
| SEQ ID NO: 25 | 5'-$C_s C_s C_s$c$_s$t$_s$g$_s$g$_s$a$_s$c$_s$t$_s$c$_s$a$_s$g$A_s T_s$G-3' |
| SEQ ID NO: 26 | 5'-$G_s C_s A_s$c$_s$a$_s$a$_s$g$_s$g$_s$a$_s$g$_s$t$_s$g$_s$g$G_s A_s$C-3' |
| SEQ ID NO: 27 | 5'-$G_s C_s T_s$g$_s$t$_s$g$_s$a$_s$a$_s$g$_s$a$_s$g$_s$a$_s$g$T_s G_s$T-3' |
| SEQ ID NO: 28 | 5'-$T_s T_s T_s$g$_s$a$_s$c$_s$a$_s$c$_s$a$_s$a$_s$g$_s$t$_s$g$G_s G_s$A-3' |
| SEQ ID NO: 29 | 5'-$G_s T_s G_s$a$_s$c$_s$a$_s$c$_s$c$_s$c$_s$a$_s$g$_s$a$_s$a$G_s C_s$T-3' |
| SEQ ID NO: 30 | 5'-$C_s A_s T_s$c$_s$c$_s$c$_s$t$_s$g$_s$c$_s$t$_s$t$_s$c$_s$a$T_s A_s$A-3' |
| SEQ ID NO: 31 | 5'-$A_s C_s C_s$a$_s$a$_s$g$_s$t$_s$t$_s$t$_s$c$_s$t$_s$t$_s$c$A_s G_s$C-3' |
| SEQ ID NO: 32 | 5'-$C_s T_s T_s$g$_s$g$_s$c$_s$c$_s$c$_s$a$_s$c$_s$t$_s$t$_s$g$A_s C_s$C-3' |
| SEQ ID NO: 33 | 5'-$T_s C_s C_s$t$_s$g$_s$g$_s$a$_s$g$_s$t$_s$t$_s$g$_s$a$_s$c$A_s T_s$T-3' |
| SEQ ID NO: 34 | 5'-$C_s A_s C_s$t$_s$g$_s$g$_s$c$_s$t$_s$g$_s$t$_s$a$_s$c$_s$a$T_s C_s$C-3' |
| SEQ ID NO: 35 | 5'-$C_s A_s T_s$c$_s$c$_s$a$_s$a$_s$a$_s$c$_s$t$_s$c$_s$t$_s$t$G_s A_s$G-3' |
| SEQ ID NO: 36 | 5'-$G_s C_s T_s$t$_s$t$_s$c$_s$a$_s$t$_s$g$_s$c$_s$a$_s$c$_s$a$G_s G_s$A-3' |
| SEQ ID NO: 37 | 5'-$G_s A_s A_s$g$_s$t$_s$t$_s$c$_s$a$_s$t$_s$c$_s$a$_s$a$_s$a$G_s A_s$A-3' |
| SEQ ID NO: 38 | 5'-$A_s G_s T_s$t$_s$c$_s$c$_s$t$_s$t$_s$g$_s$a$_s$t$_s$g$_s$t$A_s G_s$T-3' |
| SEQ ID NO: 39 | 5'-$T_s T_s G_s$c$_s$a$_s$c$_s$a$_s$g$_s$a$_s$g$_s$a$_s$t$_s$g$A_s T_s$C-3' |
| SEQ ID NO: 40 | 5'-$G_s A_s T_s$g$_s$g$_s$g$_s$c$_s$t$_s$t$_s$g$_s$a$_s$c$_s$t$T_s T_s$C-3' |
| SEQ ID NO: 41 | 5'-$C_s A_s G_s$g$_s$c$_s$a$_s$g$_s$a$_s$a$_s$g$_s$a$_s$c$_s$a$T_s C_s$T-3' |
| SEQ ID NO: 42 | 5'-$C_s C_s C_s$a$_s$a$_s$g$_s$g$_s$c$_s$a$_s$c$_s$t$_s$g$_s$c$A_s G_s$A-3' |
| SEQ ID NO: 43 | 5'-$G_s C_s T_s$ g$_s$ a$_s$ c$_s$ a$_s$ t$_s$ t$_s$ c$_s$ a$_s$ t$_s$ a$_s$ $G_s C_s$C-3' |

Example 4

In Vitro Model

Cell Culture

The effect of antisense oligonucleotides on target nucleic acid expression can be tested in any of a variety of cell types provided that the target nucleic acid is present at measurable levels. The target can be expressed endogenously or by transient or stable transfection of a nucleic acid encoding said target. The expression level of target nucleic acid can be routinely determined using, for example, Northern blot analysis, Real-Time PCR, Ribonuclease protection assays. The following cell types are provided for illustrative purposes, but other cell types can be routinely used, provided that the target is expressed in the cell type chosen.

Cells were cultured in the appropriate medium as described below and maintained at 37° C. at 95-98% humidity and 5% $CO_2$. Cells were routinely passaged 2-3 times weekly.

A549 The human lung cancer cell line A5439 was cultured in DMEM (Sigma)+10% fetal bovine serum (FBS)+2 mM Glutamax I+gentamicin (25 µg/ml).

MCF7 The human breast cancer cell line MCF7 was cultured in EagleMEM (Sigma)+10% fetal bovine serum (FBS)+2 mM Glutamax I+1×NEAA+gentamicin (25 µg/ml).

Example 5

In Vitro Model

Treatment with Antisense Oligonucleotide+

The cell lines listed in example 4 were treated with oligonucleotide using the cationic liposome formulation LipofectAMINE 2000 (Gibco) as transfection vehicle. Cells were seeded in 6-well cell culture plates (NUNC) and treated when 80-90% confluent. Oligo concentrations used ranged from 1 nM to 16 nM final concentration. Formulation of oligo-lipid complexes were carried out essentially as described by the manufacturer using serum-free OptiMEM (Gibco) and a final lipid concentration of 5 µg/mL LipofectAMINE 2000. Cells were incubated at 37° C. for 4 hours and treatment was stopped by removal of oligo-containing culture medium. Cells were washed and serum-containing media was added. After oligo treatment cells were allowed to recover for 20 hours before they were harvested for RNA analysis.

Example 6

In Vitro Model

Extraction of RNA and cDNA Synthesis

Total RNA Isolation and First Strand Synthesis

Total RNA was extracted from cells transfected as described above and using the Qiagen RNeasy kit (Qiagen cat. no. 74104) according to the manufacturer's instructions. First strand synthesis was performed using Reverse Transcriptase reagents from Ambion according to the manufacturer's instructions.

For each sample 0.5 µg total RNA was adjusted to (10.8 µl) with RNase free $H_2O$ and mixed with 2 µl random decamers (50 µM) and 4 µl dNTP mix (2.5 mM each dNTP) and heated to 70° C. for 3 min after which the samples were rapidly cooled on ice. After cooling the samples on ice, 2 µl 10× Buffer RT, 1 µl MMLV Reverse Transcriptase (100 U/µl) and 0.25 µl RNase inhibitor (10 U/µl) was added to each sample, followed by incubation at 42° C. for 60 min, heat inactivation of the enzyme at 95° C. for 10 min and then the sample was cooled to 4° C.

Example 7

In Vitro Model

Analysis of Oligonucleotide Inhibition of Androgen Receptor Expression by Real-time PCR Antisense modulation of Androgen receptor expression can be assayed in a variety of ways known in the art. For example, Androgen receptor mRNA levels can be quantitated by, e.g., Northern blot analysis, competitive polymerase chain reaction (PCR), or real-time PCR. Real-time quantitative PCR is presently preferred. RNA analysis can be performed on total cellular RNA or mRNA.

Methods of RNA isolation and RNA analysis such as Northern blot analysis is routine in the art and is taught in, for example, Current Protocols in Molecular Biology, John Wiley and Sons.

Real-time quantitative (PCR) can be conveniently accomplished using the commercially available Multi-Color Real Time PCR Detection System, available from Applied Biosystem.

Real-Time Quantitative PCR Analysis of Androgen Receptor mRNA Levels

The sample content of human Androgen receptor mRNA was quantified using the human Androgen receptor ABI Prism Pre-Developed TaqMan Assay Reagents (Applied Biosystems cat. no. Hs00171172_ml) according to the manufacturer's instructions.

Glyceraldehyde-3-phosphate dehydrogenase (GAPDH) mRNA quantity was used as an endogenous control for normalizing any variance in sample preparation.

The sample content of human GAPDH mRNA was quantified using the human GAPDH ABI Prism Pre-Developed TaqMan Assay Reagent (Applied Biosystems cat. no. 4310884E) according to the manufacturer's instructions.

Real-time Quantitative PCR is a technique well known in the art and is taught in for example Heid et al. Real time quantitative PCR, Genome Research (1996), 6: 986-994.

Real time PCR: The cDNA from the first strand synthesis performed as described in example 6 was diluted 2-20 times, and analyzed by real time quantitative PCR using Taqman 7500 FAST or 7900 FAST from Applied Biosystems. The primers and probe were mixed with 2× Taqman Fast Universal PCR master mix (2×) (Applied Biosystems Cat. #4364103) and added to 4 µl cDNA to a final volume of 10 µl. Each sample was analysed in duplicate. Assaying 2 fold dilutions of a cDNA that had been prepared on material purified from a cell line expressing the RNA of interest generated standard curves for the assays. Sterile $H_2O$ was used instead of cDNA for the no template control. PCR program: 95° C. for 30 seconds, followed by 40 cycles of 95° C., 3 seconds, 60° C., 20-30 seconds. Relative quantities of target mRNA sequence were determined from the calculated Threshold cycle using the Applied Biosystems Fast System SDS Software Version 1.3.1.21, or SDS Software Version 2.3.

Example 8

In Vitro Analysis

Figure 2:
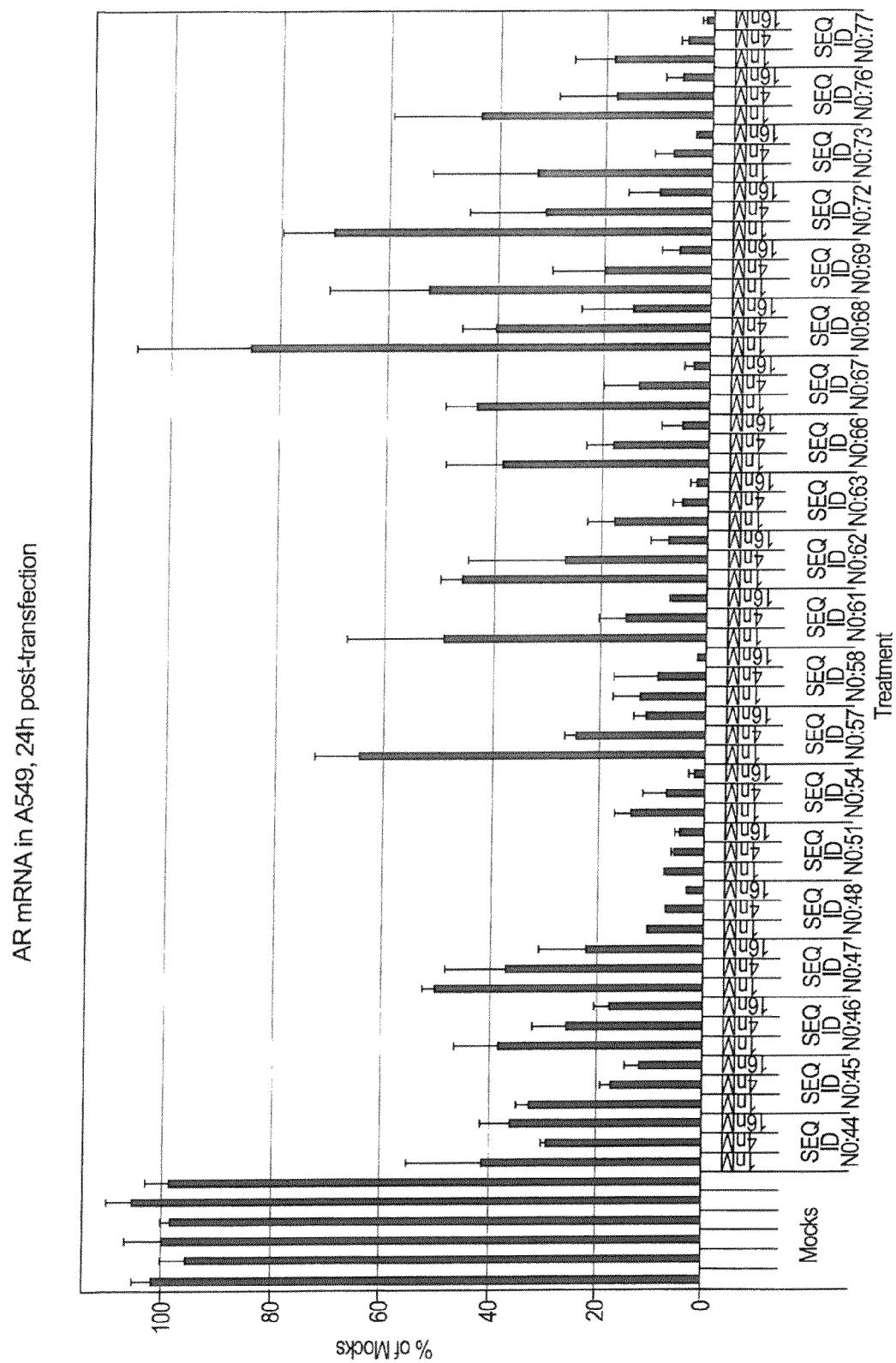
FIG. 2. Oligonucleotides presented in Table 3 were evaluated for their potential to knockdown the androgen receptor mRNA at concentrations of 1, 4 and 16 nM in A549 cells 24 hours after transfection using Real-time PCR. All results were normalised to GAPDH and inhibition of AR mRNA is shown as percent of untreated control. Results shown are an average of three independent experiments.

Antisense Inhibition of Human Androgen Receptor mRNA Expression by Oligonucleotide Compounds Oligonucleotides presented in Table 3 were evaluated for their potential to knockdown of the androgen receptor mRNA at concentrations of 1, 4 and 16 nM (see FIGS. 1 and 2).

TABLE 3

Antisense Inhibition of Human Androgen receptor mRNA expression by oligonucleotides. The data in Table 3 are presented as percentage down-regulation relative to mock transfected cells at 16 nM. Lower case letters represent DNA units, bold upper case letters represent β-D-oxy-LNA units. All LNA C are 5'Methyl C. Subscript "s" represents phosphorothioate linkage. Inhibition of human androgen receptor mRNA expression by oligonucleotides

| Test substance | Sequence (5'-3') | Percent Inhibition of Androgen receptor-MCF7 | Percent Inhibition of Androgen receptor-A549 |
|---|---|---|---|
| SEQ ID NO: 44 | 5'-G$_s$A$_s$G$_s$a$_s$a$_s$c$_s$c$_s$a$_s$t$_s$c$_s$c$_s$t$_s$cA$_s$C$_s$C-3' | 80.1 | 63.8 |
| SEQ ID NO: 45 | 5'-G$_s$G$_s$A$_s$c$_s$c$_s$a$_s$g$_s$g$_s$t$_s$a$_s$g$_s$c$_s$cT$_s$G$_s$T-3' | 89.0 | 88.2 |
| SEQ ID NO: 46 | 5'-C$_s$C$_s$C$_s$c$_s$t$_s$g$_s$g$_s$a$_s$c$_s$t$_s$c$_s$a$_s$gA$_s$T$_s$G-3' | 89.4 | 82.8 |
| SEQ ID NO: 47 | 5'-G$_s$C$_s$A$_s$c$_s$a$_s$a$_s$g$_s$g$_s$a$_s$g$_s$t$_s$g$_s$gG$_s$A$_s$C-3' | 83.1 | 77.7 |
| SEQ ID NO: 48 | 5'-G$_s$C$_s$T$_s$g$_s$t$_s$g$_s$a$_s$a$_s$g$_s$a$_s$g$_s$a$_s$gT$_s$G$_s$T-3' | 93.8 | 96.7 |
| SEQ ID NO: 49 | 5'-C$_s$T$_s$G$_s$t$_s$g$_s$a$_s$a$_s$g$_s$a$_s$g$_s$a$_s$gT$_s$G-3' | n.d. | n.d. |
| SEQ ID NO: 50 | 5'-T$_s$G$_s$tsg$_s$a$_s$a$_s$g$_s$a$_s$g$_s$aG$_s$T$_s$-3' | n.d. | n.d. |
| SEQ ID NO: 51 | 5'-T$_s$T$_s$T$_s$s$_s$g$_s$a$_s$c$_s$a$_s$c$_s$a$_s$a$_s$g$_s$t$_s$gG$_s$G$_s$A-3' | 96.9 | 95.5 |
| SEQ ID NO: 52 | 5'-T$_s$T$_s$G$_s$a$_s$c$_s$a$_s$c$_s$a$_s$a$_s$g$_s$t$_s$gG$_s$G-3' | n.d. | n.d. |
| SEQ ID NO: 53 | 5'-T$_s$G$_s$a$_s$c$_s$a$_s$c$_s$a$_s$a$_s$g$_s$tG$_s$G-3' | n.d. | n.d. |
| SEQ ID NO: 54 | 5'-G$_s$T$_s$G$_s$a$_s$c$_s$a$_s$c$_s$c$_s$c$_s$a$_s$g$_s$a$_s$aG$_s$C$_s$T-3' | 95.4 | 98.3 |
| SEQ ID NO: 55 | 5'-T$_s$G$_s$A$_s$c$_s$a$_s$c$_s$c$_s$c$_s$a$_s$g$_s$a$_s$aG$_s$C-3' | n.d. | n.d. |
| SEQ ID NO: 56 | 5'-G$_s$A$_s$c$_s$a$_s$c$_s$c$_s$c$_s$a$_s$g$_s$aA$_s$G-3' | n.d. | n.d. |
| SEQ ID NO: 57 | 5'-C$_s$A$_s$T$_s$c$_s$c$_s$c$_s$t$_s$g$_s$c$_s$t$_s$t$_s$c$_s$aT$_s$A$_s$A-3' | 89.5 | 88.9 |
| SEQ ID NO: 58 | 5'-A$_s$C$_s$C$_s$a$_s$a$_s$g$_s$t$_s$t$_s$t$_s$c$_s$t$_s$t$_s$cA$_s$G$_s$C-3' | 95.6 | 98.9 |
| SEQ ID NO: 59 | 5'-C$_s$C$_s$A$_s$a$_s$g$_s$t$_s$t$_s$t$_s$c$_s$t$_s$t$_s$cA$_s$G-3' | n.d. | n.d. |
| SEQ ID NO: 60 | 5'-C$_s$A$_s$a$_s$g$_s$t$_s$t$_s$t$_s$c$_s$t$_s$tC$_s$A-3' | n.d. | n.d. |
| SEQ ID NO: 61 | 5'-C$_s$T$_s$T$_s$g$_s$g$_s$c$_s$c$_s$c$_s$a$_s$c$_s$t$_s$t$_s$gA$_s$C$_s$C-3' | 86.7 | 93.3 |
| SEQ ID NO: 62 | 5'-T$_s$C$_s$C$_s$t$_s$g$_s$g$_s$a$_s$g$_s$t$_s$t$_s$g$_s$a$_s$cA$_s$T$_s$T-3' | 81.3 | 93.0 |
| SEQ ID NO: 63 | 5'-C$_s$A$_s$C$_s$t$_s$g$_s$g$_s$c$_s$t$_s$g$_s$t$_s$a$_s$c$_s$aT$_s$C$_s$C-3' | 90.9 | 98.4 |
| SEQ ID NO: 64 | 5'-A$_s$C$_s$T$_s$g$_s$g$_s$c$_s$t$_s$g$_s$t$_s$a$_s$c$_s$aT$_s$C-3' | n.d. | n.d. |
| SEQ ID NO: 65 | 5'-C$_s$T$_s$g$_s$g$_s$c$_s$t$_s$g$_s$t$_s$a$_s$cA$_s$T-3' | n.d. | n.d. |
| SEQ ID NO: 66 | 5'-C$_s$A$_s$T$_s$T$_s$c$_s$c$_s$a$_s$a$_s$a$_s$c$_s$t$_s$c$_s$t$_s$tG$_s$A$_s$G-3' | 79.8 | 95.3 |
| SEQ ID NO: 67 | 5'-G$_s$C$_s$T$_s$t$_s$t$_s$c$_s$a$_s$t$_s$g$_s$c$_s$a$_s$c$_s$aG$_s$G$_s$A-3' | 83.5 | 97.0 |
| SEQ ID NO: 68 | 5'-G$_s$A$_s$A$_s$g$_s$t$_s$t$_s$c$_s$a$_s$t$_s$c$_s$a$_s$a$_s$aG$_s$A$_s$A-3' | 88.2 | 85.6 |
| SEQ ID NO: 69 | 5'-A$_s$G$_s$T$_s$t$_s$c$_s$c$_s$t$_s$t$_s$g$_s$a$_s$t$_s$g$_s$tA$_s$G$_s$T-3' | 92.7 | 94.0 |

TABLE 3-continued

Antisense Inhibition of Human Androgen receptor mRNA expression by oligonucleotides. The data in Table 3 are presented as percentage down-regulation relative to mock transfected cells at 16 nM. Lower case letters represent DNA units, bold upper case letters represent β-D-oxy-LNA units. All LNA C are 5'Methyl C. Subscript "s" represents phosphorothioate linkage. Inhibition of human androgen receptor mRNA expression by oligonucleotides

| Test substance | Sequence (5'-3') | Percent Inhibition of Androgen receptor-MCF7 | Percent Inhibition of Androgen receptor-A549 |
|---|---|---|---|
| SEQ ID NO: 70 | 5'-$G_s^-T_s^-T_s^-c_sc_st_st_sg_sa_st_sg_sT_s^-A_s^-G$-3' | n.d. | n.d. |
| SEQ ID NO: 71 | 5'-$T_s^-T_s^-c_sc_st_st_sg_sa_st_sg_sT_s^-A$-3' | n.d. | n.d. |
| SEQ ID NO: 72 | 5'-$T_s^-T_s^-G_s^-c_sa_sc_sa_sg_sa_sg_sa_st_sg_sA_s^-T_s^-C$-3' | 79.2 | 90.4 |
| SEQ ID NO: 73 | 5'-$G_s^-A_s^-T_s^-g_sg_sg_sc_st_sg_sa_sc_st_sT_s^-T_s^-C$-3' | 91.1 | 97.3 |
| SEQ ID NO: 74 | 5'-$A_s^-T_s^-g_sg_sg_sc_st_sg_sa_sc_st_sT_s^-T$-3' | n.d. | n.d. |
| SEQ ID NO: 75 | 5'-$T_s^-G_s^-g_sg_sc_st_sg_sa_sc_sT_s^-T$-3' | n.d. | n.d. |
| SEQ ID NO: 76 | 5'-$C_s^-A_s^-G_s^-g_sc_sa_sg_sa_sa_sg_sa_sc_sa_sT_s^-C_s^-T$-3' | 85.9 | 94.3 |
| SEQ ID NO: 77 | 5'-$C_s^-C_s^-C_s^-a_sa_sg_sg_sc_sa_sc_st_sg_sc_sA_s^-G_s^-A$-3' | 93.0 | 98.5 |
| SEQ ID NO: 78 | 5'-$C_s^-C_s^-A_s^-a_sg_sg_sc_sa_sc_st_sg_sc_sA_s^-G$-3' | n.d. | n.d. |
| SEQ ID NO: 79 | 5'-$C_s^-A_s^-a_sg_sg_sc_sa_sc_st_sg_sC_s^-A$-3' | n.d. | n.d. |
| SEQ ID NO: 80 | 5'-$G_sC_sT_sg_sa_sc_sa_st_st_sc_sa_st_sa_sG_sC_sC$-3' | n.d. | n.d. |

As shown in Table 3, oligonucleotides of SEQ ID NOs: 48, 51, 54, 58, 63, 69, 73 and 77 at 16 nM demonstrated greater than 90% inhibition of Androgen receptor mRNA expression in A549 and MCF7 cells in these experiments and are therefore preferred. Also preferred are oligonucleotides based on the illustrated antisense oligo sequences, for example varying the length (shorter or longer) and/or nucleobase content (e.g. the type and/or proportion of analogue units), which also provide good inhibition of Androgen receptor expression.

Example 9

In Vivo Analysis

Antisense Inhibition of Mouse Androgen Receptor mRNA Liver Expression by Oligonucleotide Compounds Nude mice were dosed i.v. q3dx4 with 100 mg/kg oligonucleotide (group size of 5 mice). The antisense oligonucleotides (SEQ ID: 48, SEQ ID: 51, SEQ ID: 58, SEQ ID: 63, SEQ ID: 77) were dissolved in 0.9% phosphate buffered saline. Animals were sacrificed 24 h after last dosing and liver tissue was sampled and stored in RNA later until RNA extraction and QPCR analysis. Total RNA was extracted and AR mRNA expression in liver samples was measured by QPCR as described in example 7 using a mouse AR QPCR assay (cat. Mm01238475_ml, Applied Biosystems). Results were normalised to mouse GAPDH (cat. no. 4352339E, Applied Biosystems) and Knockdown was quantitated relative to saline treated controls. The data in Table 4 are presented as percentage down-regulation relative to saline treated animals.

TABLE 4

| In vivo knock-down of AR mRNA expression | |
|---|---|
| Compound | Liver (% KD) |
| Saline | 0 |
| SEQ ID: 51 100 mg/kg | 65.0 +/− 12.6 |
| SEQ ID: 58 100 mg/kg | 95.2 +/− 1.0 |
| SEQ ID: 77 100 mg/kg | 91.9 +/− 3.9 |

As shown in Table 4, oligonucleotides of SEQ ID NOs: 58 and 77 at 100 mg/kg demonstrated greater than 90% inhibition of Androgen receptor mRNA expression in mouse liver cells in these experiments and are therefore preferred.

Example 10

In Vitro Analysis

Antisense Inhibition of Human Androgen Receptor mRNA

Measurement of Proliferating Viable Cells (MTS Assay)

LNCaP prostate cancer and A549 lung cancer cells were seeded to a density of 150000 cells per well in a 6-well plate the day prior to transfection. A549 cells were cultured in DMEM (Sigma)+10% fetal bovine serum (FBS)+2 mM Glutamax I+gentamicin (25 μg/ml) whereas LNCaP cells were cultured in RPMI 1640 Medium (Sigma)+10% fetal bovine serum (FBS)+2 mM Glutamax I+gentamicin (25 μg/ml). The next day medium was removed followed by addition of 1.2 ml OptiMEM containing 5 μg/ml Lipofectamine2000 (Invitrogen). Cells were incubated for 7 min before adding 0.3 ml oligonucleotides diluted in OptiMEM.

Figure 13:
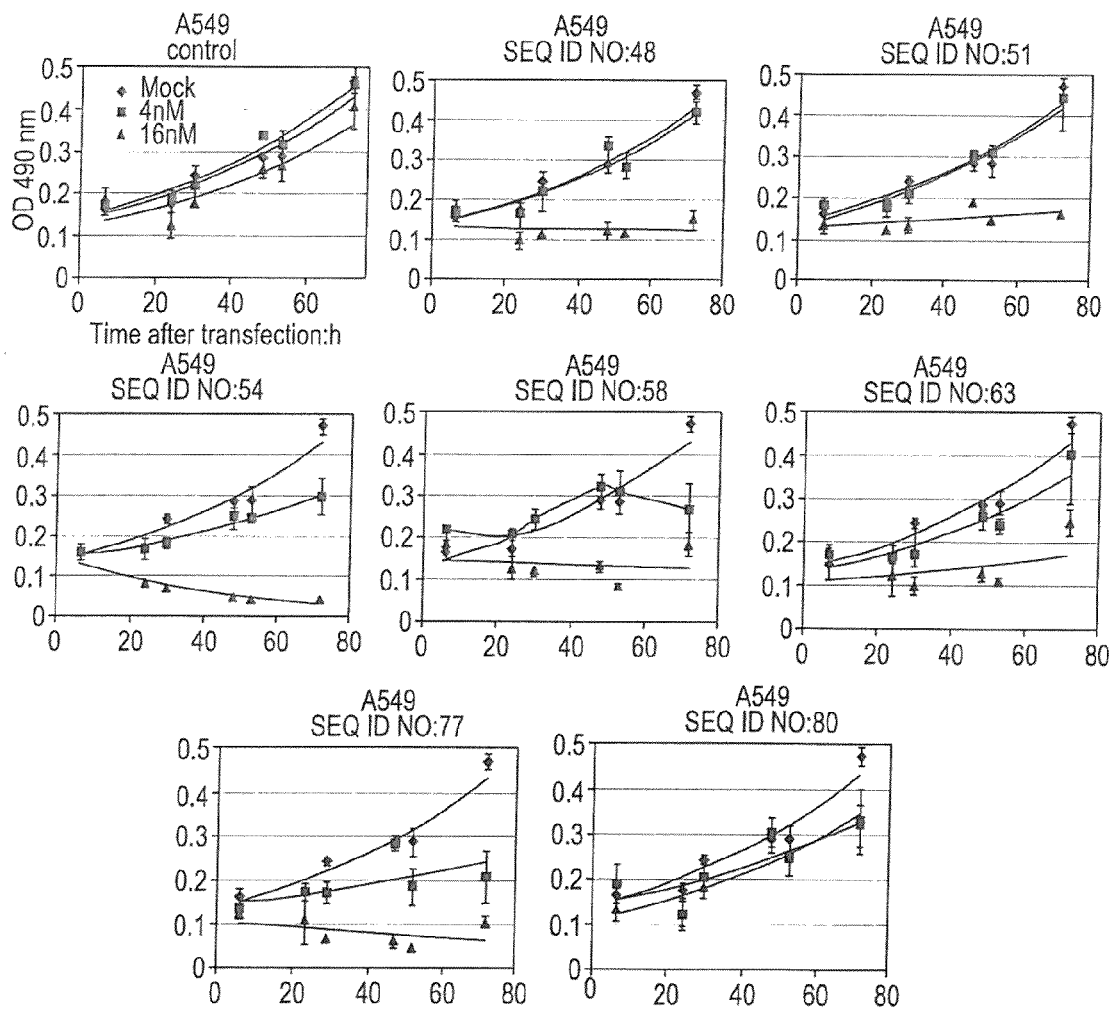
FIG. 13: Cell proliferation assay—A549, time course post-transfection
Figure 14:
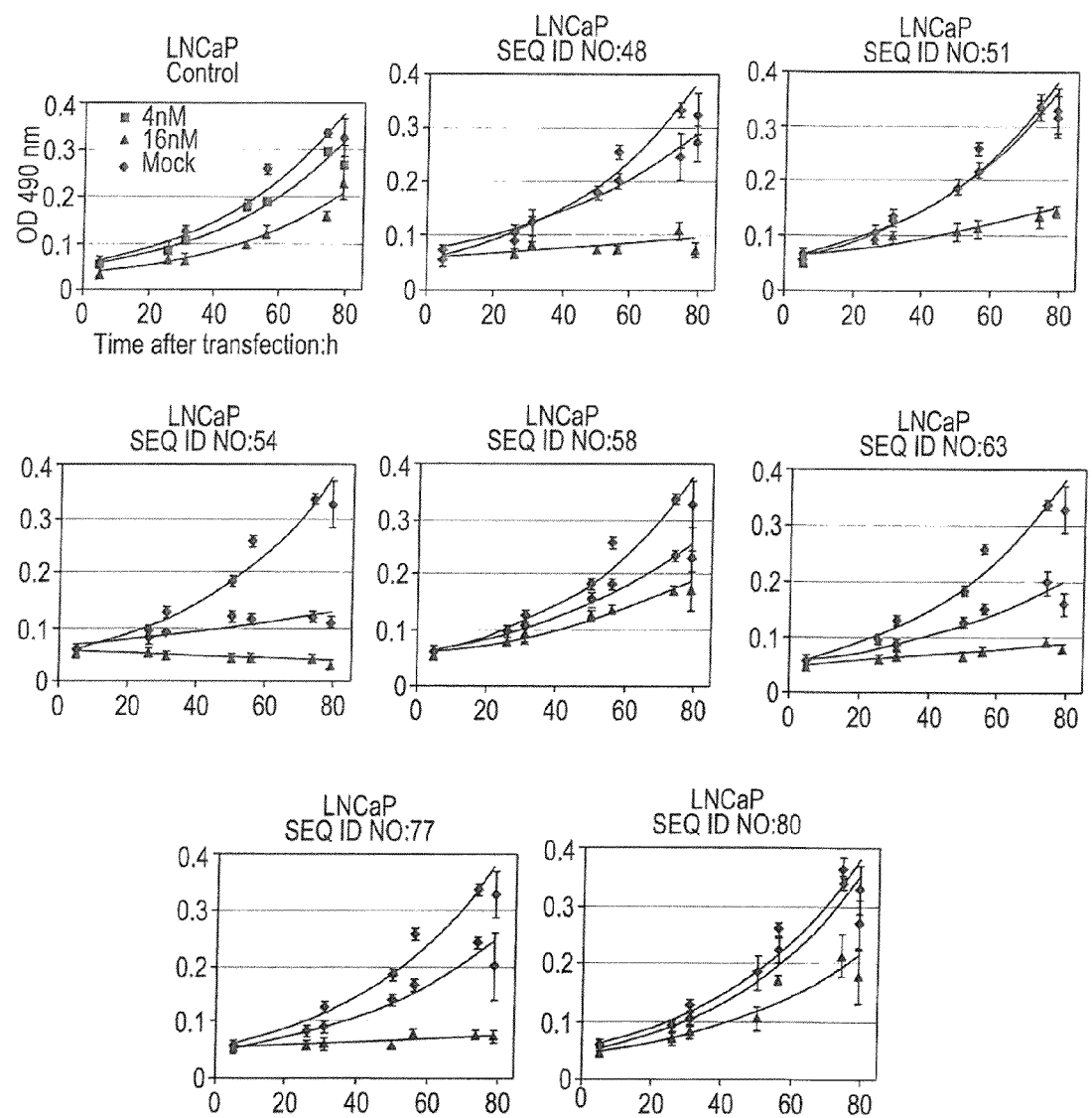
FIG. 14: Cell proliferation assay—time course post-transfection

The final oligonucleotide concentrations were 4 and 16 nM. After 4 hours of treatment, media was removed and cells were trypsinized and seeded to a density of 5000 cells per well in clear 96 well plate (Scientific Orange no. 1472030100) in 100 μl media. Viable cells were measured at the times indicated by adding 10 μl the tetrazolium compound [3-(4,5-dimethyl-2-yl)-5-(3-carboxymethoxyphenyl)-2-(4-sulfophenyl)-2H-tetrazolium, inner salt; MTS] and an electron coupling reagent (phenazine ethosulfate; PES) (CellTiter 96® AQueous One Solution Cell Proliferation Assay, Promega). Viable cells were measured at 490 nm in a Powerwave (Biotek Instruments). The OD490 nm were plotted against time/h. (See FIG. 13 and FIG. 14). As shown in FIG. 13 and FIG. 14, oligonucleotides of SEQ ID NOs: 58 and 77 inhibits growth of both LNCaP prostate and A549 lung cancer cells, and are therefore preferred.

Example 11

In Vitro Analysis

Caspase 3/7 Activity by Antisense Inhibition of Human Androgen Receptor mRNA

Figure 15:
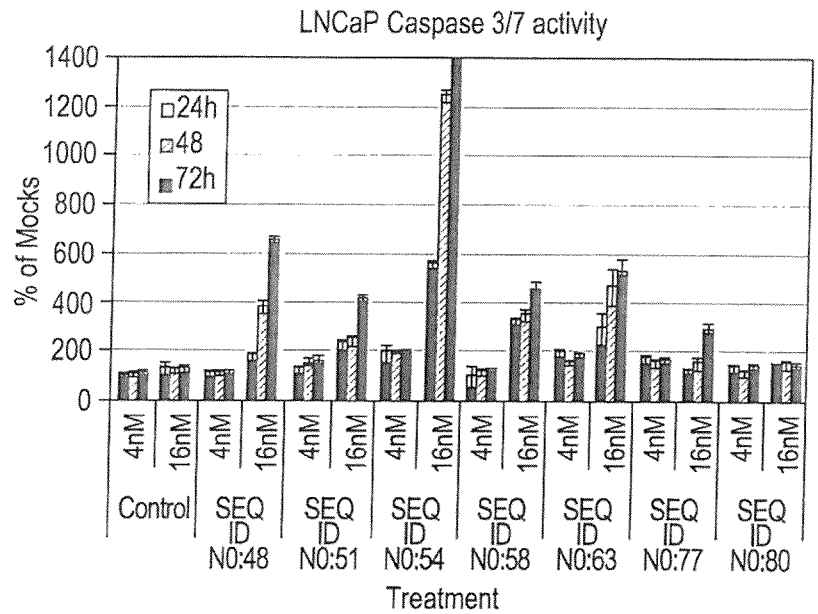
FIG. 15: Caspase 3/7 activity in LNCaP cells, 24, 48 or 72 hours post-transfection.
Figure 16:
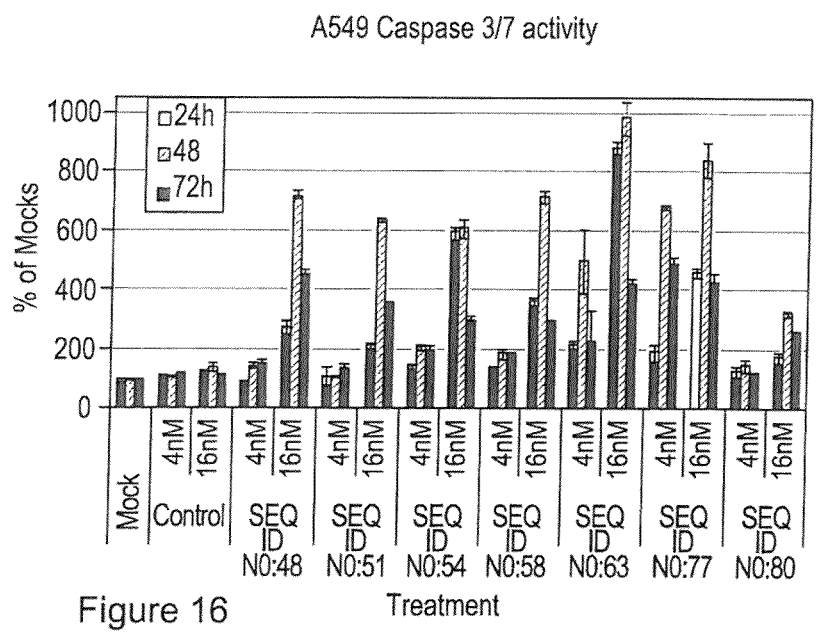
FIG. 16: Caspase 3/7 activity in A549 cells, 24, 48 or 72 hours post-transfection.

LNCaP prostate cancer and A549 lung cancer cells were seeded to a density of 150000 cells per well in a 6-well plate the day prior to transfection. A549 cells were cultured in DMEM (Sigma)+10% fetal bovine serum (FBS)+2 mM Glutamax I+gentamicin (25 μg/ml) whereas LNCaP cells were cultured in RPMI 1640 Medium (Sigma)+10% fetal bovine serum (FBS)+2 mM Glutamax I+gentamicin (25 μg/ml). The next day medium was removed followed by addition of 1.2 ml OptiMEM containing 5 μg/ml Lipofectamine2000 (Invitrogen). Cells were incubated for 7 min before adding 0.3 ml oligonucleotides diluted in OptiMEM. The final oligonucleotide concentrations were 4 and 16 nM. After 4 hours of treatment, media was removed and cells were trypsinized and seeded to a density of 5000 cells per well in white 96 well plate (Nunc) in 100 μl media. Caspase 3/7 activity was measured at the times indicated by adding 100 μl Caspase-Glo 3/7 assay (promega). Caspase 3/7 activity was measured using a luminometer. The caspase 3/7 activities were measured at three different time points 14 h, 48 h and 72 h (See FIG. 15 and FIG. 16). As shown in FIG. 15 and FIG. 16, oligonucleotides of SEQ ID NOs: 58 and 77 induce caspase 3/7 activity in both LNCaP prostate and A549 lung cancer cells and are therefore preferred.

Example 12

In Vitro Analysis

Antisense Inhibition of Human Androgen Receptor mRNA Expression by Oligonucleotide Compounds in Prostate Cancer Cells LNCaP and the Lung Cancer Cell Line A549

Figure 11:
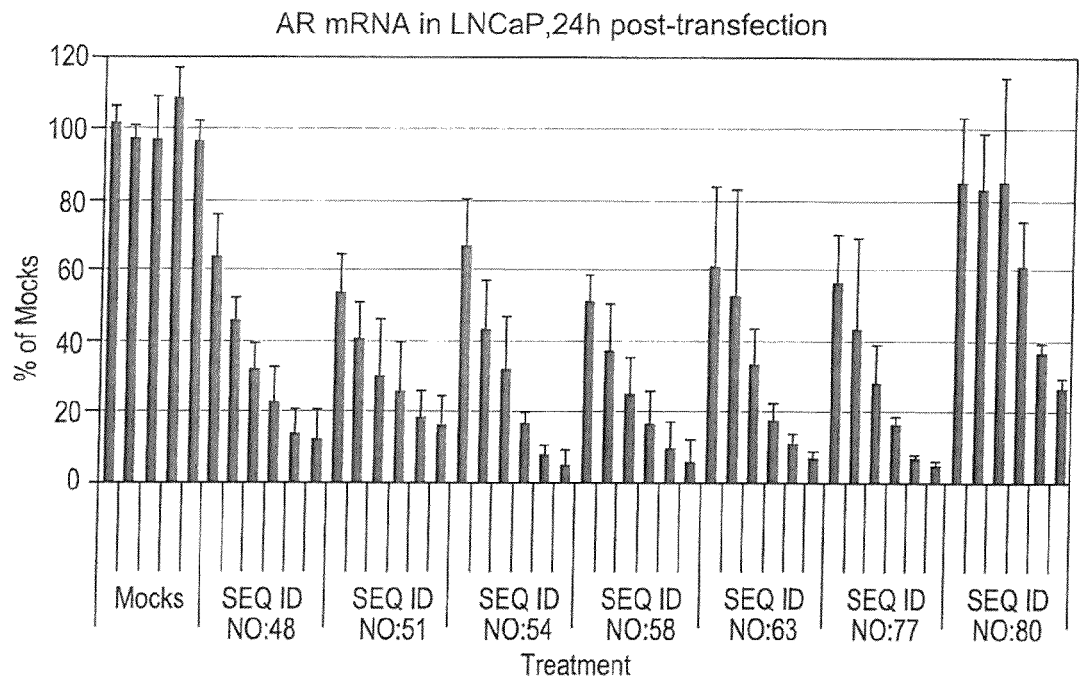
FIG. 11: AR mRNA in LNCaP, 24 h post-transfection
Figure 12:
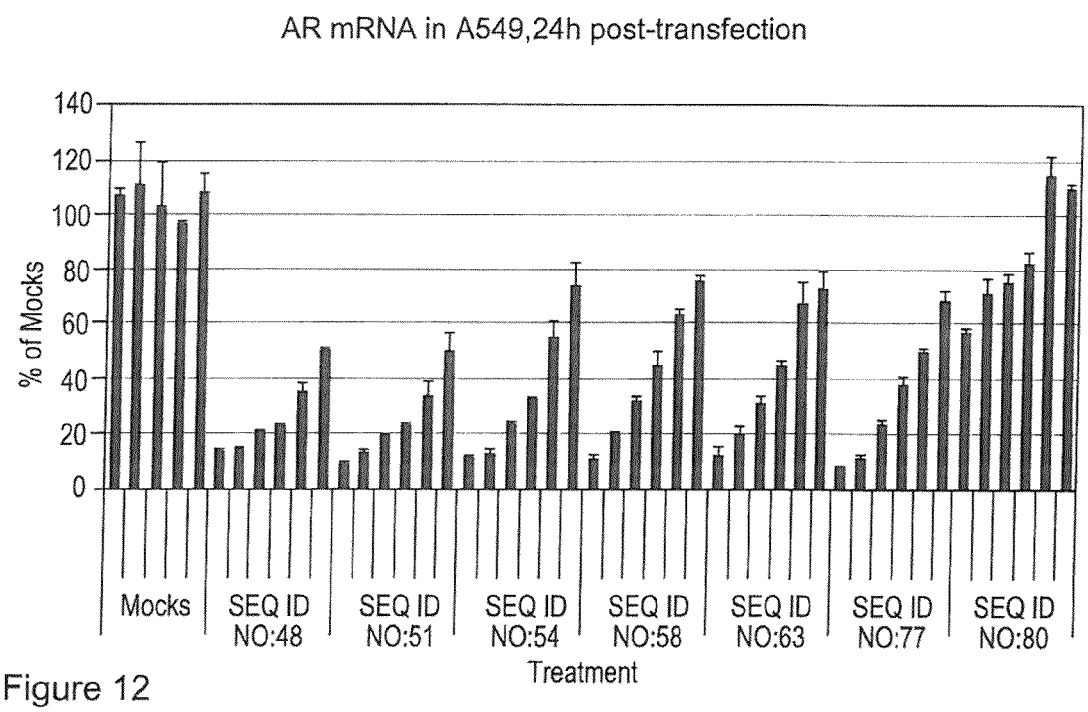
FIG. 12: AR mRNA in A549, 24 h post-transfection

Oligonucleotides were evaluated for their potential to knockdown of the androgen receptor mRNA at concentrations of 0.5, 1, 2, 4, 8 and 16 nM (see FIG. 11). LNCaP prostate cancer and A549 lung cancer cells were seeded to a density of 150000 cells per well in a 6-well plate the day prior to transfection. A549 cells were cultured in DMEM (Sigma)+10% fetal bovine serum (FBS)+2 mM Glutamax I+gentamicin (25 μg/ml) whereas LNCaP cells were cultured in RPMI 1640 Medium (Sigma)+10% fetal bovine serum (FBS)+2 mM Glutamax I+gentamicin (25 μg/ml). The next day medium was removed followed by addition of 1.2 ml OptiMEM containing 5 μg/ml Lipofectamine-2000 (Invitrogen). Cells were incubated for 7 min before adding 0.3 ml oligonucleotides diluted in OptiMEM. The final oligonucleotide concentrations were 0.5, 1, 2, 4, 8 and 16 nM. Cells were washed and serum-containing media was added. After oligo treatment cells were allowed to recover for 20 hours before they were harvested for RNA analysis. The procedure for RNA isolation, cDNA synthesis and qPCR were as described in example 5, 6 and 7. As shown in FIGS. 11 and 12 oligonucleotides of SEQ ID NOs: 58 and 77 were potent in knocking down AR mRNA expression in both the lung cancer cell line A549 and in the androgen receptor-dependent 22RV1 prostate cancer cell line.

Example 13

Figure 17:
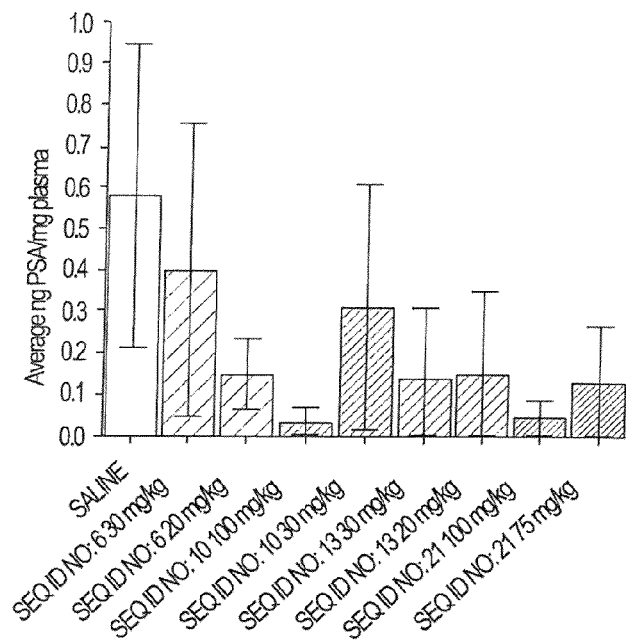
FIG. 17: Average PSA in plasma after in vivo oligomer treatment.

Effect of Antisense Oligonucleotide on PSA (FIG. 17)

Six to seven week old male athymic nu/nu mice (Harlan Sprague Dawley) weighing an average of 27.3±2.4 g were used in the study. Ten million cells of 22RV1 (androgen-independent prostate cancer line) were suspended in PBS (Gibco#14190) and Matrigel (BD#356234) with a ratio of 1:1 were injected subcutaneously into each mouse. When tumors reach an average volume of 150-200 mm$^3$, the mice were divided into nine experimental groups. Two hundred μl of oligo was injected intravenously when the average tumor size reached 152.66±27.97 mm$^3$. Oligos were given every 3 days for a total of 5 times. The control vehicles were given the same regime as the oligos. On day 16, mice were sacrificed and blood collected in EDTA laced tubes and spun for 5 min. 50 μl of the supernatants were then subjected to PSA assay using the ELISA kit from ALPCO Diagnostics in Salem (PSAHU-L01).

Figure 18:
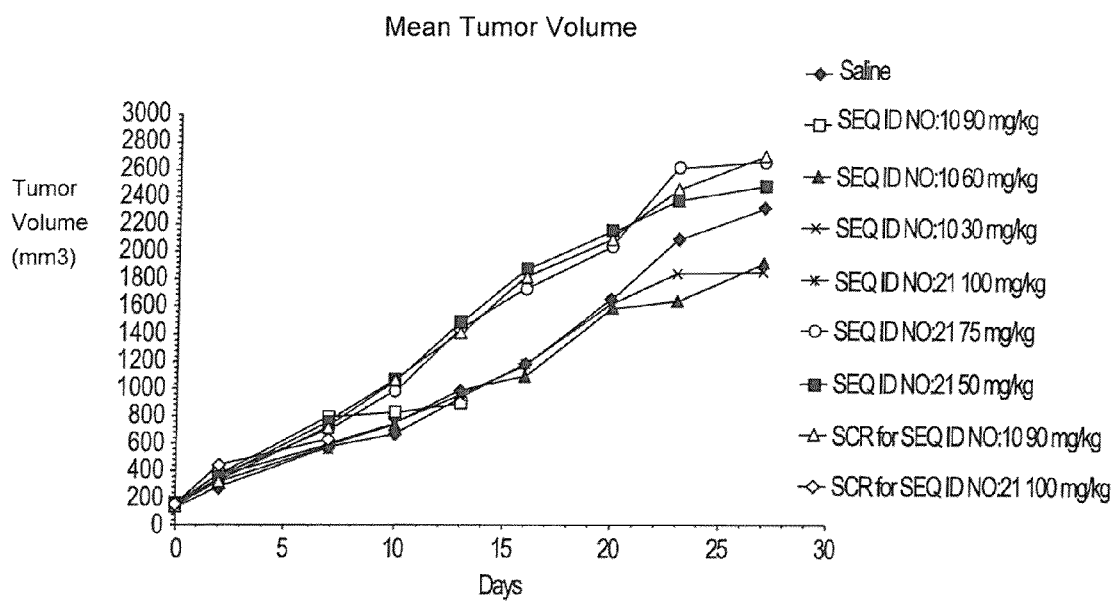
FIG. 18: In vivo Inhibition of tumor growth.

Effect of antisense oligonucleotide on tumor growth (FIG. 18): Six to seven week old male athymic nu/nu mice (Harlan Sprague Dawley) weighing an average of 27.3±2.4 g were used in the study. Ten million cells of 22RV1 (androgen-independent prostate cancer line) were suspended in PBS (Gibco#14190) and Matrigel (BD#356234) with a ratio of 1:1 were injected subcutaneously into each mouse. When tumors reach an average volume of 150-200 mm$^3$, the mice were divided into nine experimental groups. Two hundred μl of oligo was injected intravenously when the average tumor size reached 152.66±27.97 mm$^3$. Oligos were given every 3 days for a total of 5 times. The control vehicles were given the same regime as the oligos. The tumor volumes for each mouse were determined by measuring two dimensions with calipers and calculated using the formula: tumor volume=(length×width$^2$)/2).

Example 14

Preparation of Conjugates of Oligomers with Polyethylene Glycol

The oligomers having sequences shown as SEQ ID NO: 48 or SEQ ID NO: 63 are functionalized on the 5' terminus by attaching an aminoalkyl group, such as hexan-1-amine blocked with a blocking group such as Fmoc to the 5' phosphate groups of the oligomers using routine phosphoramidite chemistry, oxidizing the resultant compounds, deprotecting them and purifying them to achieve the functionalized oligomers, respectively, having the formulas (IA) and (IB):

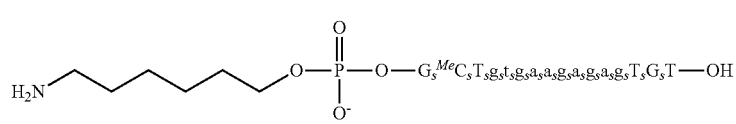

(IA)

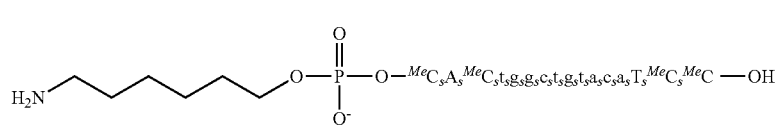

(IB)

wherein the bold uppercase letters represent nucleoside analogue monomers, lowercase letters represent DNA monomers, the subscript "s" represents a phosphorothioate linkage, and $^{Me}C$ represents 5-methylcytosine.

A solution of activated PEG, such as the one shown in formula (II):

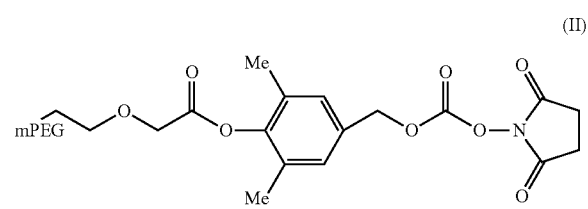

(II)

wherein the PEG moiety has an average molecular weight of 12,000, and each of the compounds of formulas (IA) and (IB) in PBS buffer are stirred in separate vessels at room temperature for 12 hours. The reaction solutions are extracted three times with methylene chloride and the combined organic layers are dried over magnesium sulphate and filtered and the solvent is evaporated under reduced pressure. The resulting residues are dissolved in double distilled water and loaded onto an anion exchange column. Unreacted PEG linker is eluted with water and the products are eluted with $NH_4HCO_3$ solution. Fractions containing pure products are pooled and lypophilized to yield the conjugates SEQ ID NOs: 48 and 63, respectively as show in formulas (IIIA) and (IIIB):

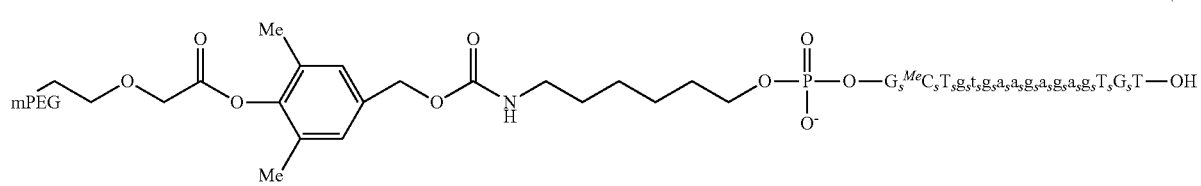

(IIIA)

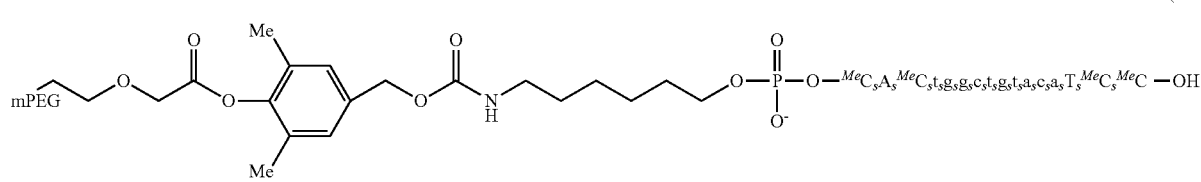

(IIIB)

wherein each of the oligomers of SEQ ID NOs: 48 and 63 is attached to a PEG polymer having average molecular weight of 12,000 via a releasable linker.

Chemical structures of PEG polymer conjugates that can be made with oligomers having sequences shown in SEQ ID NOs: 51, 58 and 77 using the process described above are respectively shown in formulas (IVA), (IVB) and (IVC):

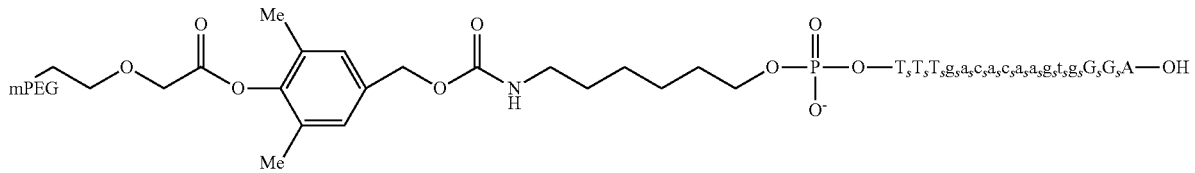

(IVA)

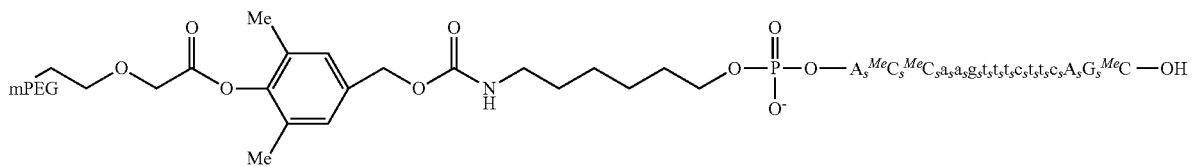

(IVB)

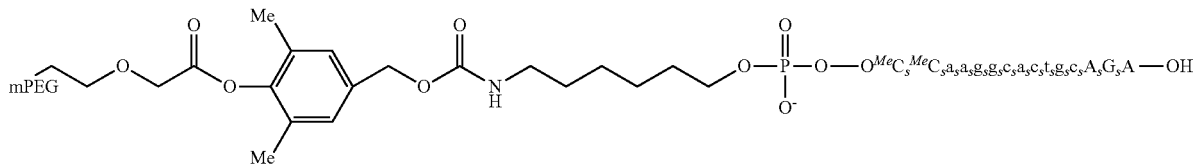

(IVC)

wherein bold uppercase letters represent beta-D-oxy-LNA monomers, lowercase letters represent DNA monomers, the subscript "s" represents a phosphorothioate linkage and $^{Me}C$ represent 5-methylcytosine.

Activated oligomers that can be used in this process to respectively make the conjugates shown in formulas (IVA), (IVB) and (IVC) have the chemical structures shown in formulas (VA), (VB) and (VC):

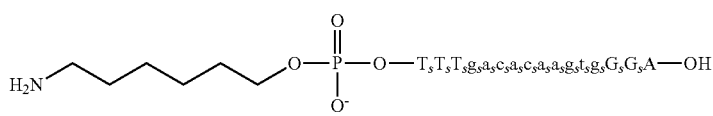

(VA)

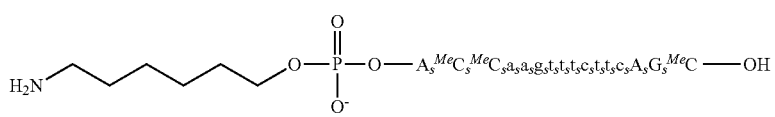

(VB)

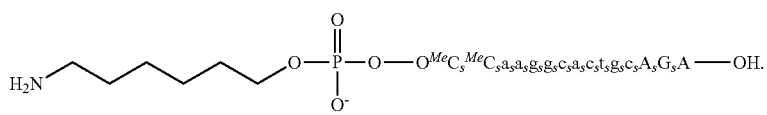

(VC)

Diarylhydantoin Androgen Receptor Ligand Binding Inhibitors

Diarylhydantoin derivative androgen receptor ligand binding inhibitors that may be used in combination with AR antisense oligomers according to the invention include those disclosed in U.S. Pat. No. 7,709,517 which is incorporated by reference in its entirety as if fully set forth herein.

Preferred diarylhydantoin androgen receptor ligand binding inhibitors for use according to the invention include, for example the following diarylthiohydantoin compounds:

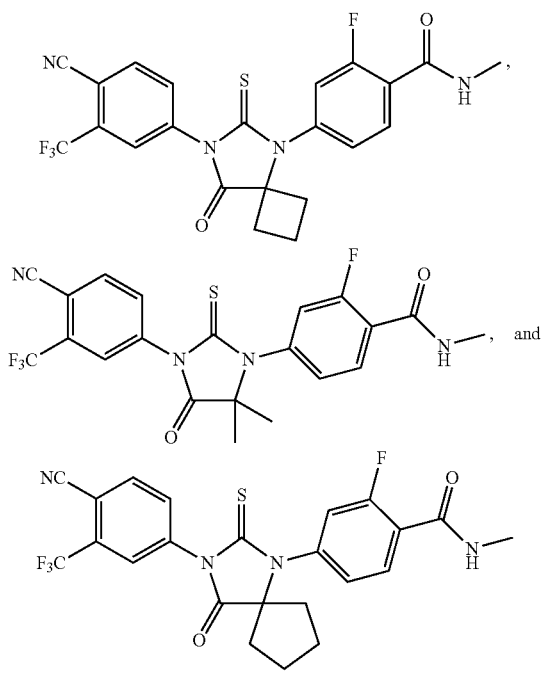

or a pharmaceutically acceptable salt thereof.

The compounds of the invention are useful as pharmaceutical compositions prepared with a therapeutically effective amount of a compound of the invention, as defined herein, and a pharmaceutically acceptable carrier or diluent.

The diarylhydantoin compounds may, for example, be formulated as pharmaceutical compositions and administered to a subject in need of treatment, for example a mammal, such as a human patient, in a variety of forms adapted to the chosen route of administration, for example, orally, nasally, intraperitoneally, or parenterally, by intravenous, intramuscular, topical or subcutaneous routes, or by injection into tissue.

Thus, diarylhydantoin compounds used according to the invention may be systemically administered, e.g., orally, in combination with a pharmaceutically acceptable vehicle such as an inert diluent or an assimilable edible carrier; or by inhalation or insufflation. They may be enclosed in hard or soft shell gelatin capsules, may be compressed into tablets, or may be incorporated directly with the food of the patient's diet. For oral therapeutic administration, the diarylhydantoin compounds may be combined with one or more excipients and used in the form of ingestible tablets, buccal tablets, troches, capsules, elixirs, suspensions, syrups, wafers, and the like. The diarylhydantoin compounds may be combined with a fine inert powdered carrier and inhaled by the subject or insufflated. Such compositions and preparations should contain at least 0.1% diarylhydantoin compounds. The percentage of the compositions and preparations may, of course, be varied and may conveniently be between about 2% to about 60% of the weight of a given unit dosage form. The amount of diarylhydantoin compounds in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the diarylhydantoin compounds may be incorporated into sustained-release preparations and devices. For example, the diarylhydantoin compounds may be incorporated into time release capsules, time release tablets, and time release pills.

The diarylhydantoin compounds may also be administered intravenously or intraperitoneally by infusion or injection. Solutions of the diarylhydantoin compounds can be prepared in water, optionally mixed with a nontoxic surfactant. Dispersions may also be prepared in glycerol, liquid polyethylene glycols, triacetin, and mixtures thereof and in oils. Under ordinary conditions of storage and use, these preparations may contain a preservative to prevent the growth of microorganisms.

The pharmaceutical dosage forms suitable for injection or infusion can include sterile aqueous solutions or dispersions or sterile powders comprising the diarylhydantoin compounds which are adapted for the extemporaneous preparation of sterile injectable or infusible solutions or dispersions, optionally encapsulated in liposomes. The ultimate dosage, form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms may be brought about by various antibacterial and antifungal agents, for example, parabens, chlorobutanol, phenol, sorbic acid, thimerosal, and the like. It may be preferable to include isotonic agents, for example, sugars, buffers or sodium chloride. Prolonged absorption of the injectable compositions may be brought about by the use in the compositions of agents delaying absorption, for example, aluminum monostearate and gelatin.

Sterile injectable solutions may be prepared by incorporating the diarylhydantoin compounds in the required amount in the appropriate solvent with, for example, various of the other ingredients enumerated above, as required, followed by filter sterilization. In the case of sterile powders for the preparation of sterile injectable solutions, the preferred methods of preparation include vacuum drying and freeze drying techniques, which yield a powder of the active ingredient plus any additional desired ingredient present in the previously sterile-filtered solutions.

Useful dosages of the compounds of the diarylhydantoin compounds can be determined by comparing their in vitro activity, and in vivo activity in animal models. Methods for the extrapolation of effective dosages in mice, and other animals, to humans are known to the art; for example, see U.S. Pat. No. 4,938,949, which is hereby incorporated by reference.

For example, the concentration of the diarylhydantoin compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

The amount of the diarylhydantoin compounds and antisense AR oligomers required for use in treatment may vary not only with the particular salt selected but also with the route of administration, the nature of the condition being treated and the age and condition of the patient and will be ultimately at the discretion of the attendant physician or clinician.

Effective dosages and routes of administration of agents of the diarylhydantoin compounds may, for example, be conventional. The exact amount (effective dose) of the agent may vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen for the diarylhydantoin compounds may be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 1 mg/kg, 10 mg/kg, or 50 mg/kg of body weight per day.

The diarylhydantoin compounds are conveniently administered in unit dosage form; for example, containing 0.05 to 10000 mg, 0.5 to 10000 mg, 5 to 1000 mg, or about 100 mg of active ingredient per unit dosage form.

The diarylhydantoin compounds may be administered to achieve peak plasma concentrations of, for example, from about 0.5 to about 75 µM, about 1 to 50 µM, about 2 to about 30 µM, or about 5 to about 25 µM. Exemplary desirable plasma concentrations include at least or no more than 0.25, 0.5, 1, 5, 10, 25, 50, 75, 100 or 200 µM. For example, plasma levels may be from about 1 to 100 micromolar or from about 10 to about 25 micromolar. This may be achieved, for example, by the intravenous injection of a 0.05 to 5% solution of the diarylhydantoin compounds, optionally in saline, or orally administered as a bolus containing about 1-100 mg of the diarylhydantoin compounds. Desirable blood levels may be maintained by continuous infusion to provide about 0.00005-5 mg per kg body weight per hour, for example at least or no more than 0.00005, 0.0005, 0.005, 0.05, 0.5, or 5 mg/kg/hr. Alternatively, such levels can be obtained by intermittent infusions containing about 0.0002-20 mg per kg body weight, for example, at least or no more than 0.0002, 0.002, 0.02, 0.2, 2, 20, or 50 mg of the diarylhydantoin compounds per kg of body weight.

The diarylhydantoin compounds may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

Combination Therapy Experiments

Figure 19:
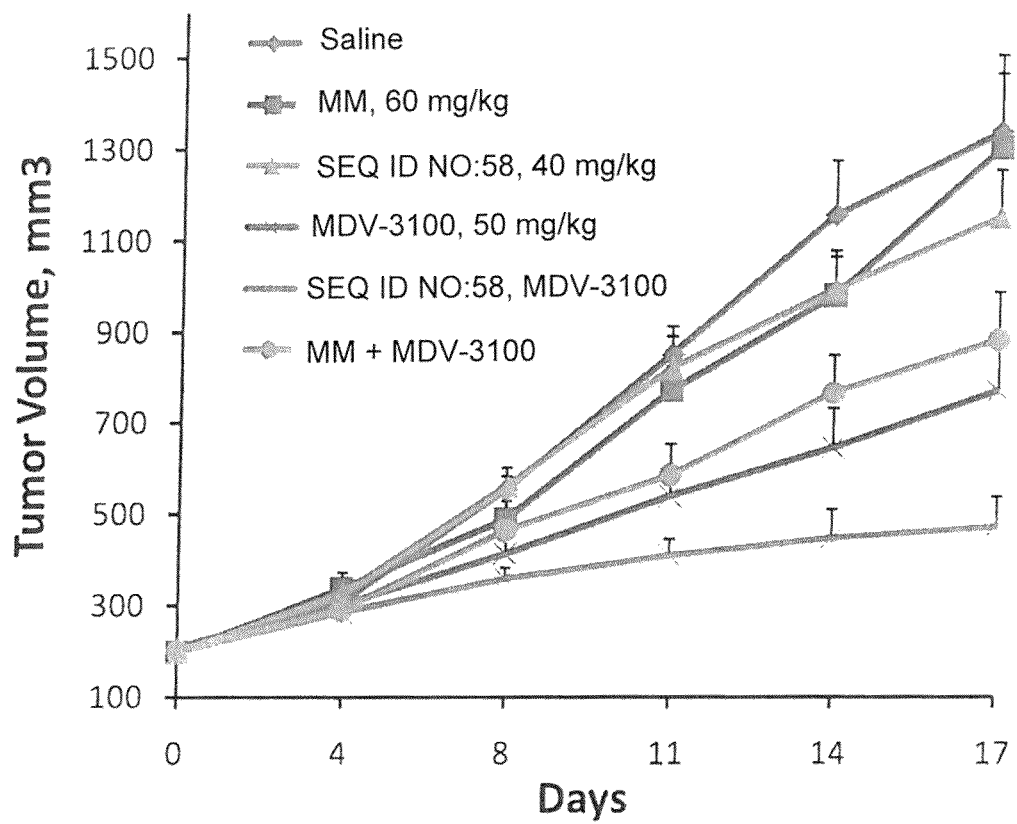
FIG. 19: Tumor volume measured over a 17-day period for antisense mismatch control, SEQ ID NO:58 alone, MDV3100 alone, SEQ ID NO:58+MDV3100, and antisense mismatch+MDV3100 treatment groups in the CWR-22 prostate tumor cell xenograft model FIG. 20 Tumor volume measured over a 31 day period for MDV3100 alone versus MDV3100+SEQ ID NO: 58 combination treatment groups in the CWR-22 tumor cell tumor xenograft model.
Figure 20:
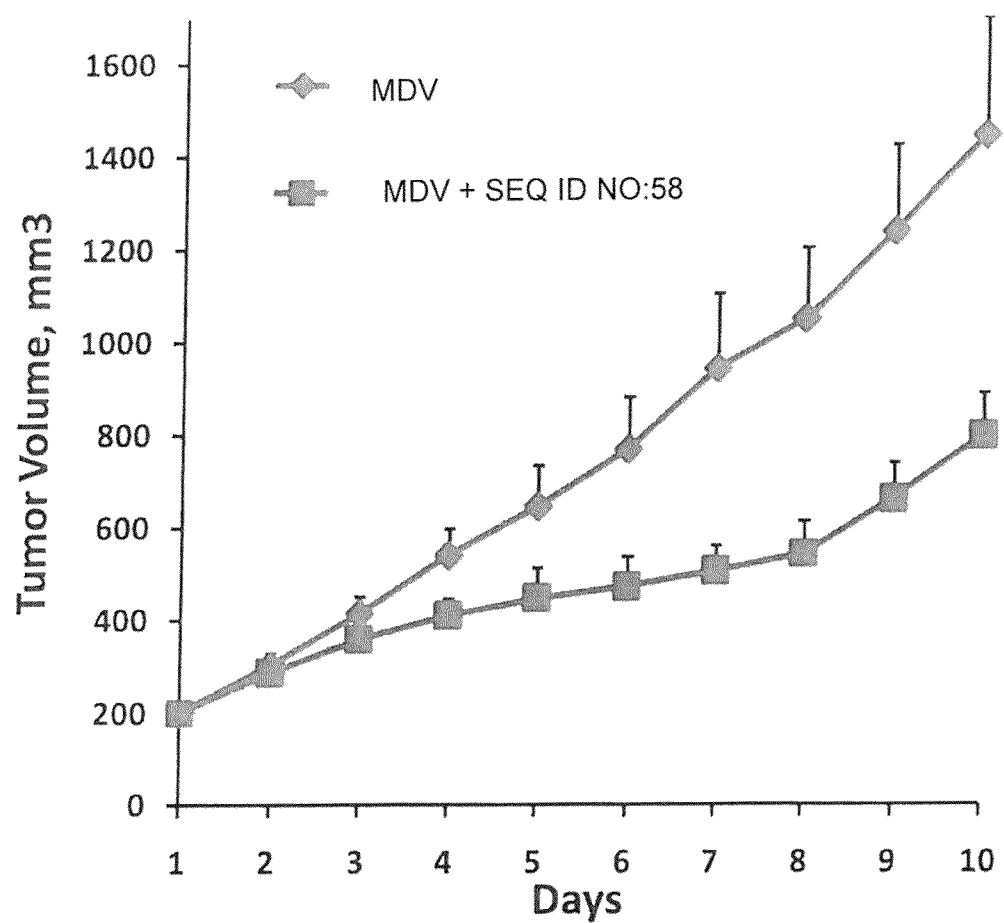

In vivo therapeutic efficacy of combination treatment with antisense oligomers and diarylhydantoin AR binding inhibitors was evaluated. A combination study with SEQ ID NO:58 and the diarylhydantoin androgen receptor binding inhibitor 4-(3-(4-cyano-3-(trifluoromethyl)phenyl)-5,5-dimethyl-4-oxo-2-thioxoimidazolidin-1-yl)-2-fluoro-N-methylbenzamide (MDV3100) was carried out in the androgen-dependent CWR-22 human prostate tumor cell line mouse xenograft model, as shown in FIGS. 19 and 20. A mismatch oligomer control ("MM-oligo") having the sequence 5'-$A_sC_sC_sg_sa_s$-$t_st_sc_sa_sc_st_st_st_sA_sG_sC$-3' (SEQ ID NO:107) was used as indicated (mismatched bases indicated in italics; this sequence does not have 100% match with any mRNA in the mouse or human database). Mice were purposely dosed with a low dose of SEQ ID NO:58 (40 mg/kg, q3dx4, i.v.), which showed minimum or no significant tumor growth inhibition (TGI) by itself in this experiment. In contrast, 50% TGI was observed with 50 mg/kg MDV3100 (qdx11, p.o.) on Day 17. In the combination treatment groups, SEQ ID NO:58 with 50 mg/kg MDV3100, TGI increased to 76%. Since the tumor size exceeded the allowable limit (1690 mm$^3$) in the vehicle control group on day 17, animals in this group were euthanized, which precluded further meaningful TGI calculations. Nevertheless, as shown in FIG. 20, animals were monitored for tumor growth until day 31 demonstrating 100% survival in the MDV3100 group and the SEQ ID NO:58+MDV3100 combination group. FIG. 20 further shows that, in the combination group, a marked inhibition of tumor growth is observed when compared to animals treated only with MDV3100. This experiment was also been repeated in two independent studies, yielding similar results.

Figure 21A:
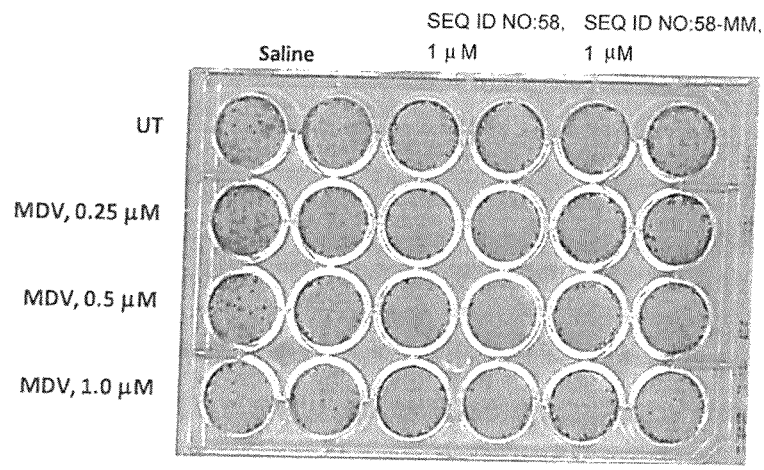
FIG. 21: SEQ ID NO: 58 potentiates the cell growth inhibitory effect of MDV3100.
Figure 21B:
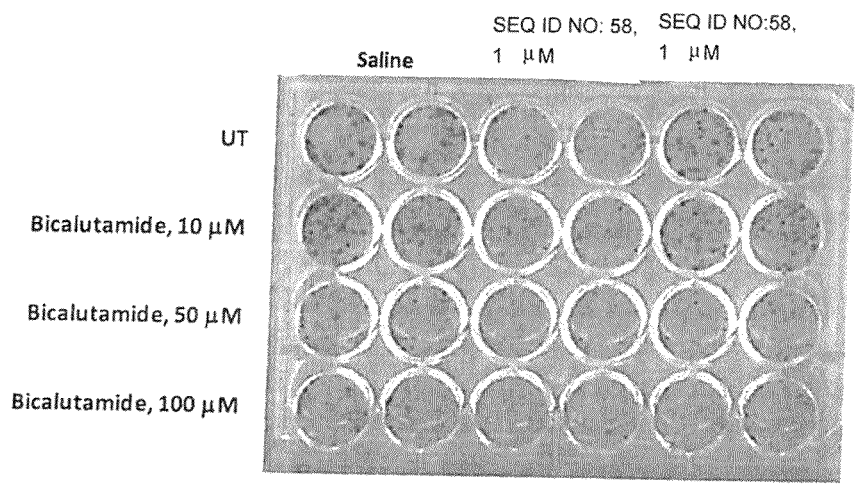

FIG. 21A shows effect of the combination of SEQ ID NO:58 and MDV3100 in a colony formation growth assay using the AR-positive, androgen-resistant human cell line, C4-2b-AR. SEQ ID NO:58 or MDV3100 alone showed dose-dependent growth inhibition. However, when combined, growth of colonies was inhibited more effectively than either agent alone. As shown in FIG. 21B, a similar result was obtained when SEQ ID NO:58 was combined with bicalutamide, but only at a higher concentration. In the experiment, C4-2b cells were plated at 400 cells/well in a 24-well plate. 24 hours later, cells were treated with test compounds continuously for 12 days when MTT (100 µL of 5 mg/mL) was added to 1 mL of culture and incubated until a visible darker blue color became apparent. The supernatant was removed to allow the colonies to dry, after which the plate was scanned. FIG. 21A shows results for SEQ ID NO:58 (indicated EZN-4176) and MDV3100. FIG. 21B shows results for SEQ ID NO:58 (indicated EZN-4176) and bicalutamide.

Figure 22:
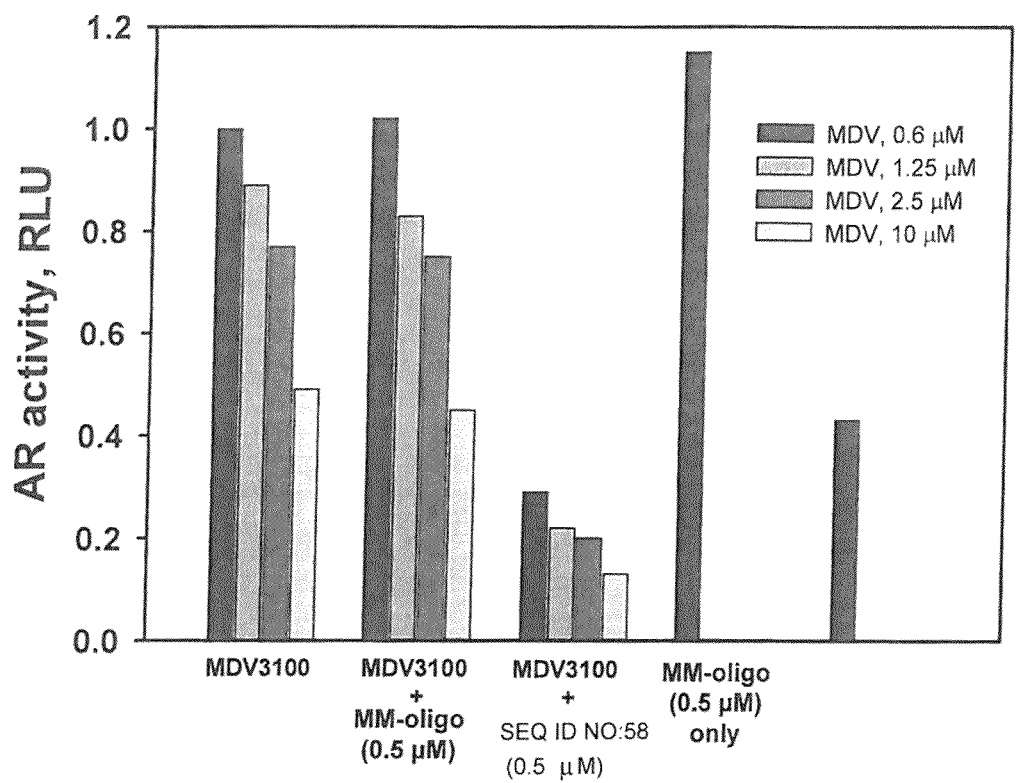
FIG. 22: SEQ ID NO: 58 potentiates MDV3100 inhibition of AR transcriptional activity.

As shown in FIG. 22, the combination of SEQ ID NO:58 with MDV3100 demonstrated better inhibition of AR transcriptional activity in an AR-positive, androgen-resistant human cell line, C4-2b-AR-luc (luciferase marker of AR transcription), compared with either agent used alone. These results suggest that the demonstrated synergistic potentiation of in vivo tumor growth obtained when SEQ ID NO:58 was used in combination with MDV3100 results from a direct effect on the tumor cells. In the experiment, $C_4$-2b-AR-luc cells were plated in 96-well plate and treated with SEQ ID NO:58 or MM-oligo for 5 days followed with various concentrations of MDV3100 as marked and 10 nM DHT. Luciferase activity was determined after 24 hours. Each bar represents results in duplicates.

MDV3100 has demonstrated antitumor effects in castration-resistant prostate cancer (CRPC) patients since it decreased serum PSA by 50% or more in 56% of patients, induced responses in soft tissue in 22% of patients, stabilized bone disease in 56% of patients, and reduced circulating tumor cell counts in 49% of patients (Scher et al., Lancet 375, 1437 (Apr. 24, 2010). Nevertheless, a certain population of patients failed initially to respond to MDV3100 and the median time to progression was approximately 47 weeks. Not only can resistance to MDV3100 occur, but MDV3100, which competes with androgen for the ligand-binding domain of the AR, may be less effective on AR variants devoid of the ligand-binding domain. Such variants have already been documented in prostate cancer patients. Therefore, in view of the findings presented here, it is believed that combination treatment with an antisense oligomer targeting AR, such as SEQ ID NO:58, and diarylhydantoin AR binding inhibitor, such as MDV3100, represents a significant advance in the treatment of prostate cancer, for both first line and salvage therapy, and other androgen receptor activity dependent disorders.

Medical Indications

Generally stated, one aspect of the invention is directed to a method of treating a mammal, such as a human, suffering from or susceptible to conditions associated with abnormal levels of androgen receptor activity, for example as a result of overexpression of or mutation of AR, that includes administering to the mammal and antisense oligomer targeted to AR, for example, one comprised solely of DNA rather than RNA and including one or more LNA DNA monomers, or a derivative thereof, such as those described herein, for example, in the form of a pharmaceutical composition, for example via intravenous administration, and a diarylhydantoin type androgen receptor ligand binding inhibitor or pharmaceutically acceptable salt thereof including, for example, those described herein and those disclosed in U.S. Pat. No. 7,709,517, for example by oral administration or by intravenous administration or bolus injection.

The disorder may, for example, be a cancer such as breast cancer or prostate cancer, for example, advanced prostate cancer, castration-resistant prostate cancer, LHRH-resistant prostate cancer, androgen-sensitive prostate cancer, and androgen-insensitive prostate cancer, benign prostatic hyperplasia, AR-activity dependent breast cancer, alopecia, spinal and muscular atrophy, Kennedy disease and polyglutamate disease.

The antisense oligomer may optionally be linked to a ligand or conjugate. For example, in order to increase the cellular uptake of the oligomer. In some embodiments the conjugate is a sterol, such as cholesterol. However, it has been found that the LNA antisense oligomers disclosed herein advantageously do not require conjugation for in vivo therapeutic use in mammals.

Alternatively stated, the invention is furthermore directed to a method for treating abnormal levels of androgen receptor activity, said method comprising administering an antisense oligomer of the invention, or a conjugate of the oligomer or a pharmaceutical composition of the oligomer or conjugate to a patient, such as a human or non-human mammal, in need thereof and further comprising the administration of and a diarylhydantoin type androgen receptor ligand binding inhibitor or pharmaceutically acceptable salt thereof including, for example, those described herein and those disclosed in U.S. Pat. No. 7,709,517. Said further administration may be such that the further chemotherapeutic agent is conjugated to the antisense oligomer, is present in the pharmaceutical composition, or is administered in a separate formulation.

The combination methods of treatment according to the invention may be employed, for example, for at least one week, such as one week, for at least two weeks, such as two weeks, for at least one month, such as one month, for at least two months, such as two, three, four, five or six months, or longer than six months, such as one year. The administration of antisense AR oligomer and antiandrogen compound may at least sometimes occur of the same days or may not occur on the same days; what is important is that each of the agents is present at the same time in the mammal subject. Because of the relatively long duration of the antisense AR oligomers of the invention in mammals, one manner of dosing that may, for example, be employed, involves less frequent dosing of the antisense oligomer than the antiandrogen compound. For example, antisense AR oligomer may be administered to the subject biweekly, weekly, every two weeks, or monthly, while the antiandrogen compound, such as MDV3100, is administered daily or every two days. Those skilled in the art will recognize that many dosing regimens are possible for the combination therapy embodiments of the invention and that the use of depot formulations is also possible.

Furthermore, the invention provides a method of regulating genes, and their respective mRNA and protein products, which are modulated by the androgen receptor (i.e androgen receptor targets) such as genes, mRNA and/or proteins selected form the group consisting of: Protein kinase C delta (PRKCD), Glutathione S-transferase theta 2 (GSTT2), transient receptor potential cation channel subfamily V member 3 (TRPV3), Pyrroline-5-carboxylate reductase 1 (PYCR1) or ornithine aminotransferase (OAT), said methods including the step of administering to a mammal subject such as a human, an antisense oligomer targeting AR and a diarylhydantoin type androgen receptor ligand binding inhibitor or pharmaceutically acceptable salt thereof including, for example, those described herein and those disclosed in U.S. Pat. No. 7,709,517, in amounts effective together to regulate expression of one or more androgen receptor modulated genes, such as those described.

Each of the patents, patent applications and other publications cited in this disclosure is incorporated by reference in its entirety.

Although the foregoing description is directed to the preferred embodiments of the invention, it is noted that other variations and modifications may be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A method for treating prostate cancer in a mammal, comprising the steps of:
   administering to a mammal in need of treatment for prostate cancer in amounts therapeutically effective in combination,
   (a) an antisense oligomer comprising:

$$5'-A_s{}^{Me}C_s{}^{Me}C_sa_sa_sg_st_st_sc_st_sc_sA_sG_s{}^{Me}C-3'$$ (SEQ ID NO: 58)

wherein uppercase letters denote beta-D-oxy-LNA monomers and lowercase letters denote DNA monomers, the subscript "s" denotes a phosphorothioate linkage, and $^{Me}C$ denotes a beta-D-oxy-LNA monomer containing a 5-methylcytosine base, or a conjugate of said oligomer, or a pharmaceutically acceptable salt of said compound or said conjugate; and
   (b) the compound bicalutamide,
   or a pharmaceutically acceptable salt thereof.

2. The method of claim 1, wherein the mammal is a human.

3. The method of claim 1, wherein the prostate cancer is castration-resistant prostate cancer.

4. The method of claim 1, wherein the prostate cancer is advanced prostate cancer.

5. A method for treating prostate cancer in a mammal, comprising the steps of:
   administering to a mammal in need of treatment for prostate cancer in amounts therapeutically effective in combination,
   (a) an antisense oligomer comprising:

$$5'-{}^{Me}C_s{}^{Me}C_s{}^{Me}C_sa_sa_sg_sg_sc_sa_sc_st_sg_sc_sA_sG_sA-3'$$ (SEQ ID NO: 77)

wherein uppercase letters denote beta-D-oxy-LNA monomers and lowercase letters denote DNA monomers, the subscript "s" denotes a phosphorothioate linkage, and $^{Me}C$ denotes a beta-15 D-oxy-LNA monomer containing a 5-methylcytosine base, or a conjugate of said oligomer, or a pharmaceutically acceptable salt of said compound or said conjugate; and
   (b) the compound bicalutamide,
   or a pharmaceutically acceptable salt thereof.

6. The method of claim 5, wherein the mammal is a human.

7. The method of claim 5, wherein the prostate cancer is castration-resistant prostate cancer.

8. The method of claim 5, wherein the prostate cancer is advanced prostate cancer.

\* \* \* \* \*

SEQUENCE LISTING

<160> NUMBER OF SEQ ID NOS: 107

<210> SEQ ID NO 1
<211> LENGTH: 4314
<212> TYPE: DNA
<213> ORGANISM: homo sapiens

<400> SEQUENCE: 1

```
cgagatcccg gggagccagc ttgctgggag agcgggacgg tccggagcaa gcccagaggc      60
agaggaggcg acagagggaa aaagggccga gctagccgct ccagtgctgt acaggagccg     120
aagggacgca ccacgccagc cccagcccgg ctccagcgac agccaacgcc tcttgcagcg     180
cggcggcttc gaagccgccg cccggagctg ccctttcctc ttcggtgaag tttttaaaag     240
ctgctaaaga ctcggaggaa gcaaggaaag tgcctggtag gactgacggc tgcctttgtc     300
ctcctcctct ccaccccgcc tcccccaccc ctgccttccc ccctcccccc gtcttctctc     360
ccgcagctgc ctcagtcggc tactctcagc caaccccccct caccacccctt ctccccaccc     420
gcccccccgc cccgtcggc ccagcgctgc cagcccgagt ttgcagagag gtaactccct     480
ttggctgcga gcgggcgagc tagctgcaca ttgcaaagaa ggctcttagg agccaggcga     540
ctggggagcg gcttcagcac tgcagccacg acccgcctgg ttaggctgca cgcggagaga     600
accctctgtt ttccccccact ctctctccac ctcctcctgc cttccccacc ccgagtgcgg     660
agccagagat caaagatgca aaaggcagtc aggtcttcag tagccaaaaa acaaaacaaa     720
caaaaacaaa aagccgaaa taaagaaaaa agataataac tcagttctta tttgcaccta     780
cttcagtgga cactgaattt ggaaggtgga ggattttgtt ttttctttt aagatctggg     840
catcttttga atctacccctt caagtattaa gagacagact gtgagcctag cagggcagat     900
cttgtccacc gtgtgtcttc ttctgcacga gactttgagg ctgtcagagc gcttttttgcg     960
tggttgctcc cgcaagtttc cttctctgga gcttcccgca ggtgggcagc tagctgcagc    1020
gactaccgca tcatcacagc ctgttgaact cttctgagca agagaagggg aggcggggta    1080
agggaagtag gtggaagatt cagccaagct caaggatgga agtgcagtta gggctgggaa    1140
gggtctaccc tcggccgccg tccaagacct accgaggagc tttccagaat ctgttccaga    1200
gcgtgcgcga agtgatccag aacccgggcc ccaggcaccc agaggccgcg agcgcagcac    1260
ctcccggcgc cagtttgctg ctgctgcagc agcagcagca gcagcagcag cagcagcagc    1320
agcagcagca gcagcagcag cagcagcagc agcaagagac tagcccccagg cagcagcagc    1380
agcagcaggg tgaggatggt tctccccaag cccatcgtag aggccccaca ggctacctgg    1440
tcctggatga ggaacagcaa ccttcacagc cgcagtcggc cctggagtgc acccccgaga    1500
gaggttgcgt cccagagcct ggagccgccg tggccgccag caagggctg ccgcagcagc    1560
tgccagcacc tccggacgag gatgactcag ctgccccatc cacgttgtcc ctgctgggcc    1620
ccactttccc cggcttaagc agctgctccg ctgaccttaa agacatcctg agcgaggcca    1680
gcaccatgca actccttcag caacagcagc aggaagcagt atccgaaggc agcagcagcg    1740
ggagagcgag ggaggcctcg ggggctccca cttcctccaa ggacaattac ttaggggca    1800
cttcgaccat ttctgacaac gccaaggagt tgtgtaaggc agtgtcggtg tccatgggcc    1860
tgggtgtgga ggcgttggag catctgagtc caggggaaca gcttcggggg gattgcatgt    1920
acgccccact ttgggagtt ccaccgctct tgcgtccac tccttgtgcc ccattggccg    1980
aatgcaaagg ttctctgcta gacgacagcg caggcaagag cactgaagat actgctgagt    2040
```

```
attcccctttt caagggaggt tacaccaaag ggctagaagg cgagagccta ggctgctctg    2100
gcagcgctgc agcagggagc tccgggacac ttgaactgcc gtctaccctg tctctctaca    2160
agtccggagc actggacgag gcagctgcgt accagagtcg cgactactac aactttccac    2220
tggctctggc cggaccgccg cccctccgc cgcctcccca tccccacgct cgcatcaagc     2280
tggagaaccc gctggactac ggcagcgcct gggcggctgc ggcggcgcag tgccgctatg    2340
gggacctggc gagcctgcat ggcgcgggtg cagcgggacc cggttctggg tcaccctcag    2400
ccgccgcttc ctcatcctgg cacactctct tcacagccga agaaggccag ttgtatggac    2460
cgtgtggtgg tggtggggt ggtggcgcg cggcggcgg cggcggcggc ggcggcggcg       2520
gcggcggcgg cggcgaggcg ggagctgtag cccctacgg ctacactcgg cccctcagg      2580 ggctggcggg ccaggaaagc gacttcaccg cacctgatgt gtggtaccct gcggcatgg     2640 tgagcagagt gccctatccc agtccactt gtgtcaaaag cgaaatgggc cctggatgg      2700 atagctactc cggaccttac ggggacatgc gtttggagac tgccagggac catgttttgc    2760
ccattgacta ttactttcca ccccagaaga cctgcctgat ctgtggagat gaagcttctg    2820
ggtgtcacta tggagctctc acatgtggaa gctgcaaggt cttcttcaaa agagccgctg    2880
aagggaaaca gaagtacctg tgcgccagca gaaatgattg cactattgat aaattccgaa    2940
ggaaaaattg tccatcttgt cgtcttcgga atgttatga agcagggatg actctgggag     3000
cccggaagct gaagaaactt ggtaatctga aactacagga ggaaggagag cttccagca    3060 ccaccagccc cactgaggag acaacccaga agctgacagt gtcacacatt gaaggctatg   3120
aatgtcagcc catcttcctg aatgtcctgg aagccattga gccaggtgta gtgtgtgctg   3180
gacacgacaa caaccagccc gactccttg cagccttgct ctctagcctc aatgaactgg    3240
gagagagaca gcttgtacac gtggtcaagt gggccaaggc cttgcctggc ttccgcaact   3300
tacacgtgga cgaccagatg gctgtcattc agtactcctg gatgggctc atggtgtttg    3360 ccatgggctg gcgatccttc accaatgtca actccaggat gctctacttc gcccctgatc    3420
tggttttcaa tgagtaccgc atgcacaagt cccggatgta cagccagtgt gtccgaatga    3480
ggcacctctc tcaagagttt ggatggctcc aaatcacccc caggaattc ctgtgcatga     3540 aagcactgct actcttcagc attattccag tggatgggct gaaaaatcaa aaattctttg    3600
atgaacttcg aatgaactac atcaaggaac tcgatcgtat cattgcatgc aaaagaaaaa    3660
atcccacatc ctgctcaaga cgcttctacc agctcaccaa gctcctggac tccgtgcagc    3720
ctattgcgag agagctgcat cagttcactt ttgacctgct aatcaagtca cacatggtga    3780
gcgtggactt tccggaaatg atggcagaga tcatctctgt gcaagtgccc aagatcctt     3840 ctgggaaagt caagcccatc tatttccaca cccagtgaag cattggaaac ctatttccc    3900 caccccagct catgcccct ttcagatgtc ttctgcctgt tataactctg cactactcct    3960
ctgcagtgcc ttgggaatt tcctctattg atgtacagtc tgtcatgaac atgttcctga    4020
attctatttg ctgggctttt tttttctctt tctctccttt cttttcttc ttccctccct    4080 atctaaccct cccatggcac cttcagactt tgcttcccat tgtggctcct atctgtgttt    4140
tgaatggtgt tgtatgcctt taaatctgtg atgatcctca tatggcccag tgtcaagttg    4200
tgcttgttta cagcactact ctgtgccagc cacacaaacg tttacttatc ttatgccacg    4260
ggaagtttag agagctaaga ttatctgggg aaatcaaaac aaaaacaagc aaac          4314

<210> SEQ ID NO 2
<211> LENGTH: 16
<212> TYPE: DNA
```

```
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 2
gagaaccatc ctcacc                                                       16

<210> SEQ ID NO 3
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 3
ggaccaggta gcctgt                                                       16

<210> SEQ ID NO 4
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 4
cccctggact cagatg                                                       16

<210> SEQ ID NO 5
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 5
gcacaaggag tgggac                                                       16

<210> SEQ ID NO 6
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 6
gctgtgaaga gagtgt                                                       16
```

```
<210> SEQ ID NO 7
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 7
tttgacacaa gtggga                                                   16

<210> SEQ ID NO 8
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 8
gtgacaccca gaagct                                                   16

<210> SEQ ID NO 9
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 9
catccctgct tcataa                                                   16

<210> SEQ ID NO 10
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 10
accaagtttc ttcagc                                                   16

<210> SEQ ID NO 11
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
```

-continued phosphorothioate

<400> SEQUENCE: 11
cttggcccac ttgacc                                                16

<210> SEQ ID NO 12
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 12
tcctggagtt gacatt                                                16

<210> SEQ ID NO 13
<211> LENGTH: 16
<212> TYPE: DNA
<213> ORGANISM: artificial
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 13
cactggctgt acatcc                                                16

<210> SEQ ID NO 14
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 14
catccaaact cttgag                                                16

<210> SEQ ID NO 15
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 15
gctttcatgc acagga                                                16

<210> SEQ ID NO 16
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:

<221> NAME/KEY: misc_feature
<222> LOCATION: (1)..(16)
<223> OTHER INFORMATION: nucleotide or nucleotide analogues - optionally
      phosphorothioate

<400> SEQUENCE: 16
gaagttcatc aaagaa                                                       16

<210> SEQ ID NO 17
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 17
agttccttga tgtagt                                                       16

<210> SEQ ID NO 18
<211> LENGTH: 16
<212> TYPE: DNA
<213> ORGANISM: artificial
<220> FEATURE:
<223> OTHER INFORMATION: LNA oligomer Sequence/oligomer Sequence motif

<400> SEQUENCE: 18
ttgcacagag atgatc                                                       16

<210> SEQ ID NO 19
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 19
gatgggcttg actttc                                                       16

<210> SEQ ID NO 20
<211> LENGTH: 16
<212> TYPE: DNA
<213> ORGANISM: artificial
<220> FEATURE:
<223> OTHER INFORMATION: LNA oligomer Sequence/oligomer Sequence motif

<400> SEQUENCE: 20
caggcagaag acatct                                                       16

<210> SEQ ID NO 21
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate -continued

```
<400> SEQUENCE: 21
cccaaggcac tgcaga                                                    16

<210> SEQ ID NO 22
<211> LENGTH: 16
<212> TYPE: DNA
<213> ORGANISM: artificial
<220> FEATURE:
<223> OTHER INFORMATION: LNA oligmer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 22
gctgacattc atagcc                                                    16

<210> SEQ ID NO 23
<211> LENGTH: 16
<212> TYPE: DNA
<213> ORGANISM: artificial
<220> FEATURE:
<223> OTHER INFORMATION: LNA oligmer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 23
gagaaccatc ctcacc                                                    16

<210> SEQ ID NO 24
<211> LENGTH: 16
<212> TYPE: DNA
<213> ORGANISM: artificial
<220> FEATURE:
<223> OTHER INFORMATION: LNA oligmer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 24
ggaccaggta gcctgt                                                    16

<210> SEQ ID NO 25
<211> LENGTH: 16
<212> TYPE: DNA
<213> ORGANISM: artificial
<220> FEATURE:
<223> OTHER INFORMATION: LNA oligmer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 25
cccctggact cagatg                                                    16

<210> SEQ ID NO 26
<211> LENGTH: 16
<212> TYPE: DNA
<213> ORGANISM: artificial
<220> FEATURE:
<223> OTHER INFORMATION: LNA oligmer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate
```

-continued

```
<400> SEQUENCE: 26
gcacaaggag tgggac                                                      16

<210> SEQ ID NO 27
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 27
gctgtgaaga gagtgt                                                      16

<210> SEQ ID NO 28
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 28
tttgacacaa gtggga                                                      16

<210> SEQ ID NO 29
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 29
gtgacaccca gaagct                                                      16

<210> SEQ ID NO 30
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 30
catccctgct tcataa                                                      16

<210> SEQ ID NO 31
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate
```

```
<400> SEQUENCE: 31
accaagtttc ttcagc                                              16

<210> SEQ ID NO 32
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 32
cttggcccac ttgacc                                              16

<210> SEQ ID NO 33
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 33
tcctggagtt gacatt                                              16

<210> SEQ ID NO 34
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 34
cactggctgt acatcc                                              16

<210> SEQ ID NO 35
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 35
catccaaact cttgag                                              16

<210> SEQ ID NO 36
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate
```

-continued

```
<400> SEQUENCE: 36
gctttcatgc acagga                                                    16

<210> SEQ ID NO 37
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 37
gaagttcatc aaagaa                                                    16

<210> SEQ ID NO 38
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 38
agttccttga tgtagt                                                    16

<210> SEQ ID NO 39
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 39
ttgcacagag atgatc                                                    16

<210> SEQ ID NO 40
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 40
gatgggcttg actttc                                                    16

<210> SEQ ID NO 41
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate
```

```
<400> SEQUENCE: 41
caggcagaag acatct                                                    16

<210> SEQ ID NO 42
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 42
cccaaggcac tgcaga                                                    16

<210> SEQ ID NO 43
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 43
gctgacattc atagcc                                                    16

<210> SEQ ID NO 44
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 44
gagaaccatc ctcacc                                                    16

<210> SEQ ID NO 45
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 45
ggaccaggta gcctgt                                                    16

<210> SEQ ID NO 46
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate
```

```
<400> SEQUENCE: 46
cccctggact cagatg                                                    16

<210> SEQ ID NO 47
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 47
gcacaaggag tgggac                                                    16

<210> SEQ ID NO 48
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 48
gctgtgaaga gagtgt                                                    16

<210> SEQ ID NO 49
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 49
ctgtgaagag agtg                                                      14

<210> SEQ ID NO 50
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 50
tgtgaagaga gt                                                        12

<210> SEQ ID NO 51
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate
```

-continued

<400> SEQUENCE: 51
tttgacacaa gtggga                                                                 16

<210> SEQ ID NO 52
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 52
ttgacacaag tggg                                                                   14

<210> SEQ ID NO 53
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 53
tgacacaagt gg                                                                     12

<210> SEQ ID NO 54
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 54
gtgacaccca gaagct                                                                 16

<210> SEQ ID NO 55
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 55
tgacacccag aagc                                                                   14

<210> SEQ ID NO 56
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

```
<400> SEQUENCE: 56
gacacccaga ag                                                        12

<210> SEQ ID NO 57
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 57
catccctgct tcataa                                                    16

<210> SEQ ID NO 58
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 58
accaagtttc ttcagc                                                    16

<210> SEQ ID NO 59
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 59
ccaagtttct tcag                                                      14

<210> SEQ ID NO 60
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 60
caagtttctt ca                                                        12

<210> SEQ ID NO 61
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate
```

```
<400> SEQUENCE: 61
cttggcccac ttgacc                                                    16

<210> SEQ ID NO 62
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 62
tcctggagtt gacatt                                                    16

<210> SEQ ID NO 63
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 63
cactggctgt acatcc                                                    16

<210> SEQ ID NO 64
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 64
actggctgta catc                                                      14

<210> SEQ ID NO 65
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 65
ctggctgtac at                                                        12

<210> SEQ ID NO 66
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate
```

-continued

```
<400> SEQUENCE: 66
catccaaact cttgag                                                  16

<210> SEQ ID NO 67
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 67
gctttcatgc acagga                                                  16

<210> SEQ ID NO 68
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 68
gaagttcatc aaagaa                                                  16

<210> SEQ ID NO 69
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 69
agttccttga tgtagt                                                  16

<210> SEQ ID NO 70
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 70
gttccttgat gtag                                                    14

<210> SEQ ID NO 71
<211> LENGTH: 12
<212> TYPE: DNA
<213> ORGANISM: artificial
<220> FEATURE:
<223> OTHER INFORMATION: LNA oligomer Sequence/oligomer Sequence motif
```

```
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 71
ttccttgatg ta                                                              12

<210> SEQ ID NO 72
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 72
ttgcacagag atgatc                                                          16

<210> SEQ ID NO 73
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 73
gatgggcttg actttc                                                          16

<210> SEQ ID NO 74
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 74
atgggcttga cttt                                                            14

<210> SEQ ID NO 75
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 75
tgggcttgac tt                                                              12

<210> SEQ ID NO 76
<211> LENGTH: 16
<212> TYPE: DNA
<213> ORGANISM: artificial
<220> FEATURE:
<223> OTHER INFORMATION: LNA oligomer Sequence/oligomer Sequence motif
```

```
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 76
caggcagaag acatct                                                        16

<210> SEQ ID NO 77
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 77
cccaaggcac tgcaga                                                        16

<210> SEQ ID NO 78
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 78
ccaaggcact gcag                                                          14

<210> SEQ ID NO 79
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 79
caaggcactg ca                                                            12

<210> SEQ ID NO 80
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 80
gctgacattc atagcc                                                        16

<210> SEQ ID NO 81
<211> LENGTH: 2999
<212> TYPE: DNA
<213> ORGANISM: Mus musculus

<400> SEQUENCE: 81
```

```
gaattcggtg gaagctacag acaagctcaa ggatggaggt gcagttaggg ctgggaaggg     60
tctacccacg gcccccatcc aagacctatc gaggagcgtt ccagaatctg ttccagagcg    120
tgcgcgaagc gatccagaac ccgggcccca ggcaccctga ggccgctaac atagcacctc    180
ccggcgcctg tttacagcag aggcaggaga ctagccccg gcggcggcgg cggcagcagc     240
acactgagga tggttctcct caagcccaca tcagaggccc cacaggctac ctggccctgg    300
aggaggaaca gcagccttca cagcagcagg cagcctccga gggccaccct gagagcagct    360
gcctccccga gcctggggcg gccaccgctc ctggcaaggg gctgccgcag cagccaccag    420
ctcctccaga tcaggatgac tcagctgccc catccacgtt gtccctgctg gccccactt     480 tcccaggctt aagcagctgc tccgccgaca ttaaagacat tttgaacgag gccggcacca    540
tgcaacttct tcagcagcag caacaacagc agcagcacca acagcagcac caacagcacc    600
aacagcagca ggaggtaatc tccgaaggca gcagcgcaag agccaggag gccacggggg     660 ctccctcttc ctccaaggat agttacctag ggggcaattc aaccatatct gacagtgcca    720
aggagttgtg taaagcagtg tctgtgtcca tgggattggg tgtggaagca ttggaacatc    780
tgagtccagg gaacagcttc ggggagact gcatgtacgc gtcgctcctg ggaggtccac     840
ccgcggtgcg tcccactcct tgtgcgccgc tgcccgaatg caaaggtctt cccctggacg    900
aaggcccagg caaaagcact gaagagactg ctgagtattc ctctttcaag ggaggttacg    960
ccaaaggatt ggaaggtgag agcttggggt gctctggcag cagtgaagca ggtagctctg   1020
ggacacttga gatcccgtcc tctctgtctc tgtataaatc tggagcacta gacgaggcag   1080
cagcatacca gaatcgcgac tactacaact ttccgctggc tctgtccggg ccgccgcacc   1140
ccccgccccc tacccatcca cacgcccgta tcaagctgga aacccattg gactacggca    1200 gcgcctgggc tgcggcggca gcgcaatgcc gctatgggga cttgggtagt ctacatggag   1260
ggagtgtagc cgggcccagc actggatcgc ccccagccac cacctcttct tcctggcata   1320
ctctcttcac agctgaagaa ggccaattat atgggccagg aggcgggggc ggcagcagca   1380
gcccaagcga tgccgggcct gtagcccct atggctacac tcggcccct caggggctga    1440 caagccagga gagtgactac tctgcctccg aagtgtggta tcctggtgga gttgtgaaca   1500
gagtacccta tccagtccc aattgtgtca aaagtgaaat gggaccttgg atggagaact    1560
actccggacc ttatggggac atgcgtttgg acagtaccag ggaccatgtt ttacccatcg   1620
actattactt tccaccccag aagacctgcc tgatctgtgg agatgaagct tctggctgtc   1680
actacggagc tctcacttgt ggcagctgca aggtcttctt caaaagagcc gctgaaggga   1740
aacagaagta tctatgtgcc agcagaaacg attgtaccat tgataaattt cggaggaaaa   1800
attgcccatc ttgtcgtctc cggaaatgtt atgaagcagg gatgactctg ggagctcgta   1860
agctgaagaa acttgaaat ctaaaactac aggaggaagg agaaaactcc aatgctggca    1920
gccccactga ggacccatcc cagaagatga ctgtatcaca cattgaaggc tatgaatgtc   1980
agcctatctt tcttaacgtc ctggaagcca ttgagccagg agtggtgtgt gccgacatg    2040 acaacaacca accagattcc tttgctgcct tgttatctag cctcaatgag cttggagaga   2100
ggcagcttgt gcatgtggtc aagtgggcca aggccttgcc tggcttccgc aacttgcatg   2160
tggatgacca gatggcggtc attcagtatt cctggatggg actgatggta tttgccatgg   2220
gttggcggtc cttcactaat gtcaactcca ggatgctcta ctttgcacct gacttggttt   2280
tcaatgagta ccgcatgcac aagtctcgga tgtacagcca gtgtgtgagg atgaggcacc   2340
tgtctcaaga gtttggatgg ctccaaataa cccccagga attcctgtgc atgaaagcac    2400
```

```
tgctgctctt cagcattatt ccagtggatg ggctgaaaaa tcaaaaattc tttgatgaac    2460
ttcgaatgaa ctacatcaag gaactcgatc gcatcattgc atgcaaaaga aagaatccca    2520
catcctgctc aaggcgcttc taccagctca ccaagctcct ggattctgtg cagcctattg    2580
caagagagct gcatcagttc acttttgacc tgctaatcaa gtcccatatg gtgagcgtgg    2640
actttcctga aatgatggca gagatcatct ctgtgcaagt gcccaagatc ctttctggga    2700
aagtcaagcc catctatttc cacacacagt gaagatttgg aaaccctaat acccaaaacc    2760
caccttgttc cctttccaga tgtcttctgc ctgttatata actctgcact acttctctgc    2820
agtgccttgg gggaaattcc tctactgatg tacagtctgt cgtgaacagg ttcctcagtt    2880
ctatttcctg ggcttctcct tcttttttt tcttcttccc tccctctttc accctcccat    2940
ggcacatttt gaatctgctg cgtattgtgg ctcctgcctt tgttttgatt tctgttgta     2999

<210> SEQ ID NO 82
<211> LENGTH: 3175
<212> TYPE: DNA
<213> ORGANISM: Macaca mulatta

<400> SEQUENCE: 82
cccaaaaaat aaaacaaac aaaaacaaaa caaaacaaaa aaacgaata aagaaaaagg      60 taataactca gttcttattt gcacctactt ccagtggaca ctgaatttgg aaggtggagg    120
attcttgttt tttcttttaa gatcgggcat cttttgaatc tacccctcaa gtgttaagag    180
acagactgtg agcctagcag ggcagatctt gtccaccgtg tgtcttcttt tgcaggagac    240
tttgaggctg tcagagcgct ttttgcgtgg ttgctcccgc aagtttcctt ctctggagct    300
tcccgcaggt gggcagctag ctgcagcgac taccgcatca tcacagcctg ttgaactctt    360
ctgagcaaga gaaggggagg cggggtaagg gaagtaggtg gaagattcag ccaagctcaa    420
ggatggaggt gcagttaggg ctggggaggg tctacccctcg gccgccgtcc aagacctacc    480
gaggagcttt ccagaatctg ttccagagcg tgcgcgaagt gatccagaac ccgggcccca    540
ggcacccaga ggccgcgagc gcagcacctc ccggcgccag tttgcagcag cagcagcagc    600
agcagcaaga aactagcccc cggcaacagc agcagcagca gcagggtgag gatggttctc    660
cccaagccca tcgtagaggc cccacaggct acctggtcct ggatgaggaa cagcagcctt    720
cacagcctca gtcagccccg gagtgccacc ccgagagagg ttgcgtccca gagcctggag    780
ccgccgtggc cgccggcaag gggctgccgc agcagctgcc agcacctccg gacgaggatg    840
actcagctgc cccatccacg ttgtctctgc tgggccccac tttccccggc ttaagcagct    900
gctccgccga ccttaaagac atcctgagcg aggccagcac catgcaactc cttcagcaac    960
agcagcagga agcagtatcc gaaggcagca gcagcgggag agcgagggag gcctcggggg    1020
ctcccacttc ctccaaggac aattacttag agggcacttc gaccatttct gacagcgcca    1080
aggagctgtg taaggcagtg tcggtgtcca tgggcttggg tgtggaggcg ttggagcatc    1140
tgagtccagg ggaacagctt cggggggatt gcatgtacgc cccagttttg ggagttccac    1200
ccgctgtgcg tcccactccg tgtgcccat tggccgaatg caaaggttct ctgctagacg    1260
acagcgcagg caagagcact gaagatactg ctgagtattc ccctttcaag ggaggttaca    1320
ccaaagggct agaaggcgag agcctaggct gctctggcag cgctgcagca gggagctccg    1380
ggacacttga actgccgtcc accctgtctc tctacaagtc cggagcactg gacgaggcag    1440
ctgcgtacca gagtcgcgac tactacaact ttccactggc tctggccggg ccgccgcccc    1500
ctccaccgcc tccccatccc cacgctcgca tcaagctgga gaacccgctg gactatggca    1560
```

```
gcgcctgggc ggctgcggcg gcgcagtgcc gctatgggga cctggcgagc ctgcatggcg    1620
cgggtgcagc gggacccggc tctgggtcac cctcagcggc cgcttcctca tcctggcaca    1680
ctctcttcac agccgaagaa ggccagttgt atggaccgtg tggtggtggg ggcggcggcg    1740
gtggcggcgg cggcggcggc gcaggcgagg cgggagctgt agccccctac ggctacactc    1800
ggccacctca ggggctggcg ggccaggaag gcgacttcac cgcacctgat gtgtggtacc    1860
ctggcggcat ggtgagcaga gtgccctatc ccagtcccac ttgtgtcaaa agcgagatgg    1920
gcccctggat ggatagctac tccggacctt acggggacat gcgtttggag actgccaggg    1980
accatgtttt gccaattgac tattactttc cacccccagaa gacctgcctg atctgtggag    2040
atgaagcttc tgggtgtcac tatggagctc tcacatgtgg aagctgcaag gtcttcttca    2100
aaagagccgc tgaagggaaa cagaagtacc tgtgtgccag cagaaatgat tgcactattg    2160
ataaattccg aaggaaaaat tgtccatctt gccgtcttcg gaaatgttat gaagcaggga    2220
tgactctggg agcccggaag ctgaagaaac ttggtaatct gaaactacag gaggaaggag    2280
aggcttccag caccaccagc cccactgagg agacagccca aagctgaca gtgtcacaca    2340 ttgaaggcta tgaatgtcag cccatctttc tgaatgtcct ggaggccatt gagccaggtg    2400
tggtgtgtgc tggacatgac aacaaccagc ccgactcctt cgcagccttg ctctctagcc    2460
tcaatgaact gggagagaga cagcttgtac atgtggtcaa gtgggccaag gccttgcctg    2520
gcttccgcaa cttacacgtg gacgaccaga tggctgtcat tcagtactcc tggatggggc    2580
tcatggtgtt tgccatgggc tggcgatcct tcaccaatgt caactccagg atgctctact    2640
ttgcccctga tctggttttc aatgagtacc gcatgcacaa atcccggatg tacagccagt    2700
gtgtccgaat gaggcacctc tctcaagagt ttggatggct ccaaatcacc ccccaggaat    2760
tcctgtgcat gaaagcgctg ctactcttca gcattattcc agtggatggg ctgaaaaatc    2820
aaaaattctt tgatgaactt cgaatgaact acatcaagga actcgatcgt atcattgcat    2880
gcaaaagaaa aaatcccaca tcctgctcaa ggcgtttcta ccagctcacc aagctcctgg    2940
actccgtgca gcctattgcg agagagctgc atcagttcac ttttgacctg ctaatcaagt    3000
cacacatggt gagcgtggac tttccggaaa tgatggcaga gatcatctct gtgcaagtgc    3060
ccaagatcct ttctgggaaa gtcaagccca tctatttcca cacccagtga agcattggaa    3120
atccctattt cctcaccca gctcatgccc cctttcagat gtcttctgcc tgtta          3175
```

<210> SEQ ID NO 83
<211> LENGTH: 920
<212> TYPE: PRT
<213> ORGANISM: Homo sapiens

<400> SEQUENCE: 83

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
            85                  90                  95
```

```
Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
            115                 120                 125

Arg Gly Cys Val Pro Glu Pro Gly Ala Ala Val Ala Ala Ser Lys Gly
130                 135                 140

Leu Pro Gln Gln Leu Pro Ala Pro Pro Asp Glu Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
                180                 185                 190

Leu Leu Gln Gln Gln Gln Glu Ala Val Ser Glu Gly Ser Ser Ser
            195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
                260                 265                 270

Leu Gly Val Pro Pro Ala Val Arg Pro Thr Pro Cys Ala Pro Leu Ala
            275                 280                 285

Glu Cys Lys Gly Ser Leu Leu Asp Asp Ser Ala Gly Lys Ser Thr Glu
    290                 295                 300

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Ala Gly Ser Ser
                325                 330                 335

Gly Thr Leu Glu Leu Pro Ser Thr Leu Ser Leu Tyr Lys Ser Gly Ala
            340                 345                 350

Leu Asp Glu Ala Ala Ala Tyr Gln Ser Arg Asp Tyr Tyr Asn Phe Pro
            355                 360                 365

Leu Ala Leu Ala Gly Pro Pro Pro Pro Pro Pro Pro His Pro His
    370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
            420                 425                 430

Ser Ser Trp His Thr Leu Phe Thr Ala Glu Glu Gly Gln Leu Tyr Gly
            435                 440                 445

Pro Cys Gly Gly Gly Gly Gly Gly Gly Gly Gly Gly Gly Gly Gly
    450                 455                 460

Gly Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
```

515                 520                 525

Asp Ser Tyr Ser Gly Pro Tyr Gly Asp Met Arg Leu Glu Thr Ala Arg
    530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
        595                 600                 605

Arg Lys Asn Cys Pro Ser Cys Arg Leu Arg Lys Cys Tyr Glu Ala Gly
    610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
                645                 650                 655

Thr Gln Lys Leu Thr Val Ser His Ile Glu Gly Tyr Glu Cys Gln Pro
            660                 665                 670

Ile Phe Leu Asn Val Leu Glu Ala Ile Glu Pro Gly Val Val Cys Ala
        675                 680                 685

Gly His Asp Asn Asn Gln Pro Asp Ser Phe Ala Ala Leu Leu Ser Ser
    690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
                725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
        755                 760                 765

Leu Val Phe Asn Glu Tyr Arg Met His Lys Ser Arg Met Tyr Ser Gln
    770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
            820                 825                 830

Met Asn Tyr Ile Lys Glu Leu Asp Arg Ile Ile Ala Cys Lys Arg Lys
        835                 840                 845

Asn Pro Thr Ser Cys Ser Arg Arg Phe Tyr Gln Leu Thr Lys Leu Leu
    850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
            900                 905                 910

Lys Pro Ile Tyr Phe His Thr Gln
        915                 920

<210> SEQ ID NO 84
<211> LENGTH: 899

```
<212> TYPE: PRT
<213> ORGANISM: Mus musculus

<400> SEQUENCE: 84

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Ala Ile Gln Asn Pro Gly Pro Arg His Pro Glu Ala Ala Asn Ile Ala
        35                  40                  45

Pro Pro Gly Ala Cys Leu Gln Gln Arg Gln Glu Thr Ser Pro Arg Arg
    50                  55                  60

Arg Arg Arg Gln Gln His Thr Glu Asp Gly Ser Pro Gln Ala His Ile
65                  70                  75                  80

Arg Gly Pro Thr Gly Tyr Leu Ala Leu Glu Glu Glu Gln Pro Ser
                85                  90                  95

Gln Gln Gln Ala Ala Ser Glu Gly His Pro Glu Ser Ser Cys Leu Pro
            100                 105                 110

Glu Pro Gly Ala Ala Thr Ala Pro Gly Lys Gly Leu Pro Gln Gln Pro
        115                 120                 125

Pro Ala Pro Pro Asp Gln Asp Asp Ser Ala Ala Pro Ser Thr Leu Ser
    130                 135                 140

Leu Leu Gly Pro Thr Phe Pro Gly Leu Ser Ser Cys Ser Ala Asp Ile
145                 150                 155                 160

Lys Asp Ile Leu Asn Glu Ala Gly Thr Met Gln Leu Leu Gln Gln Gln
                165                 170                 175

Gln Gln Gln Gln Gln His Gln Gln His Gln Gln His Gln Gln Gln
            180                 185                 190

Gln Glu Val Ile Ser Glu Gly Ser Ser Ala Arg Ala Arg Glu Ala Thr
        195                 200                 205

Gly Ala Pro Ser Ser Ser Lys Asp Ser Tyr Leu Gly Gly Asn Ser Thr
    210                 215                 220

Ile Ser Asp Ser Ala Lys Glu Leu Cys Lys Ala Val Ser Val Ser Met
225                 230                 235                 240

Gly Leu Gly Val Glu Ala Leu Glu His Leu Ser Pro Gly Glu Gln Leu
                245                 250                 255

Arg Gly Asp Cys Met Tyr Ala Ser Leu Leu Gly Gly Pro Pro Ala Val
            260                 265                 270

Arg Pro Thr Pro Cys Ala Pro Leu Pro Glu Cys Lys Gly Leu Pro Leu
        275                 280                 285

Asp Glu Gly Pro Gly Lys Ser Thr Glu Glu Thr Ala Glu Tyr Ser Ser
    290                 295                 300

Phe Lys Gly Gly Tyr Ala Lys Gly Leu Glu Gly Glu Ser Leu Gly Cys
305                 310                 315                 320

Ser Gly Ser Ser Glu Ala Gly Ser Ser Gly Thr Leu Glu Ile Pro Ser
                325                 330                 335

Ser Leu Ser Leu Tyr Lys Ser Gly Ala Leu Asp Glu Ala Ala Ala Tyr
            340                 345                 350

Gln Asn Arg Asp Tyr Tyr Asn Phe Pro Leu Ala Leu Ser Gly Pro Pro
        355                 360                 365

His Pro Pro Pro Thr His Pro His Ala Arg Ile Lys Leu Glu Asn
    370                 375                 380

Pro Leu Asp Tyr Gly Ser Ala Trp Ala Ala Ala Ala Gln Cys Arg
385                 390                 395                 400
```

-continued

```
Tyr Gly Asp Leu Gly Ser Leu His Gly Gly Ser Val Ala Gly Pro Ser
            405                 410                 415

Thr Gly Ser Pro Pro Ala Thr Thr Ser Ser Trp His Thr Leu Phe
            420                 425                 430

Thr Ala Glu Glu Gly Gln Leu Tyr Gly Pro Gly Gly Gly Gly Ser
            435                 440                 445

Ser Ser Pro Ser Asp Ala Gly Pro Val Ala Pro Tyr Gly Tyr Thr Arg
450                 455                 460

Pro Pro Gln Gly Leu Thr Ser Gln Glu Ser Asp Tyr Ser Ala Ser Glu
465                 470                 475                 480

Val Trp Tyr Pro Gly Gly Val Val Asn Arg Val Pro Tyr Pro Ser Pro
                485                 490                 495

Asn Cys Val Lys Ser Glu Met Gly Pro Trp Met Glu Asn Tyr Ser Gly
            500                 505                 510

Pro Tyr Gly Asp Met Arg Leu Asp Ser Thr Arg Asp His Val Leu Pro
            515                 520                 525

Ile Asp Tyr Tyr Phe Pro Pro Gln Lys Thr Cys Leu Ile Cys Gly Asp
        530                 535                 540

Glu Ala Ser Gly Cys His Tyr Gly Ala Leu Thr Cys Gly Ser Cys Lys
545                 550                 555                 560

Val Phe Phe Lys Arg Ala Ala Glu Gly Lys Gln Lys Tyr Leu Cys Ala
                565                 570                 575

Ser Arg Asn Asp Cys Thr Ile Asp Lys Phe Arg Arg Lys Asn Cys Pro
            580                 585                 590

Ser Cys Arg Leu Arg Lys Cys Tyr Glu Ala Gly Met Thr Leu Gly Ala
            595                 600                 605

Arg Lys Leu Lys Lys Leu Gly Asn Leu Lys Leu Gln Glu Glu Gly Glu
    610                 615                 620

Asn Ser Asn Ala Gly Ser Pro Thr Glu Asp Pro Ser Gln Lys Met Thr
625                 630                 635                 640

Val Ser His Ile Glu Gly Tyr Glu Cys Gln Pro Ile Phe Leu Asn Val
                645                 650                 655

Leu Glu Ala Ile Glu Pro Gly Val Val Cys Ala Gly His Asp Asn Asn
            660                 665                 670

Gln Pro Asp Ser Phe Ala Ala Leu Leu Ser Ser Leu Asn Glu Leu Gly
        675                 680                 685

Glu Arg Gln Leu Val His Val Val Lys Trp Ala Lys Ala Leu Pro Gly
    690                 695                 700

Phe Arg Asn Leu His Val Asp Asp Gln Met Ala Val Ile Gln Tyr Ser
705                 710                 715                 720

Trp Met Gly Leu Met Val Phe Ala Met Gly Trp Arg Ser Phe Thr Asn
                725                 730                 735

Val Asn Ser Arg Met Leu Tyr Phe Ala Pro Asp Leu Val Phe Asn Glu
            740                 745                 750

Tyr Arg Met His Lys Ser Arg Met Tyr Ser Gln Cys Val Arg Met Arg
            755                 760                 765

His Leu Ser Gln Glu Phe Gly Trp Leu Gln Ile Thr Pro Gln Glu Phe
    770                 775                 780

Leu Cys Met Lys Ala Leu Leu Leu Phe Ser Ile Ile Pro Val Asp Gly
785                 790                 795                 800

Leu Lys Asn Gln Lys Phe Phe Asp Glu Leu Arg Met Asn Tyr Ile Lys
                805                 810                 815

Glu Leu Asp Arg Ile Ile Ala Cys Lys Arg Lys Asn Pro Thr Ser Cys
            820                 825                 830
```

Ser Arg Arg Phe Tyr Gln Leu Thr Lys Leu Leu Asp Ser Val Gln Pro
            835                 840                 845

Ile Ala Arg Glu Leu His Gln Phe Thr Phe Asp Leu Leu Ile Lys Ser
850                 855                 860

His Met Val Ser Val Asp Phe Pro Glu Met Met Ala Glu Ile Ile Ser
865                 870                 875                 880

Val Gln Val Pro Lys Ile Leu Ser Gly Lys Val Lys Pro Ile Tyr Phe
            885                 890                 895

His Thr Gln

<210> SEQ ID NO 85
<211> LENGTH: 895
<212> TYPE: PRT
<213> ORGANISM: Macaca mulatta

<400> SEQUENCE: 85

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Gln Gln Gln Gln Gln Gln Gln Gln Glu Thr
    50                  55                  60

Ser Pro Arg Gln Gln Gln Gln Gln Gln Gly Glu Asp Gly Ser Pro
65                  70                  75                  80

Gln Ala His Arg Arg Gly Pro Thr Gly Tyr Leu Val Leu Asp Glu Glu
                85                  90                  95

Gln Gln Pro Ser Gln Pro Gln Ser Ala Pro Glu Cys His Pro Glu Arg
            100                 105                 110

Gly Cys Val Pro Glu Pro Gly Ala Ala Val Ala Ala Gly Lys Gly Leu
        115                 120                 125

Pro Gln Gln Leu Pro Ala Pro Pro Asp Glu Asp Asp Ser Ala Ala Pro
    130                 135                 140

Ser Thr Leu Ser Leu Leu Gly Pro Thr Phe Pro Gly Leu Ser Ser Cys
145                 150                 155                 160

Ser Ala Asp Leu Lys Asp Ile Leu Ser Glu Ala Ser Thr Met Gln Leu
                165                 170                 175

Leu Gln Gln Gln Gln Gln Glu Ala Val Ser Glu Gly Ser Ser Ser Gly
            180                 185                 190

Arg Ala Arg Glu Ala Ser Gly Ala Pro Thr Ser Ser Lys Asp Asn Tyr
        195                 200                 205

Leu Glu Gly Thr Ser Thr Ile Ser Asp Ser Ala Lys Glu Leu Cys Lys
    210                 215                 220

Ala Val Ser Val Ser Met Gly Leu Gly Val Glu Ala Leu Glu His Leu
225                 230                 235                 240

Ser Pro Gly Glu Gln Leu Arg Gly Asp Cys Met Tyr Ala Pro Val Leu
                245                 250                 255

Gly Val Pro Pro Ala Val Arg Pro Thr Pro Cys Ala Pro Leu Ala Glu
            260                 265                 270

Cys Lys Gly Ser Leu Leu Asp Asp Ser Ala Gly Lys Ser Thr Glu Asp
        275                 280                 285

Thr Ala Glu Tyr Ser Pro Phe Lys Gly Gly Tyr Thr Lys Gly Leu Glu
    290                 295                 300

```
Gly Glu Ser Leu Gly Cys Ser Gly Ser Ala Ala Ala Gly Ser Ser Gly
305                 310                 315                 320

Thr Leu Glu Leu Pro Ser Thr Leu Ser Leu Tyr Lys Ser Gly Ala Leu
            325                 330                 335

Asp Glu Ala Ala Ala Tyr Gln Ser Arg Asp Tyr Tyr Asn Phe Pro Leu
        340                 345                 350

Ala Leu Ala Gly Pro Pro Pro Pro Pro Pro Pro His Pro His Ala
    355                 360                 365

Arg Ile Lys Leu Glu Asn Pro Leu Asp Tyr Gly Ser Ala Trp Ala Ala
        370                 375                 380

Ala Ala Ala Gln Cys Arg Tyr Gly Asp Leu Ala Ser Leu His Gly Ala
385                 390                 395                 400

Gly Ala Ala Gly Pro Gly Ser Gly Ser Pro Ser Ala Ala Ala Ser Ser
                405                 410                 415

Ser Trp His Thr Leu Phe Thr Ala Glu Glu Gly Gln Leu Tyr Gly Pro
            420                 425                 430

Cys Gly Gly Gly Gly Gly Gly Gly Gly Gly Gly Gly Gly Gly Ala Gly
            435                 440                 445

Glu Ala Gly Ala Val Ala Pro Tyr Gly Tyr Thr Arg Pro Pro Gln Gly
450                 455                 460

Leu Ala Gly Gln Glu Gly Asp Phe Thr Ala Pro Asp Val Trp Tyr Pro
465                 470                 475                 480

Gly Gly Met Val Ser Arg Val Pro Tyr Pro Ser Pro Thr Cys Val Lys
                485                 490                 495

Ser Glu Met Gly Pro Trp Met Asp Ser Tyr Ser Gly Pro Tyr Gly Asp
                500                 505                 510

Met Arg Leu Glu Thr Ala Arg Asp His Val Leu Pro Ile Asp Tyr Tyr
            515                 520                 525

Phe Pro Pro Gln Lys Thr Cys Leu Ile Cys Gly Asp Glu Ala Ser Gly
        530                 535                 540

Cys His Tyr Gly Ala Leu Thr Cys Gly Ser Cys Lys Val Phe Phe Lys
545                 550                 555                 560

Arg Ala Ala Glu Gly Lys Gln Lys Tyr Leu Cys Ala Ser Arg Asn Asp
                565                 570                 575

Cys Thr Ile Asp Lys Phe Arg Arg Lys Asn Cys Pro Ser Cys Arg Leu
            580                 585                 590

Arg Lys Cys Tyr Glu Ala Gly Met Thr Leu Gly Ala Arg Lys Leu Lys
        595                 600                 605

Lys Leu Gly Asn Leu Lys Leu Gln Glu Glu Gly Glu Ala Ser Ser Thr
    610                 615                 620

Thr Ser Pro Thr Glu Glu Thr Ala Gln Lys Leu Thr Val Ser His Ile
625                 630                 635                 640

Glu Gly Tyr Glu Cys Gln Pro Ile Phe Leu Asn Val Leu Glu Ala Ile
                645                 650                 655

Glu Pro Gly Val Val Cys Ala Gly His Asp Asn Asn Gln Pro Asp Ser
            660                 665                 670

Phe Ala Ala Leu Leu Ser Ser Leu Asn Glu Leu Gly Glu Arg Gln Leu
        675                 680                 685

Val His Val Val Lys Trp Ala Lys Ala Leu Pro Gly Phe Arg Asn Leu
690                 695                 700

His Val Asp Asp Gln Met Ala Val Ile Gln Tyr Ser Trp Met Gly Leu
705                 710                 715                 720

Met Val Phe Ala Met Gly Trp Arg Ser Phe Thr Asn Val Asn Ser Arg
                725                 730                 735
```

```
Met Leu Tyr Phe Ala Pro Asp Leu Val Phe Asn Glu Tyr Arg Met His
            740                 745                 750

Lys Ser Arg Met Tyr Ser Gln Cys Val Arg Met Arg His Leu Ser Gln
        755                 760                 765

Glu Phe Gly Trp Leu Gln Ile Thr Pro Gln Phe Leu Cys Met Lys
    770                 775                 780

Ala Leu Leu Leu Phe Ser Ile Ile Pro Val Asp Gly Leu Lys Asn Gln
785                 790                 795                 800

Lys Phe Phe Asp Glu Leu Arg Met Asn Tyr Ile Lys Glu Leu Asp Arg
                805                 810                 815

Ile Ile Ala Cys Lys Arg Lys Asn Pro Thr Ser Cys Ser Arg Arg Phe
                820                 825                 830

Tyr Gln Leu Thr Lys Leu Leu Asp Ser Val Gln Pro Ile Ala Arg Glu
                835                 840                 845

Leu His Gln Phe Thr Phe Asp Leu Leu Ile Lys Ser His Met Val Ser
            850                 855                 860

Val Asp Phe Pro Glu Met Met Ala Glu Ile Ile Ser Val Gln Val Pro
865                 870                 875                 880

Lys Ile Leu Ser Gly Lys Val Lys Pro Ile Tyr Phe His Thr Gln
                885                 890                 895

<210> SEQ ID NO 86
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 86
tggggagaac catcctcacc ctgc                                          24

<210> SEQ ID NO 87
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 87
tccaggacca ggtagcctgt gggg                                          24

<210> SEQ ID NO 88
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 88
```
tgttcccctg gactcagatg ctcc                                          24

<210> SEQ ID NO 89
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 89
tggggcacaa ggagtgggac gcac                                          24

<210> SEQ ID NO 90
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 90
ttcggctgtg aagagagtgt gcca                                          24

<210> SEQ ID NO 91
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 91
cgcttttgac acaagtggga ctgg                                          24

<210> SEQ ID NO 92
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 92
catagtgaca cccagaagct tcat                                          24

<210> SEQ ID NO 93
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)

-continued

<223> OTHER INFORMATION: nucleotide or nucleotide analogues - optionally
      phosphorothioate

<400> SEQUENCE: 93
gagtcatccc tgcttcataa catt                                           24

<210> SEQ ID NO 94
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 94
gattaccaag tttcttcagc ttcc                                           24

<210> SEQ ID NO 95
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 95
aggccttggc ccacttgacc acgt                                           24

<210> SEQ ID NO 96
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 96
agcatcctgg agttgacatt ggtg                                           24

<210> SEQ ID NO 97
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 97
gacacactgg ctgtacatcc ggga                                           24

<210> SEQ ID NO 98
<211> LENGTH: 24
<212> TYPE: DNA
<213> ORGANISM: artificial

```
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 98
gagccatcca aactcttgag agag                                              24

<210> SEQ ID NO 99
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 99
cagtgctttc atgcacagga attc                                              24

<210> SEQ ID NO 100
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 100
attcgaagtt catcaaagaa tttt                                              24

<210> SEQ ID NO 101
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 101
atcgagttcc ttgatgtagt tcat                                              24

<210> SEQ ID NO 102
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 102
gcacttgcac agagatgatc tctg                                              24
```

-continued

```
<210> SEQ ID NO 103
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 103
aatagatggg cttgactttc ccag                                              24

<210> SEQ ID NO 104
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 104
ataacaggca gaagacatct gaaa                                              24

<210> SEQ ID NO 105
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 105
attccccaag gcactgcaga ggag                                              24

<210> SEQ ID NO 106
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 106
atgggctgac attcatagcc ttca                                              24

<210> SEQ ID NO 107
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate
```

```
<400> SEQUENCE: 107
accgattcac tttagc                                               16
```